US007132510B2

(12) United States Patent
Hagay et al.

(10) Patent No.: US 7,132,510 B2
(45) Date of Patent: Nov. 7, 2006

(54) SPECIFIC HUMAN ANTIBODIES FOR SELECTIVE CANCER THERAPY

(75) Inventors: Yocheved Hagay, Rehovot (IL); Janette Lazarovits, Reut (IL); Rachel Guy, Rehovot (IL); Orly Lifshitz, Rishon Lezion (IL); Esther Szanton, Rehovot (IL); Avigdor Levanon, Rehovot (IL); Daniel Plaksin, Rehovot (IL); Tuvia Peretz, Hod Hasharon (IL)

(73) Assignee: Bio-Technology General (Israel) Ltd., Rehovot (IL)

( * ) Notice: Subject to any disclaimer, the term of this patent is extended or adjusted under 35 U.S.C. 154(b) by 108 days.

(21) Appl. No.: 10/029,926

(22) Filed: Dec. 31, 2001

(65) Prior Publication Data

US 2004/0073011 A1    Apr. 15, 2004

Related U.S. Application Data

(60) Provisional application No. 60/258,948, filed on Dec. 29, 2000.

(51) Int. Cl.
| C12P 21/08 | (2006.01) |
| A61K 39/395 | (2006.01) |
| C12P 21/04 | (2006.01) |
| C12N 5/06 | (2006.01) |
| C07H 21/04 | (2006.01) |

(52) U.S. Cl. .............................. 530/387.3; 530/388.1; 530/388.25; 530/388.7; 530/388.73; 424/133.1; 424/135.1; 424/153.1; 435/69.6; 435/328; 536/23.53

(58) Field of Classification Search ............. 530/387.1, 530/387.3, 387.7, 388.1, 388.8, 391.3, 391.7; 424/130.1, 136.1, 138.1, 141.1, 155.1, 181.1, 424/183.1
See application file for complete search history.

(56) References Cited

U.S. PATENT DOCUMENTS

| 5,168,062 A | 12/1992 | Stinski |
| 5,223,409 A | 6/1993 | Ladner et al. |
| 5,385,839 A | 1/1995 | Stinski |
| 5,403,484 A | 4/1995 | Ladner et al. |
| 5,427,908 A | 6/1995 | Dower et al. |
| 5,432,018 A | 7/1995 | Dower et al. |
| 5,659,018 A | 8/1997 | Berndt et al. |
| 5,716,836 A | 2/1998 | Suiko |
| 5,720,954 A | 2/1998 | Hudziak et al. |
| 5,763,215 A | 6/1998 | Blumberg et al. |
| 5,795,776 A | 8/1998 | Fischer |
| 5,821,337 A | 10/1998 | Carter et al. |
| 5,827,817 A | 10/1998 | Larsen et al. |
| 5,843,439 A | 12/1998 | Anderson et al. |
| 5,945,304 A | 8/1999 | Fischer |
| 6,124,267 A | 9/2000 | McEver et al. |
| 6,132,730 A | 10/2000 | Thorpe et al. |
| 6,312,694 B1 | 11/2001 | Thorpe et al. |
| 6,548,636 B1 | 4/2003 | Dragie et al. |
| 6,593,459 B1 | 7/2003 | Cummings et al. |
| 2002/0058034 A1 | 5/2002 | Manjunath et al. |
| 2003/0064410 A1 | 4/2003 | Hubbell et al. |

FOREIGN PATENT DOCUMENTS

| EP | 0 589 877 | 11/1996 |
| WO | WO 93/11778 | 6/1993 |
| WO | WO 94/26787 | 11/1994 |
| WO | WO97/02479 | 1/1997 |
| WO | WO 98/12318 | 3/1998 |
| WO | WO 00/29004 | 5/2000 |

OTHER PUBLICATIONS

Paul W. E. Fundamental Immunology, 3rd edition, 1993, pp. 292-295.*
Altschul et al. "Gapped Blast and PSI-Blast: a new generation of protein database search programs", Nucleic Acids Research, 1997, vol. 25, No. 17, pp. 3389-3402.
Bass, et al. "Hormone Phage: An enrichment method for variant proteins with altered binding properties", Protein Structure, Function and Genetics, 1990 vol. 8, pp. 309-314.
Caron et al., "Murine and Humanized Constructs of Monoclonal Antibody M195 (Anti-CD33) for the therapy of acute myelogenous leukemia", Cancer Supplement, Feb. 1, 1994, vol. 73, No. 3, pp. 1049-1056.
Caron et al., "A Phase 1B trial of humanized monoclonal antibody M195 (Anti-CD33) in myeloid leukemia: specific targeting without immunogenicity".
Cwirla et al., "Peptides on phage: a vast library of peptides for identifying ligands", Proc. Nat'l. Acad. Sci. USA, Aug. 1990, vol. 87, pp. 6378-6382.
Devlin et al., "Random peptide libraries: a source of specific protein binding molecules", Science, vol. 249, pp. 404-406.
Griffiths et al., "Isolation of high affinity human antibodies directly from large synthetic repertoires," EMBO Journal, 1994, vol. 13, No. 14, pp. 3245-3260.

(Continued)

*Primary Examiner*—Larry R. Helms
*Assistant Examiner*—David J. Blanchard
(74) *Attorney, Agent, or Firm*—Kenyon & Kenyon LLP

(57) ABSTRACT

The present invention is directed to novel peptides and polypeptides that specifically bind to target cells and may have anti-cancer activity, especially blood-related cancers. The present invention includes a peptide or polypeptide comprising an Fv molecule, having a heavy variable chain comprising CDR3, CDR2 and CDR1 regions comprising the amino acid sequences SEQ ID NOS:8, 115 and 114, respectively.

12 Claims, 15 Drawing Sheets

OTHER PUBLICATIONS

Henkart, "Lymphocyte-mediated cytotoxicity: two pathways and multiple effector molecules", Immunity, Aug. 1984, vol. 1, pp. 343-346.

Holliger et al., ""Diabodies": small bivalent and bispecific antibody fragments", Proc. Nat'l. Acad. Sci, USA, Jul. 1993, vol. 90, pp. 6444-6448.

Hudson et al., "High avidity scFv multimers: diabodies and triabodies", Journal of Immun. Methods, 1999, vol. 231, pp. 177-189.

Jarvik et al., "Epitope Tagging", Annu. Rev. Genet., 1998, vol. 32, pp. 601-618.

Jurcic et al., ABSTRACT #2528, Blood, 1992 (10 Suppl. Part 1-2).

Kortt et al., "Single-chain Fv fragments of anti-neuraminidase antibody NC10 containing five- and ten-residue linkers form dimers and with zero-residue linker a trimer", Protein Engineering, 1997, vol. 10, No. 4, pp. 423-433.

McCafferty et al., "Phage antibodies: filamentous phage displaying antibody variable domains", Nature, Dec. 6, 1990, vol. 348, pp. 552-554.

McGraw et al., "Characterization of murine and humanized anti-CD33, gelonin immunotoxins reactive against myeloid leukemias", Cancer Immunol. Immunotherapy, 1994, vol. 39, pp. 367-374.

Nissim et al., "Antibody fragments from a 'single pot' phage display library as immunochemical reagents", EMBO Journal, 1994, vol. 13, No. 3, pp. 692-698.

Scott et al., "Searching for peptide ligands with an epitope library", Science, Jul. 27, 1990, vol. 249, pp. 386-390.

Sgouros et al. ABSTRACT #979, J. Nucl. Med. vol. 38 (5 Suppl.).

Sievers et al., ABSTRACT #2246, Blood, vol. 90 (10 Suppl. 1 Part 1).

Smith, "Filamentous Fusion Phage: Novel expression vectors that displayed cloned antigens on the virion surface", Science, Jun. 14, 1985, vol. 228, pp. 1315-1317.

Squier et al., "Cell-mediated cytotoxic mechanisms", Current Opinion in Immunology, 1994, vol. 6, pp. 447-452.

Sun et al., "Antitumour activity of a chimeric antibody against the leucocyte antigen CD48", Cancer Immunol. Immunotherapy, 2000, vol. 48, pp. 595-602.

Takebe et al., "Srα Promoter: an efficient and versatile mammalian cDNA Expression System . . . ", Molecular and Cellular Biology, Jan. 1988, vol. 8, No. 1, pp. 466-472.

Thompson et al. "A fully human antibody neutralising biologically active human TGFβ2 for use in therapy", J. of Immunol. Methods, 1999, vol. 227, pp. 17-26.

Tomlinson et al., The repertoire of human germline $V_H$ segments with different hypervariable loops, J. Mol. Biol., 1992, vol. 227, pp. 776-798.

Adams, G.P. et al., "Prolonged in vivo tumour retention of a human diabody targeting the extracellular domain of human HER2/neu," British Journal of Cancer (1998) vol. 77, No. 9, pp. 1405-1412.

Afshar-Kharghan, Vahid et al., "Human polymorphism of P-selectin glycoprotein ligand 1 attributable to variable numbers of tandem decameric repeats in the mucinlike region," Blood, vol. 97, No. 10, May 15, 2001, pp. 3306-3307.

Altman, John D. et al., "Phenotypic Analysis of Antigen-Specific T Lymphocytes," Science, vol. 274, Oct. 4, 1996, pp. 94-96.

Bundgaard, Jens R. et al., "New Consensus Features for Tyrosine O-Sulfation Determined by Mutational Analysis," The Journal of Biological Chemistry, vol. 272, No. 35, Aug. 29, 1997, pp. 21700-21705.

Clezardin, Philippe et al., "Role of Platelet Membrane Glycoproteins Ib/Ix and Iib/IIIa, and of Platelet α-Granule Proteins in Platelet Aggregation Induced by Human Osteosarcoma Cells," Cancer Research, vol. 53, Oct. 1, 1993, pp. 4695-4700.

Cochran, Jennifer R. et al., "The Relationship of MHC-Peptide Binding and T Cell Activation Probed Using Chemically Defined MHC Class II Oligomers," Immunity, vol. 12, Mar. 2000, pp. 241-250.

de Kruif, John et al., "Leucine Zipper Dimerized Bivalent and Bispecific scFv Antibodies from a Semi-synthetic Antibody Phage Display Library," The Journal of Biological Chemistry, vol. 271, No. 13, Mar. 29, 1996, pp. 7630-7634.

Gasic, Gabriel J. et al., "Antimetastatic Effects Associated with Platelet Reduction," Proc. Natl. Acad. Sci. USA, vol. 61, 1968, pp. 46-52.

Gilbert, Walker et al., "The LAC Operator is DNA," Proc. Natl. Acad. Sci. USA, vol. 58, 1967, p. 2415-2421.

Harrison, Jacqueline L. et al., "Screening of Phage Antibody Libraries," Methods in Enzymology, vol. 267, 1996, pp. 83-109.

Roberts, Jeffrey W. et al., "Lysogenic Induction," Lambda II, Cold Spring Harbor Laboratory, 1983, pp. 123-144.

Hudson, Peter J. et al., "Recombinant antibody constructs in cancer therapy," Current Opinion in Immunology, vol. 11, 1999, pp. 548-557.

Jurcic, J.G. et al., "Targeted alpha-particle therapy for myeloid leukemias: A phase I trial of bismuth-213-HuM195 (anti-CD33)," Blood, 90(suppl.): 504a, 1997.

Kamiyama, Mikio et al., "Inhibition of Human Platelet Glycoprotein IIB/IIIA Binding to Fibrinogen by Tumor Cell Membrane Ptoreins," Cancer Research, vol. 53, Jan. 15, 1993, pp. 221-223.

Karpatkin, S. et al., "Role of Adhesive Proteins in Platelet Tumor Interaction in Vitro and Metastasis Formation In Vivo," J. Clin. Invest., vol. 81, Apr. 1988, pp. 1012-1019.

Kehoe, John W. et al., "Tyrosine sulfation: a modulator of extracellular protein-protein interactions," Chemistry & Biology, vol. 7, No. 3, 2000, pp. R57-R61.

Kieffer, Nelly et al., "Expression of Platelet Glycoprotein Ibα in HEL Cells," The Journal of Biological Chemistry, vol. 261, No. 34, Dec. 5, 1986, pp. 15854-15862.

Kipriyanov, Sergey M. et al., "Single-chain antibody streptavidin fusions; Tetrameric bifunctional scFv-complexes with biotin binding activity and enhanced affinity to antigen," Hum. Antibod. Hybridomas, vol. 6, No. 3, 1995, pp. 93-101.

Kishimoto, Tadamitsu et al. (eds.) Leucocyte Typing VI: Proceedings of the Sixth International Workshop and Conference held in Kobe, Japan, Nov. 10-14, 1996, pp. 1218-1219.

Kostelny, Sheri A. et al., "Formation of a Bispecific Antibody by the Use of Leucine Zippers," The Journal of Immunology, vol. 148, No. 5, Mar. 1, 1992, pp. 1547-1553.

Marks, James D. et al., "By-Passing Immunization Human Antibodies from V-gene Libraries Displayed on Phage", J Mol. Biol., vol. 222, 1991, pp. 581-597.

Moore, Kevin L. et al., "Identification of a Specific Glycoprotein Ligand for P-selectin (CD62) on Myeloid Cells," The Journal of Cell Biology, vol. 118, No. 2, Jul. 1992, pp. 445-456.

Oleksowicz, Leslie et al., "Characterization of Tumor-Induced Platelet Aggregation: The Role of Immunorelated GPIb and GPIIb/IIIa Expression by MCF-7 Breast Cancer Cells," Thrombosis Research, vol. 79, No. 3, 1995, pp. 261-274.

Power, Barbara E. et al., "Synthesis of high avidity antibody fragments (scFv multimers) for cancer imaging," Journal of Immunological Methods, vol. 242, 2000, pp. 193-204.

Ramachandran, Vishwanath et al., "Dimerization of a selectin and its ligand stabilizes cell rolling and enhances tether strength in shear flow," Proc. Natl. Acad. Sci. USA, vol. 98, No. 18, Aug. 28, 2001, pp. 10166-10171.

Rodgers, Stephen D. et al., "Tyrosine Sulfation Enhances but is not Required for PSGL-1 Rolling Adhesion on P-Selectin," Biophysical Journal, vol. 81, Oct. 2001, pp. 2001-2009.

Schmidt, Emmett V. et al., "The Cytomegalovirus Enhancer: a Pan-Active Control Element in Transgenic Mice," Mol. Cell. Biol., vol. 10, Aug. 1990, pp. 4406-4411.

Snapp, Karen R. et al., "A Novel P-Selectin Glycoprotein Ligand-I Monoclonal Antibody Recognizes an Epitope Within the Tyrosine Sulfate Motif of Human PSGL-1 and Blocks Recognition of Both P-and L-Selectin," Blood, vol. 91, No. 1, Jan. 1, 1998, pp. 154-164.

Tomlinson, Stephen, "Complement defense mechanism," Current Opinion in Immunology, vol. 5, 1993, p. 83-89.

Varki, A. et al., "P-selectin, carcinoma metastasis and heparin: novel mechanistic connections with therapeutic implications," Braz. J. Med. Biol. Res., vol. 34, No. 6, 2001, pp. 711-717.

Ward, Christopher M. et al., "Mocarhagin, a Novel Cobra Venom Metalloproteinase, Cleaves the Platelet von Willebrand Factor Receptor Glycoprotein Ibα. Identification of the Sulfated Tyrosine/

Anionic Sequence Tyr-276-Glu-282 of Glycoprotein Ibα as a Binding Site for von Willebrand Factor and α-Thrombin," Biochemistry, vol. 35, No. 15, 1996, pp. 4929-4938.

Wu, Am et al., "Anti-carcinoembryonic antigen (CEA) diabody for rapid tumor targeting and imaging," Tumor Targeting, vol. 4, 1999, pp. 47-58.

Huo, et al., "Adhesion molecules and atherogenesis," Acta Physiol Scand. 2001, vol. 173, pp. 35-43.

Kamiyama, et al., "Inhibition of platelet GPIIb/IIIa binding to fibrinogen by serum factors: Studies of circulating immune complexes and platelet antibodies in patients with hemophilia, immune thrombocytopenic purpura, human immunodeficiency virus—related immune thrombocytopenic purpura, and systemic lupus erythematosus," J. Lab. Clin. Med., (1991) vol. 117, No. 3, pp. 209-217.

Libby, "Atherosclerosis: The New View," Scientific American, May 2002, pp. 28-37.

Ma, et al., "Obligatory Requirement of Sulfation for P-Selectin Binding to Human Salivary Gland Carcinoma Acc-M Cells and Breast Carcinoma ZR-75-30 Cells," Journal of Immunology, 2002, vol. 168, pp. 1690-1696.

Malmborg, et al., "BIAcore as a tool in antibody engineering," Journal of Immunological Methods, 1995, vol. 183, pp. 7-13.

Michelson, et al., "Partial Characterization of a Binding Site For von Willebrand Factor on Glycocalicin," Blood, Jan. 1986, vol. 67, No. 1, pp. 19-26.

Myszka, "Improving Biosensor Analysis", Journal of Mol. Recog., 1999, No. 12, pp. 279-284.

Shebuski, et al., "Role of Inflammatory Mediators in Thrombogenesis," JPET, 2002, vol. 300, No. 3, pp. 729-735.

Wang, et al., "Prevention of Intimal Hyperplasia With Recombinant Soluble P-Selectin Glycoprotein Ligand-Immunoglobulin in the Procine Coronary Artery Balloon Injury Model," JACC, Aug. 2001, vol. 38, No. 2, pp. 577-582.

Hagay, Y., et al., "Function-modulating human monoclonal antibodies against platelet-membrane receptors isolated from a phage-display library" Journal of Thrombasis and Haemostasis, vol. 1, pp. 1829-1836.

Dong, Jing-fei, et al., "Tyrosine Sulfation of the Glycoprotein Ib-IX complex: Identification of Sulfated Residues and Effect on Ligand Binding" Biochemistry, vol. 33, pp. 13946-13953 (1994).

Leyte, Anja, et al., "Sulfation of $Tyr^{1680}$ of Human Blood Coagulaton Factor VIII is Essential for the Interaction of Factor VIII with von Willebrand Factor*" Journal of Biological Chem. vol. 266, No. 2, pp. 740-746 (Jan. 15, 1991).

López, José A., et al., "Cloning of the α chain of human platelet glycoprotein Ib: A transmembrane protein with homology to leucine-rich $α_2$-glycoprotein" Proc. Natl. Acad. Sci. USA, vol. 84, pp. 5615-5619 (Aug. 1997).

López José A., "The Plateet glycoprotein IB-IX complex" Blood Coagulation and Fibrinolysis, vol. 5, pp. 97-119 (1994).

López José A, et al., "Structure and function of the glycoprotein Ib-IX-V complex"Current Opinion in Hematology, vol. 4, pp. 323-329, (1997).

Marchese, Patrizia, et al., "Identification of Three Tyrosine Residues of Glycoprotein Ibα-Thrombin Binding*"The Journal of Biological Chemistry, vol. 270, No. 16, pp. 9571-9578 (Apr. 21, 1995).

Murata, Mitsurü, et al., "Site-directed Mutagenesis of a Soluble Recombinant Fragment of Platelet Glycoprotein Ibα Demonstrating Negatively Charged Residues Involved in von Willebrand Factor Binding*" The Journal of Biological Chemistry, vol. 266, No. 23, pp. 15474-15480, (Aug. 15, 1991).

Okumura, Tadayoshi, et al., "Platelet Glycocalicin" The Journal of Biological Chemistry vol. 251, No. 19, pp. 5950-5955, (Oct. 10, 1976).

Shen, Yang et al., "Requirement of leucine-rich repeats of glycoprotein (GP) Ibα for shear-dependent and static binding of von Willebrand factor to the platelet membrane GP Ib-IX-V complex", Blood, vol. 95, No. 3, pp. 903-910 (Feb. 1, 2000).

Tait, A. Sasha, et al., "Site-directed mutagenesis of platelet glycoprotein Ibα demonstrating residues involved in the sulfation of tyrosines 276, 278, and 279", Blood, vol. 99, No. 12, pp. 4422-4427 (Jun. 15, 2002).

Tcheng, James E., et al., "Pharmacodynamics of Chimeric Glycoprotein IIb/IIIa Integrin Antiplatelet Antibody Fab 7E3 in High-Risk Coronary Angioplasty" Circulation, vol. 90, No. 4, pp. 1757-1764 (Oct. 1994.

Titani, Koiti, et al., "Amino acid sequence of the von Willebrand factor-binding domain of platelet membrane glycoprotein Ib", Proc. Natl. Acad. Sci. USA, vol. 84, pp. 5610-5614 (Aug. 1987).

Vicente, Vicente, et al., "Identification of a Site in the α Chain of Platelet Glycoprotein Ib That Participates in von Willebrand Factor Binding*", The Journal of Biological Chemistry, vol. 265, No. 1, pp. 274-280 (Jan. 5, 1990).

Wilkins, Patricia P., et al., "Tyrosine Sulfation of P-selectin Glycoprotein Ligand-l Is Required for High Affinity binding to P-selectin*", The Journal of Biological Chemistry, vol. 270, No. 39, pp. 22677-22680 (Sep. 29, 1995).

Katagiri, Yasuhiro, et al., "Localization of von Willebrand Factor and Thrombin-Interactive Domains on Human Platelet Glycoprotein Ib" Schattauer Verlagsgesellschaft mbH (Stuttgart) vol. 63, No. 1, pp. 122-126 (1990).

Marco, Luigi De, et al., "Localization and Characterization of an α-Thrombin-binding Site on Platelet Glycoprotein Ibα*", The Journal of biological Chemistry, vol. 269, No. 9, pp. 6478-6484 (1994).

Pidard, D., et al, Neutrophil proteinase cathepsin G is proteolytically active on the human platelet glycoprotein Ib-IX receptor: characterization of the cleavage sites within the glycoprotein Ibα subunit, vol. 303, pp. 490-498, J. Biochemistry Oct. (1994).

Tsujino, Shiho, et al., "Primary Structure jof Light and heavy Chain Variable Regions of Antibodies Recognizing Phosphorylated Vimentins" Biochemical and Biophysical Research Communications, vol. 219, Article No. 0285, pp. 633-637 (1996).

Frenette, P.S., P-Selectin Glycoprotein Ligand I (PSGL-1) Is Expressed on Platelets and Can Mediate Platelet-Endothelial Interactions In Vivo, J. Exp. Med. vol. 191, No. 8, pp. 1413-1422 (Apr. 17, 2000).

Roubey, Robert A.S., "Autoantibodies to Phospholipid-Binding Plasma Proteins: A New View of Lupus Anticoagulants and Other "Antiphospholipid" Autoantibodies", Blood, vol. 84, No. 9, pp. 2854-2867 (Nov. 1, 1994).

Muramatsu, Ryo et al., "Structure/Activity Relationships of Hirudin Peptides Containing Sulfated Tyrosine Residues" Protein Research Foundation, Osaka pp. 297-300 (1995).

Leppänen, Anne et al., "A Novel Glycosulfopeptide Binds to P-Selectin and Inhibits Leukocyte Adhesion to P-selectin" The Journal of Biological Chemistry, vol., 274, No. 35, pp. 24838-24848 (Aug. 27, 1999).

Arvieux, et al., Blood, 1999, vol. 93, pp. 4248-4255.

Austin, et al., Molecular Biology of the Cell, Nov. 2001, Suppl., p62a, abstract No. 338.

Somers, et al., Cell, 2000, vol. 103, pp. 467-479.

de Kruif, J. et al., "New prespectives on recombinant human antibodies" Immunology Today, Elsevier Publications, vol. 17 No. 10, pp. 453-455, Oct. 1, 1996.

de Kruif, J. et al, "Rapid Selection of cell subpopulation-specific human monoclonal antibodies from a synthetic phage antibody library" Proc. Natl. Acad. Sci, vol. 92, pp. 3938-3942, Apr. 1995.

Hoogenboom, H.R., et al., "Antibody phage display technology and its applications" Immunotechnology vol. 4, No. 1, pp. 1-20, Jun. 1, 1998.

Hoogenboom, H.R., "Designing and optimizing library selection strategies for generating high-affinity antibodies" Trends in biotechnology, vol. 15, No. 2, pp. 62-70, Feb. 1, 1997.

* cited by examiner

Figure 14

Y17 scFv

<210> 203

<211> 277

<212> PRT

<213> Homo sapiens

<400> 203

Met Lys Tyr Leu Leu Pro Thr Ala Ala Ala Gly Leu Leu Leu Leu Ala
1               5                   10                  15

Ala Gln Pro Ala Met Ala Glu Val Gln Leu Val Glu Ser Gly Gly Gly
            20                  25                  30

Val Val Arg Pro Gly Gly Ser Leu Arg Leu Ser Cys Ala Ala Ser Gly
        35                  40                  45

Phe Thr Phe Asp Asp Tyr Gly Met Ser Trp Val Arg Gln Ala Pro Gly
    50                  55                  60

Lys Gly Leu Glu Trp Val Ser Gly Ile Asn Trp Asn Gly Gly Ser Thr
65                  70                  75                  80

Gly Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
                100                 105                 110

Thr Ala Val Tyr Tyr Cys Ala Arg Leu Thr His Pro Tyr Phe Trp Gly
            115                 120                 125

Gln Gly Thr Leu Val Thr Val Ser Arg Gly Gly Gly Gly Ser Gly Gly
        130                 135                 140

Gly Gly Ser Gly Gly Gly Ser Ser Glu Leu Thr Gln Asp Pro Ala
145                 150                 155                 160

Val Ser Val Ala Leu Gly Gln Thr Val Arg Ile Thr Cys Gln Gly Asp
                165                 170                 175

Ser Leu Arg Ser Tyr Tyr Ala Ser Trp Tyr Gln Gln Lys Pro Gly Gln
            180                 185                 190

Ala Pro Val Leu Val Ile Tyr Gly Lys Asn Asn Arg Pro Ser Gly Ile
        195                 200                 205

Pro Asp Arg Phe Ser Gly Ser Ser Ser Gly Asn Thr Ala Ser Leu Thr

```
            210                     215                     220
Ile Thr Gly Ala Gln Ala Glu Asp Glu Ala Asp Tyr Tyr Cys Asn Ser
225                     230                     235                     240

Arg Asp Ser Ser Gly Asn His Val Val Phe Gly Gly Gly Thr Lys Leu
                245                     250                     255

Thr Val Leu Gly Ala Ala Ala Glu Gln Lys Leu Ile Ser Glu Glu Asp
                260                     265                     270

Leu Asn Gly Ala Ala
        275
```

SPECIFIC HUMAN ANTIBODIES FOR SELECTIVE CANCER THERAPY

This application claims priority to provisional application Ser. No. 60/258,948, filed on Dec. 29, 2000, the subject matter of which is incorporated by reference hereto.

FIELD OF THE INVENTION

The present invention relates to the field of tissue targeting and identification, with the aid of phage display technology, of peptides and polypeptides that specifically bind to target cells. Such peptides and polypeptides are Fv molecules, constructs thereof, fragments of either or constructs of a fragment. More particularly, the peptides and polypeptides may have anti-cancer activity, and/or are associated with, or conjugated to, anti-cancer agents, especially against blood-related cancers.

BACKGROUND OF THE INVENTION

Tissue-selective targeting of therapeutic agents is an emerging discipline in the pharmaceutical industry. New cancer treatments based on targeting have been designed to increase the specificity and potency of the treatment, while reducing toxicity, thereby enhancing overall efficacy. Mouse monoclonal antibodies (MAb's) to tumor-associated antigens have been employed in an attempt to target toxin, radionucleotide, and chemotherapeutic conjugates to tumors. In addition, differentiation antigens, such as CD 19, CD20, CD22 and CD25, have been exploited as cancer specific targets in treating hematopoietic malignancies. Although extensively studied, this approach has several limitations. One limitation is the difficulty of isolating appropriate monoclonal antibodies that display selective binding. A second limitation is the need for high antibody immunogenicity as a prerequisite for successful antibody isolation. A third limitation is the elicitation in the patient of an immune response against murine antibodies (human anti-mouse antibody-HAMA response) that often results in a shorter serum half-life, and prevents repetitive treatments, thus diminishing the therapeutic value of the antibody. This latter limitation has stimulated interest both in engineering chimeric or humanized monoclonal antibodies of murine origin, and in discovering human antibodies.

There are many factors that influence the therapeutic efficacy of monoclonal antibodies (Mabs) for treating cancer. These factors include specificity of antigen expression on tumor cells, level of expression, antigenic heterogeneity, and accessibility of the tumor mass. Leukemia and lymphoma have been generally more responsive to treatment with antibodies than solid tumors, such as carcinomas. MAbs rapidly bind to leukemia and lymphoma cells in the bloodstream and easily penetrate to malignant cells in lymphatic tissue, thus making lymphoid tumors excellent candidates for MAb-based therapy. An ideal system would entail identifying a MAb that recognizes a marker on the cell surface of stem cells that produce malignant progeny cells.

To aid in the discovery/production of Mabs, phage libraries have been used to select random single chain Fvs (scFvs) that bind to isolated, pre-determined target proteins such as antibodies, hormones and receptors. In addition, the use of antibody display libraries in general, and phage scFv libraries in particular, facilitates an alternative means of discovering unique molecules for targeting specific, yet unrecognized and undetermined, cell surface moieties.

Leukemia, lymphoma, and myeloma are cancers that originate in the bone marrow and lymphatic tissues and are involved in uncontrolled growth of cells. Acute lymphoblastic leukemia ("ALL") is a heterogeneous disease that is defined by specific clinical and immunological characteristics. Like other forms of ALL, the definitive cause of most cases of B-cell ALL ("B-ALL") is not known, although in many cases, the disease results from acquired genetic alterations in the DNA of a single cell, causing it to become abnormal and multiply continuously Acute Myelogenous Leukemia (AML) is a heterogeneous group of neoplasms with a progenitor cell that, under normal conditions, gives rise to terminally differentiated cells of the myeloid series (erythrocytes, granulocytes, monocytes, and platelets). As in other forms of neoplasia, AML is associated with acquired genetic alterations that result in replacement of normally differentiated myeloid cells with relatively undifferentiated blasts, exhibiting one or more type of early myeloid differentiation. AML generally evolves in the bone marrow and, to a lesser degree, in the secondary hematopoietic organs. AML primarily affects adults, peaking in incidence between the ages of 15–40, but it is also known to affect both children and older adults. Nearly all patients with AML require treatment immediately after diagnosis to achieve clinical remission, in which there is no evidence of abnormal levels of circulating undifferentiated blast cells.

To date, a variety of monoclonal antibodies have been developed that induce cytolytic activity against tumor cells. A humanized version of the monoclonal antibody MuMAb4D5, directed to the extracellular domain of P185—growth factor receptor (HER2)—was approved by the FDA and is being used to treat human breast cancer (U.S. Pat. Nos. 5,821,337 and 5,720,954). Following binding, the antibody is capable of inhibiting tumor cell growth that is dependent on the HER2 growth factor receptor. In addition, a chimeric antibody against CD20, which causes rapid depletion of peripheral B cells, including those associated with lymphoma, was recently approved by the FDA (U.S. Pat. No. 5,843,439). The binding of this antibody to target cells results in complement-dependent lysis. This product has recently been approved and is currently being used in the clinic to treat low-grade B-cell non-Hodgkin's lymphoma.

Several other humanized and chimeric antibodies are under development or are in clinical trials. In addition, a humanized Ig that specifically reacts with CD33 antigen, expressed both on normal myeloid cells as well as on most types of myeloid leukemic cells, was conjugated to the anti-cancer drug calicheamicin, CMA-676 (Sievers et al., *Blood Supplement*, 308, 504a (1997)). This conjugate, known as the drug MYLOTARG®, has recently received FDA approval (Caron et al., *Cancer Supplement*, 73, 1049–1056 (1994)). In light of its cytolytic activity, an additional anti-CD33 antibody (HumM 195), currently in clinical trials, was conjugated to several cytotoxic agents, including the gelonin toxin (McGraw et al., *Cancer Immunol. Immunother*, 39, 367–374 (1994)) and radioisotopes $^{131}$I (Caron et al., *Blood* 83, 1760–1768 (1994)), $^{90}$Y (Jurcic et al., *Blood Supplement*, 92, 613a (1998)) and $^{213}$Bi (Humm et al., *Blood Supplement*, 38:231P (1997)).

A chimeric antibody against the leukocyte antigen CD-45 (cHuLym3) is in preclinical phase for treatment of human leukemia and lymphoma (Sun et al., *Cancer Immunol. Immunother.*, 48, 595–602 (2000)) as a conditioning for bone marrow transplantation. In in vitro assays, specific cell lysis was observed in ADCC (antibody dependent cell-mediated cytotoxicity) assays (Henkart, *Immunity*, 1, 343–346 (1994); Squier and Cohen, *Current Opin. Immunol.*, 6, 447–452 (1994)).

Although these preliminary results seem promising, they have the following limitations. The final product comprises non-human sequences, resulting in a problematic immune response to non-human material, such as HAMA. This HAMA response prevents repetitive treatments and results in a shorter serum half-life for the product. In addition, the above methods allow for the isolation of a single antibody species only, and only allow for the isolation of antibodies against known and purified antigens. Further, these methods are not selective insofar as they allow for the isolation of antibodies against cell surface markers that are present on normal cells as well as on malignant cells.

Thus, a method, which overcomes these above discussed limitations, would be desirable. Further, such method would ideally enable the identification of target ligands or markers on cancer cells or cells involved in mediating metastis of cancer cells, for example. Additionally, such method would also enable the production of antibodies to such targets. Phage display technology appears to offer such abilities.

The use of phage display technology has enabled the isolation of scFvs comprising fully human sequences. For example, fully human antibody against the human TGFb2 receptor based on a scFv clone derived from phage display technology was recently developed. This scFv, converted into a fully human IgG4 that is capable of competing with the binding of TGFb2 (Thompson et al., *J. Immunol Methods*, 227, 17–29 (1999)), has strong anti-proliferative activity. This technology, known to one skilled in the art, is more specifically described in the following publications: Smith, *Science*, 228, 1315 (1985); Scott et al, *Science*, 249, 386–390 (1990); Cwirla et al., *PNAS*, 87, 6378–6382 (1990); Devlin et al., *Science*, 249, 404–406 (1990); Griffiths et al., *EMBO J.*, 13(14), 3245–3260 (1994); Bass et al., *Proteins*, 8, 309–314 (1990); McCafferty et al., *Nature*, 348, 552–554(1990); Nissim et al., *EMBO J.*, 13, 692 –698 (1994); U.S. Pat. Nos. 5,427,908, 5,432,018, 5,223,409 and 5,403,484, lib.

Using this phage display technology, the inventors of the present invention have identified cell markers present on or cells in diseased or malignant state. Therefore, it is an objective of the present invention to identify peptides and polypeptides that recognize cell markers that are substantially exposed or over-expressed, particularly on or in cells in a diseased or malignant state.

It is a further objective of the present invention to use and expand phage display technology as an aid to identify such peptides and polypeptides.

It is a further objective of the present invention to identify such peptides and polypeptides by immuno-cross-reactivity.

It is a still further objective of the present invention that such peptides and polypeptides be of fully human origin.

It is a still further objective of the present invention that such peptides and polypeptides be isolated against antigens that may not necessarily be immunogenic.

It is a still further objective of the present invention to provide peptides or polypeptides that prevent, retard or cure cancer, particularly blood-related cancers including leukemia or lymphoma.

It is a still further objective of the present invention to provide for local targeting of cancerous cells with such peptides and polypeptides alone, or associated with, or coupled to, an anti-cancer agent and/or a diagnostic label or marker.

It is a still further objective of the present invention to provide a method for producing a targeting agent against desired ligands.

It is a still further objective of the present invention to identify specific motifs that provide for the recognition of cell markers that are over-expressed in the malignant state and that can be used in the construction of a targeting or diagnostic label or marker for an anti-cancer agent.

It is a still further objective of the present invention to provide a composition comprising an effective amount of such peptides, polypeptides or motifs associated with, or coupled to, an anti-cancer agent or to a diagnostic label or marker.

It has been established that scFv penetrate tissues and are cleared from the blood more rapidly than a full size antibody because they are smaller in size. Adams, G. P., et al., Br. J. Cancer 77, 1405–1412 (1988); Hudson, P. J., Curr. Opin. Immunol. 11(5), 548–557 (1999); Wu, A. M., et al., Tumor Targeting 4, 47 (1999). Thus, scFv are often employed in diagnostics involving radioactive labels such as tumor imaging to allow for a more rapid clearance of the radioactive label from the body. A number of cancer targeting scFv multimers have recently undergone pre-clinical evaluation for in vivo stability and efficacy. Adams, G. P., et al., Br. J. Cancer 77, 1405–1412 (1988); Wu, A. M., et al., Tumor Targeting 4, 47 (1999).

Single chain Fv (scFv) fragments are comprised of the variable domains of the heavy ($V_H$) and light ($V_L$) chains of an antibody tethered together by a polypeptide linker. The linker is long enough to allow the ($V_H$) and the ($V_L$) domains to fold into a functional Fv domain enabling the scFv to recognize and bind its target with the similar or increased affinity of the parent antibody. A commonly used linker comprises glycine and serine residues to provide flexibility and protease resistance.

Typically, scFv monomers are designed with the C-terminal end of the $V_H$ domain tethered by a polypeptide linker to the N-terminal residue of the $V_L$. Optionally an inverse orientation is employed: the C-terminal end of the $V_L$ domain is tethered to the N-terminal residue of $V_H$ through a polypeptide linker. Power, B., et al., J. Immun. Meth. 242, 193–204 (2000). The polypeptide linker is typically around twelve amino acids in length. When the linker is reduced to about three to twelve amino acids, the scFvs can not fold into a functional Fv domain and instead associate with a second scFv to form a diabody. Further reducing the length of the linker to less than three amino acids forces the scFv association into trimers or tetramers, depending on the linker length, composition and Fv domain orientations. B. E. Powers, P. J. Hudson, J. Immun. Meth. 242 (2000) 193–194.

Recently, it has been discovered that mulitvalent antibody fragments such as scFv dimers, trimers, and tetramers often provide higher apparent ffinity over the binding of the parent antibody to the target. This higher affinity offers many advantages including ideal pharmaco-kinetics for tumor targeting applications.

The greater binding affinity of these multivalent forms is therefore desirable in diagnostics and therapeutic regimens. For example, a scFv may be employed as a blocking agent to bind a target receptor and thus block the binding of the "natural" ligand. In such instances, it is desirable to have a high affinity association between the scFv and the receptor to decrease chances for disassociation, which may allow an undesirable binding of the natural ligand to the target. In addition, this high affinity is especially critical when the target receptors are involved in adhesion and rolling or when the target receptors are on cells present in areas of high sheer flow, such as platelets.

Therefore, an object of the invention is multivalent forms of Y1 and Y17 scFv. These multivalent forms include, but are not limited to dimers, trimers and tetramers, sometimes referred to herein as diabodies, triabodies, and tetrabodies, respectively.

SUMMARY OF THE INVENTION

The present invention provides for the identification of peptides and polypeptides that bind selectively and/or specifically to target cells especially against blood related cancer cells, their construction, their use on their own, or in association with, or combined, conjugated or fused to one or more pharmaceutical agents.

One embodiment of the present invention provides for a peptide or polypeptide comprising an Fv molecule, a construct thereof, a fragment of either, or a construct of a fragment having enhanced binding characteristics so as to bind selectively and/or specifically to a target cell in favor of other cells, wherein the binding selectivity or specificity is primarily determined by a first hypervariable region, and wherein the Fv is a single chain Fv ("scFv") or a disulfide Fv ("dsFv"), and optionally having one or more tags.

In another embodiment of the present invention there is provided a peptide or polypeptide comprising an Fv molecule, a construct thereof, a fragment of either, or a construct of a fragment having enhanced binding characteristics so as to bind selectively and/or specifically to a substantially exposed and/or overexpressed binding site on, or in, a target comprising a cell in favor of other cells on, or in which, the binding site is not substantially available and/or expressed, wherein the binding selectivity or specificity is primarily determined by a first hypervariable region, and wherein the Fv is a scFv or a dsFv, and optionally having one or more tags.

In a further embodiment of the present invention there is provided a peptide or polypeptide comprising an Fv molecule, a construct thereof, a fragment of either, or a construct of a fragment having enhanced binding characteristics so as to bind selectively and/or specifically to a target cell in favor of other cells, wherein the Fv molecule comprises a first chain having a first, a second and a third hypervariable region and a second chain having a first, a second and a third hypervariable region, wherein one of the hypervariable regions of the first chain has a sequence selected from the group comprising SEQ ID NOs:8–24, and wherein one of the hypervariable regions of the second chain has a sequence selected from the group comprising SEQ ID NOs:1–6 and 125–202, and wherein the first, second, and third hypervariable regions are a CDR3, CDR2 and CDR1 region, respectively, and wherein the Fv is a scFv or a dsFv, and optionally having one or more tags.

In a further embodiment of the invention,
(a) the first and second chain each comprises a first hypervariable region selected from the group comprising SEQ ID NOs:8–24,
(b) the first hypervariable regions of the first and second chains are identical and are selected from the group comprising SEQ ID NOs:8–24,
(c) the first hypervariable region of the first chain is selected from the group comprising SEQ ID NOs:8–24, and the first hypervariable region of the second chain is selected from the group comprising SEQ ID NOs:1–6 and 125–202, or (d) the first hypervariable region of the first chain is selected from the group comprising SEQ ID NOs:1–6 and 125–202, and the first hypervariable region of the second chain is selected from the group comprising SEQ ID NOs:8–24.

In a still further embodiment of the present invention there is provided a peptide or polypeptide comprising an Fv molecule, a construct thereof, a fragment of either or a construct of a fragment that binds to an unknown ligand on a first cell having a first and a second state, wherein the binding is effective in the second state but not substantially in the first state and, by virtue of immuno-cross-reactivity, binds specifically or selectively to a ligand on a second cell, and wherein the Fv is a scFv or a dsFv, and optionally having one or more tags.

In a still further embodiment of the present invention there is provided a method for identifying a targeting molecule which binds to unknown immuno-cross-reactive binding site on first and second cells comprising
(a) one or more biopanning steps that are performed on a first target cell that, in a second state but not in a first state, substantially exposing or displaying a binding site comprising an unknown ligand, so as to produce a first population of recognition molecules;
(b) subsequent biopanning and/or selection steps commencing with the resultant stock of recognition molecules of step (a) that are performed on a second cell that displays a binding site comprising an unknown ligand having immuno-cross-reactivity to the the unknown ligand of the first cell so as to produce a second population of recognition molecules;
(c) amplification and purification of the second population of recognition molecules of step (b); and
(d) construction from the recognition sites of the purified recognition molecules of step (c) peptides or polypeptides that comprise targeting molecules that are selective and/or specific for unknown ligands on the second cell.

In a still further embodiment of the present invention there is provided a binding motif comprising the amino acid sequence of $R_1$-X Phe Pro-$R_2$ wherein $R_1$ and $R_2$ each comprises 0–15 amino acid residues, and wherein X is either Arg, Gly or Lys.

In yet another embodiment of the present invention there is provided a method of production of a targeting agent comprising the following steps:
a) isolating and selecting one or more targeting molecules comprising a primary recognition site by a biopanning procedure directly on a target cell or by a biopanning procedure indirectly on a first target cell in a second but not in a first state, and subsequently by a biopanning procedure directly on a second target cell to produce one or more said targeting molecules;
b) amplification, purification and identification of the one or more targeting molecules;
c) construction of a targeting agent from the one or more targeting molecules or recognition sites thereof;
   wherein the targeting agent can be a peptide, polypeptide, antibody or antibody fragment or a multimer thereof.

In another embodiment of the present invention there is provided a peptide or polypeptide having the formula or structure:

A-X-B wherein X is a hypervariable CDR3 region of 3 to 30 amino acids; A and B can each be amino acid chains from 1 to 1000 amino acids in length, wherein A is the amino end and B is the carboxy end.

BRIEF DESCRIPTION OF THE DRAWINGS

The invention is herein described in more detail, by way of example only, and not by way of limitation, with reference to the accompanying drawings described below, wherein:

FIG. 4c presents a FSC and SSC dot plot analysis of the same FITC-labeled scFv clone Y1 sample as in 4b. The circled areas in FIGS. 4b and 4c delineate the sub-population of CD34+ cells that bind scFv clone Y1.

FIGS. 5a, 5c) or a PE-labeled CD34 (a marker for stem cells; FIG. 5d) was employed, together with a FITC-labeled negative control scFv (5a, 5b) or FITC-labeled Y-I scFv (5c, 5d). FIG. 5b is a double negative control. Fluorescence intensity (x-axis) of cells bound by the FITC-labeled sample (scFv clone Y1), relative to the negative control staining pattern, is presented (5e and 5f).

FIG. 7a) and on Jurkat cells (Y1 positive cells; FIG. 7b). For detection, PE labeled goat anti-human IgG was used. For the binding of the scFv-YI-I~1 µg (200-fold) was used, followed by staining with PE-labeled rabbit anti-scFv antibodies and FACS analysis (FIG. 7c).

FIG. 14: This figure is the amino acid SEQ ID NO:203.

DETAILED DESCRIPTION OF THE INVENTION

Figure 1:
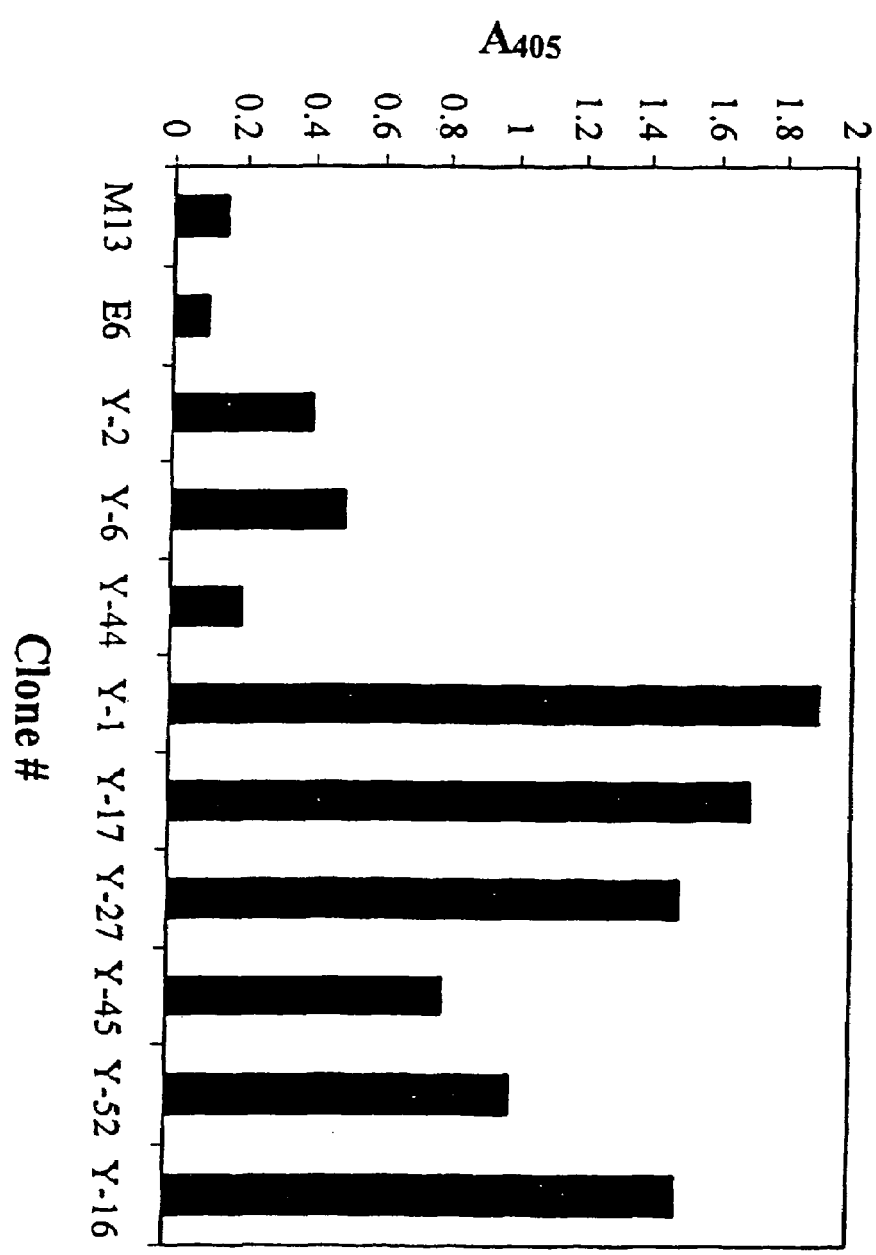
FIG. 1 presents phage clone binding to fixed platelets, as determined by the EIA assay. Data are presented as a function of absorbance at 405 nm.
Figure 2:
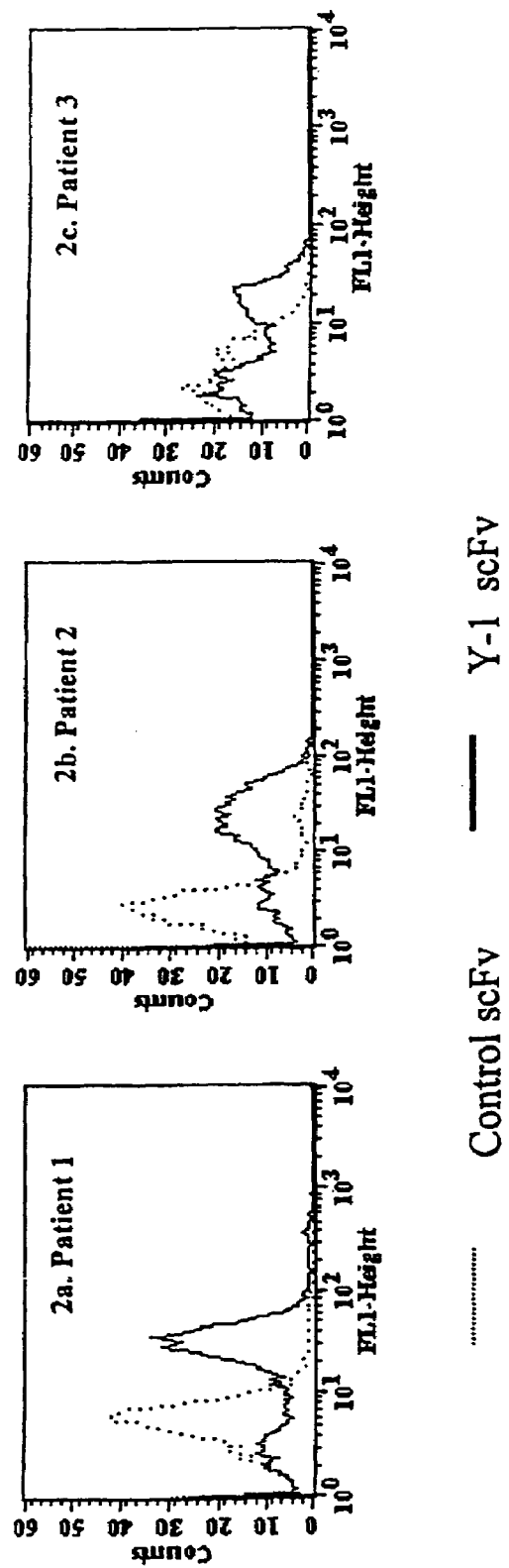
FIGS. 2a, 2b and 2c present the binding of mononuclear cell samples obtained from three individual AML patients to scFvs, as determined by FACS analysis. Fluorescence intensity of cells bound by the two FITC-labeled tested samples (control scFv and scFv clone Y1) is presented.

Specificity is herein defined as the recognition, by one or more domains in the peptide or polypeptide of the invention, of a target ligand and subsequent binding thereto.

Selectivity is herein defined as the ability of a targeting molecule to choose and bind one cell type or cell state from a mixture of cell types or cell states, all cell types or cell states of which may be specific for the targeting molecule.

Conservative amino acid substitution is defined as a change in the amino acid composition by way of changing one or two amino acids of a peptide, polypeptide or protein, or fragment thereof. The substitution is of amino acids with generally similar properties (e.g., acidic, basic, aromatic, size, positively or negatively charged, polar, non-polar) such that the substitutions do not substantially in a major way alter peptide, polypeptide or protein characteristics (e.g., charge, isoelectric point, affinity, avidity, confonnation, solubility) or activity. Typical substitutions that may be performed for such conservative amino acid substitution may be among the groups of amino acids as follows:

(i) glycine (G), alanine (A), valine (V), leucine (L) and isoleucine (I)
(ii) aspartic acid (D) and glutamic acid (E)
(iii) alanine (A), serine (S) and threonine (T)
(iv) histidine (H), lysine (K) and arginine (R)
(v) asparagine (N) and glutamine (Q)
(vi) phenylalanine (F), tyrosine (Y) and tryptophan (W)

Conservative amino acid substitutions can be made in, as well as, flanking the hypervariable regions primarily responsible for the selective and/or specific binding characteristics of the molecule, as well as other parts of the molecule, e.g., variable heavy chain cassette. Additionally or alternatively, modification can be accomplished by reconstructing the molecules to form full-size antibodies, diabodies (dimers), triabodies (timers) and/or tetrabodies (tetramers) or to form minibodies or microbodies.

As used herein in the specification and in the claims, an Fv is defined as a molecule that is made up of a variable region of a heavy chain of a human antibody and a variable region of a light chain of a human antibody, which may be the same or different, and in which the variable region of the heavy chain is connected, linked, fused or covalently attached to, or associated with, the variable region of the light chain.

A fragment of an Fv molecule is defined as any molecule smaller than the original Fv that still retains the selective and/or specific binding characteristics of the original Fv. Examples of such fragments include but are limited to (1) a minibody, which comprises a fragment of the heavy chain only of the Fv, (2) a microbody, which comprises a small fractional unit of antibody heavy chain variable region (PCT Application No. PCT/IL99/00581), (3) similar bodies comprising a fragment of the light chain, and (4) similar bodies comprising a functional unit of a light chain variable region.

An anti-cancer agent is an agent with anti-cancer activity, i.e., any activity that inhibits the growth or differentiation of cancerous or immature pre-cancerous cells, or any activity that inhibits metastasis of cancerous cells. In the present invention, an anti-cancer agent is also an agent with anti-angiogenic activity that prevents, inhibits, retards or halts angiogenesis of tumor tissue or is also an agent with anti-adhesion acitivities that inhibits, retards or halts adhesion and metastatic invastion of cancerous and pre-cancerous cells.

Inhibition of growth of a cancer cell is herein defined as the (i) prevention of cancerous or metastatic growth, (ii) slowing down of the cancerous or metastatic growth, (iii) the total prevention of the growth process of the cancer cell or the metastatic process, while leaving the cell intact and alive, or (iv) killing the cancer cell. More specifically, inhibition of cancerous growth can be applied especially against blood-related cancers, e.g., AML, multiple myeloma, or chronic lymphatic leukemia.

A phagemid is defined as a phage particle that carries plasmid DNA. Because it carries plasmid DNA, the phagemid particle does not have sufficient space to contain the full complement of the phage genome. The component that is missing from the phage genome is information essential for packaging the phage particle. In order to propagate the phage, therefore, it is necessary to culture the desired phage particles together with a helper phage strain that complements the missing packaging information.

A cassette, as applied to polypeptides and as defined in the present invention, refers to a given sequence of consecutive amino acids that serves as a framework and is considered a single unit and is manipulated as such. Amino acids can be replaced, inserted into, removed, or attached at one or both ends. Likewise, stretches of amino acids can be replaced, inserted into, removed or attached at one or both ends.

As used herein, an immunoglobulin (Ig) molecule is defined as any one of five classes, i.e., IgG, IgA, IgD, IgE, or IgM. The IgG class encompasses several sub-classes including, but not restricted to, IgG1, IgG2, IgG3, and IgG4.

A pharmaceutical composition refers to a formulation which comprises a peptide or polypeptide of the invention and a pharmaceutically acceptable carrier, excipient or diluent thereof.

A pharmaceutical agent refers to an agent that is useful in the prophylactic treatment or diagnosis of a mammal including, but not restricted to, a human, bovine, equine, porcine, murine, canine, feline, or any other warm-blooded animal. The pharmaceutical agent is selected from the group comprising radioisotope, toxin, oligonucleotide, recombinant protein, antibody fragment, and anti-cancer agent. Examples of such pharmaceutical agents include, but are not limited to anti-viral agents including acyclovir, ganciclovir and zidovudine; anti-thrombosis/restenosis agents including cilostazol, dalteparin sodium, reviparin sodium, and aspirin; anti-inflammatory agents including zaltoprofen, pranoprofen, droxicam, acetyl salicylic 17, diclofenac, ibuprofen, dexibuprofen, sulindac, naproxen, amtolmetin, celecoxib, indomethacin, rofecoxib, and nimesulid; anti-autoimmune agents including leflunomide, denileukin diftitox, subreum, WinRho SDF, defibrotide, and cyclophosphamide; and anti-adhesion/anti-aggregation agents including limaprost, clorcromene, and hyaluronic acid.

An anti-leukemia agent is an agent with anti-leukemia activity. For example, anti-leukemia agents include agents that inhibit or halt the growth of leukemic or immature pre-leukemic cells, agents that kill leukemic or pre-leukemic cells, agents that increase the susceptibility of leukemic or pre-leukemic cells to other anti-leukemia agents, and agents that inhibit metastasis of leukemic cells. In the present invention, an anti-leukemia agent may also be agent with anti-angiogenic activity that prevents, inhibits, retards or halts vascularization of tumors.

The term "affinity" as used herein is a measure of the binding strength (association constant) between a receptor (e.g., one binding site on an antibody) and a ligand (e.g., antigenic determinant). The strength of the sum total of noncovalent interactions between a single antigen-binding site on an antibody and a single epitope is the affinity of the antibody for that epitope. Low affinity antibodies bind antigen weakly and tend to dissociate readily, whereas high-affinity antibodies bind antigen more tightly and remain bound longer. The term "avidity" differs from affinity because the former reflects the valence of the antigen-antibody interaction.

Specificity of antibody-antigen interaction: Although the antigen-antibody reaction is specific, in some cases antibody elicited by one antigen can cross-react with another unrelated antigen. Such cross-reactions occur if two different antigens share an homologous or similar epitope or an anchor region thereof or if antibodies specific for one epitope bind to an unrelated epitope possessing similar chemical properties.

Blast cells are cells in an immature stage of cellular development distiguished by a higher cytoplasm-to-nucleus ratio than a resting cell.

A platelet is a disc like cytoplasmic fragment of a megakaryocyte that is shed in the marrow sinus and subsequently are circulating in the peripheral blood stream. Platelets have several physiological functions including a major role in clotting. A platelet contains granules in the central part and peripherally, clear protoplasm, but no definite nucleus.

The term "epitope" is used herein to mean the antigenic determinant or antigen site that interacts with an antibody, antibody fragment, antibody complex or a complex comprising a binding fragment thereof or T-cell receptor. The term epitope is used interchangeably herein with the terms ligand, domain, and binding region.

A given cell may express on its surface a protein having a binding site (or epitope) for a given antibody, but that binding site may exist in a cryptic form (e.g., be sterically hindered or be blocked, or lack features needed for binding by the antibody) in the cell in a state, which may be called a first stage (stage I). Stage I may be, for example, a normal, healthy, non-diseased status. When the epitope exists in cryptic form, it is not recognized by the given antibody, i.e., there is no binding of the antibody to this epitope or to the given cell at stage I. However, the epitope may be exposed by, e.g., undergoing modifications itself, or being unblocked because nearby or associated molecules are modified or because a region undergoes a conformational change. Examples of modifications include changes in folding, changes in post-translational modifications, changes in phospholipidation, changes in sulfation, changes in glycosylation, and the like. Such modifications may occur when the cell enters a different state, which may be called a second stage (stage II). Examples of second states, or stages, include activation, proliferation, transformation, or in a malignant status. Upon being modified, the epitope may then be exposed, and the antibody may bind.

As used herein the term "Fab fragment" is a monovalent antigen-binding fragment of an immunoglobulin. A Fab fragment is composed of the light chain and part of the heavy chain.

Polyclonal antibodies are the product of an immune response and are formed by a number of different B-lymphocytes. Monoclonal antibodies are derived from a single cell.

Agglutination as used herein means the process by which suspended bacteria, cells, discs, or other particles of similar size are caused to adhere and form into clumps. The process is similar to precipitation but the particles are larger and are in suspension rather than being in solution.

The term aggregation means the clumping of platelets induced in vitro, and thrombin and collagen, as part of a sequential mechanims leading to the formation of a thrombus or hemostatic plug.

The expression pattern of a gene can be studied by analyzing the amount of gene product produced under various conditions, at specific times, in various tissues, etc. A gene is considered to be "over expressed" when the amount of gene product is higher than that found in a normal control, e.g., non-diseased control.

A promoter is a region on DNA at which RNA polymerase binds and initiates transcription.

Antibodies, or immunoglobulins, are protein molecules that bind to antigen. They are composed of units of four polypeptide chains (2 heavy and 2 light) linked together by disulfide bonds. Each of the chains has a constant and variable region. They can be divided into five classes, IgG, IgM. IgA, IgD, and IgE, based on their heavy chain component. They are produced by B lymphocytes and recognize a particular foreign antigenic determinant and facilitate clearing of that antigen.

Antibodies may be produced and used in many forms, including antibody complexes. As used herein, the term "antibody complex" or "antibody complexes" is used to mean a complex of one or more antibodies with another antibody or with an antibody fragment or fragments, or a complex of two or more antibody fragments.

F(ab')2 fragment is a bivalent antigen binding fragment of an immunoglobulin obtained by pepsin digestion. It contains both light chains and part of both heavy chains.

Fc fragment is a non-antigen-binding portion of an immunoglobulin. It contains the carboxy-terminal portion of heavy chains and the binding sites for the Fc receptor.

Fd fragment is the variable region and first constant region of the heavy chain of an immunoglobulin.

Contaminating proteins are those proteins that are not specifically being selected for and which may be present in a sample.

Peptido-mimetics are small molecules, peptides, polypeptides, lipids, polysaccharides or conjugates thereof that have the same functional effect or activity of another entity such as an antibody.

Phagemids are plasmid vectors designed to contain an origin of replication from a filamentous phage, such as M13 or fd.

A wide spectrum of diseases exists that involves diseased, altered, or otherwise modified cells that express cell-specific and/or disease-specific ligands on their surfaces. These ligands can be utilized to effect recognition, selection, diagnosis and treatment of specific diseases through recognition, selection, diagnosis and treatment of each individual cell. The subject invention provides for peptides or polypeptides that comprise an Fv molecule, a construct thereof, a fragment thereof, a construct of a fragment thereof, or a fragment of a construct, all of which have enhanced binding characteristics. These binding characteristics allow the peptide or polypeptide molecule to bind selectively and/or specifically to a target cell in favor of other cells, the binding specificity and/or selectivity being primarily determined by a first hypervariable region. The Fv can be a scFv or a dsFv.

The Fv molecule described above can be used to target the diseased cell. The diseased cell can be, for example, a cancer cell. Examples of types of cancer that are amenable to diagnosis and/or treatment by specific targeting include, but are not limited to, carcinoma, sarcoma, leukemia, adenoma, lymphoma, myeloma, blastoma, seminoma, and melanoma. Leukemia, lymphoma, and myeloma are cancers that originate in the bone marrow and lymphatic tissues and are involved in uncontrolled growth of cells.

New approaches for diagnosing and treating diseases, particularly cancer, have been developed in recent years. Among them is the tumor targeting approach, using targeting molecules that can be selected and produced in a variety of ways. One approach for identifying possible targeting molecules is phage display. Phage display is a technique in which peptides, polypeptides, antibodies or proteins are generated and selected by their expression and display on the surface of a filamentous bacteriophage by fusion to a phage coat protein, with the DNA encoding the displayed protein residing within the phage virion. The scFv that is produced by the phage display technique is comprised of the variable domains of each of the antibody heavy and light chains, linked by a flexible amino-acid polypeptide spacer (Nissim et al., EMBO J. 13, 692–698 (1994)).

A phage display library (also termed phage peptide/antibody library, phage library, or peptide/antibody library) comprises a large population of phage (generally $10^8$–$10^9$), each phage particle displaying a different peptide or polypeptide sequence. These peptide or polypeptide fragments may constructed to be of variable length. The displayed peptide or polypeptide can be derived from, but need not be limited to, human antibody heavy or light chains.

In the present invention, an scfv antibody library produced by the phage display technique was utilized to obtain and produce targeting molecules. Flow cytometry, particularly fluorescence-activated cell sorting ("FACS"), was used for identifying and isolating specific phage clones, the peptide or polypeptide of which recognizes target cells. Phage-expressed scFv antibody fragments are amenable to in vitro screening, enrichment and selection of high affinity clones (U.S. Pat. Nos. 5,821,337; 5,720,954). Thus, a library of this type offers a powerful means for generating new tools for research and clinical applications, and has numerous advantages over the conventional approach (Caron et al., Cancer Supplement, 73, 1049–1056 (1994)). The library contains the potential for a high diversity of antibody molecules (Nissim et al., EMBO J., 692–69 8 (1994)). In the present instance, stable human cDNA can be used as a continuous source of material for antibody production (U.S. Pat. No. 5,843,439). Molecule recognition and selection are not influenced by the in vivo immunogenicity of candidate target proteins.

While affinity selection of phage displayed antibodies provides a useful method for enriching antigen-reactive scFvs from large libraries, it requires multiple steps to isolate a single clone and to characterize soluble scFv. The scFvs themselves can be modified to improve their affinities and/or avidity by performing conservative amino acid substitutions, or by producing fragments of the scFv, or constructs of said fragments.

The scFvs of the subject invention, specific for different human cells and tissues, can be associated with, combined, fused or linked to various pharmaceutical agents and/or radioactive isotopes in a pharmaceutically effective amount with, optionally, a pharmaceutically effective carrier, to form drug-peptide compositions, fusions or conjugates having anti-disease and/or anti-cancer activity, and/or for diagnostic purposes thereof.

Phage clones are selected by and identified through a multi-step procedure known as biopanning. Biopanning is carried out by incubating phage displaying protein ligand variants (a phage display library) with a target, removing unbound phage by a washing technique, and specifically eluting the bound phage. The eluted phage are optionally amplified before being taken through additional cycles of binding and optional amplification that enriches the pool of specific sequences in favor of those phage clones bearing antibody fragments that display the best binding to the target. After several rounds, individual phage clones are characterized, and the sequences of the peptides displayed by the clones are determined by sequencing the corresponding DNA of the phage virion.

The scfv obtained in this manner is also referred to a lead compound. A lead compound is defined as a compound, the final format of which comprises a core peptide or polypeptide. The lead compound can be modified and/or expanded, but it must retain the core peptide or polypeptide or some conservatively modified form thereof. Modifications by way of amino acid substitution can be made at the N-terminus, at the carboxy terminus, or in any of the CDR regions of an Fv or in the regions upstream or downstream thereof, for example. Modifications also include but are not limited to, fused proteins, coupling to drugs or toxins, construction of multimers, and expansion to full antibody molecules. One preferred category of lead compound, as provided for in the present patent, is an scFv obtained as the final product of the biopanning procedure.

An embodiment of the invention provides for at least one non-natural modification of the peptide or polypeptide of the invention. The non-natural modification can render the peptide or polypeptide more immunogenic or more stable. Non-natural modifications include, but are not limited to peptoid modification, semipeptoid modification, cyclic peptide modification, N-terminus modification, C-terminus modification, peptide bond modification, backbone modification, and residue modification.

The selection of antigen-specific phage antibodies has largely relied on biopanning against an immobilized single antigen. There has been limited selection using whole cells as a target. In the present invention, whole cells were used to select specific antibodies that recognize leukemia cell surface determinants, wherein the specific receptor was not previously known or characterized. This method does not permit facile adjustment of antigen concentration or the removal of undesired dominant antibody reactivities. Additionally, the phage may enrich for those that display multiple copies of scFv, as opposed to those with higher affinity clones. Nevertheless, the advantages of this approach make it an invaluable tool for isolating novel human antibody molecules.

An embodiment of the invention provides for a peptide or polypeptide comprising an Fv molecule, a construct thereof, a fragment of either or a construct of a fragment that binds to an unknown ligand on a first cell having a first and a second state, wherein the binding is effective in the second state but not substantially in the first state and, by virtue of immuno-cross-reactivity, binds specifically or selectively to a ligand on a second cell, and wherein the Fv is a scFv or a dsFv, and optionally having one or more tags.

A further embodiment provides for the peptide or polypeptide of the invention, wherein the selective and/or specific binding of the peptide or polypeptide to the ligand of the second cell is determined primarily by a first hypervariable region.

A yet further embodiment provides for the peptide or polypeptide of the invention, wherein the first hypervariable region is a CDR3 region having an amino acid sequence selected from the group consisting of SEQ ID NOs:8–24.

A yet further embodiment provides for the peptide or polypeptide of the invention, wherein the first hypervariable region is a CDR3 region having an amino acid sequence selected from the group consisting of SEQ ID NOs:8–24, and wherein the binding selectivity or specificity is secondarily influenced by a second hypervariable region and/or by a third hypervariable region and/or by one or more of the upstream and/or by one or more of the downstream regions flanking the first, the second and the third hypervariable regions, respectively.

A further embodiment provides for the ligand of the second cell bound by the peptide or polypeptide of the invention. One such two-cell selection protocol was based on the following: Megakaryocytes are large multinucleated cells derived from hematopoietic stem cells in the bone marrow. Platelets break off the megakaryocyte cytoplasm and enter the peripheral blood. In vitro, a wide range of cytokines directly affects stem cells. For example, thrombopoietin increases platelet count by directly increasing the differentiation of stem cells into megakaryocytes. Thus, these cells express several cell surface markers that are also found in premature cells.

Malignant blood cells (leukemia and lymphoma) are characterized as immature cells that express cell surface proteins normally found in partially differentiated hematopoietic progenitors. Thus, platelets are an attractive source for the identification of premature cell surface markers expressed on diseased or malignant blood cells. In one protocol discussed below, specific cells such as, but not limited to platelets, carrying unknown ligands, were used for initial biopanning steps. Subsequent clone selection was performed with a desired target cell, of which the targeted cell surface markers are unknown, such as but not limited to AML cells. In this method, phage clones obtained by biopanning on platelets can provide tools for recognizing and binding to ligands on diseased or malignant blood cells of interest.

The target as described above includes cells derived from an isolated tissue. The isolated tissue can be a diseased tissue and, more specifically, a cancer tissue. Cancer tissue can be derived from any form of malignancy including, but not limited to, carcinoma, sarcoma, leukemia, adenoma, lymphoma, myeloma, blastoma, seminoma, and melanoma.

In addition to the biopanning method described above, another approach is based on isolation of a peptide or polypeptide that binds a ligand on a cell as determined by direct panning on that ligand.

The present invention provides for a peptide or polypeptide comprising an Fv molecule, a construct thereof, a fragment of either, or a construct of a fragment. A construct may be a multimer (e.g., diabody, triabody, tetrabody) or a full-size Ig molecule; a fragment might be a minibody or a microbody. All derived constructs and fragments retain enhanced binding characteristics so as to bind selectively and/or specifically to a target cell in favor of other cells. The binding selectivity and/or specificity is primarily determined by a first hypervariable region, and wherein the Fv is a scFv or a dsFv, and optionally having one or more tags.

In one embodiment of the invention, a tag is inserted or attached to the Fv peptide or polypeptide to aid in the preparation and identification thereof, and in diagnostics. The tag can later be removed from the molecule. The tag may be, but is not limited to, the following tags: AU1, AU5, BTag, c-myc, FLAG, Glu-Glu, HA, His6 (SEQ ID NO: 204), HSV, HTTPHH (SEQ ID NO: 205), IRS, KT3, Protein C, S-TAG®, T7, V5, VSV-G (Jarvik and Telmer, *Ann. Rev. Gen.*, 32, 601–618 (1998)), and KAK (lysine-alanine-lysine) (SEQ ID NO: 238). The tag is preferably c-myc or KAK (SEQ ID NO: 238).

The two variable chains of the Fv molecule of the present invention may be connected or linked together by a spacer of 0–20 amino acid residues in length. The spacer may be branched or unbranched. Preferably, the linker is 0–15 amino acid residues, and most preferably the linker is (Gly$_4$Ser)$_3$ (SEQ ID NO: 206) to yield a single chain Fv ("scFv"). The scFv is obtainable from a phage display library.

The Fv molecule itself is comprised of a first chain and a second chain, each chain comprising a first, second and third hypervariable region. The hypervariable loops within the variable domains of the light and heavy chains are termed Complementary Determining Regions (CDR). There are CDR1, CDR2 and CDR3 regions in each of the heavy and light chains. These regions are believed to form the antigen binding site and can be specifically modified to yield enhanced binding activity. The most variable of these regions in nature being the CDR3 region of the heavy chain. The CDR3 region is understood to be the most exposed region of the Ig molecule and as shown and provided herein is the site primarily responsible for the selective and/or specific binding characteristics observed.

An embodiment of the invention provides for a peptide or polypeptide comprising an Fv molecule, a construct thereof, a fragment of either, or a construct of a fragment having enhanced binding characteristics so as to bind selectively and/or specifically to a substantially exposed and/or overexpressed binding site on or in a target comprising a cell in favor of other cells on or in which the binding site is not substantially available and/or expressed, wherein the binding selectivity or specificity is primarily determined by a first hypervariable region, and wherein the Fv is a scFv or a dsFv, and optionally having one or more tags.

A further embodiment of the invention provides for a peptide or polypeptide wherein the first hypervariable region is a CDR3 region having an amino acid sequence selected from the group consisting of SEQ ID NOs:8–24.

A yet further embodiment provides for the peptide or polypeptide of the invention, wherein the first hypervariable region is a CDR3 region having an amino acid sequence selected from the group consisting of SEQ ID NOs:8–24, and wherein the binding selectivity or specificity is secondarily influenced by a second hypervariable region and/or by a third hypervariable region and/or by one or more of the upstream regions and/or by one or more of the downstream regions flanking the first, the second and the third hypervariable regions, respectively, wherein the second and third hypervariable regions are a CDR2 and a CDR1 region, respectively.

An embodiment of the invention provides for peptide or polypeptide that binds to a target cell that is an activated, excited, modified, changed, disturbed or diseased cell. A further embodiment of the invention provides for the target cell being a cancer cell. The target cell can be selected from the group comprised of, but is not limited to, carcinoma, sarcoma, leukemia, adenoma, lymphoma, myeloma, blastoma, seminoma, and melanoma. In a preferred embodiment, the cancer cell is a leukemia cell. In a most preferred embodiment, the leukemia cell is an AML cell.

The peptide or polypeptide of the present invention is also any construct or modified construct of the Fv that retains one or more of the hypervariable regions of the heavy and/or light chains and has selective and/or specific binding characteristics. Construct or modified construct includes, but is not limited to, scfv, dsFv, multimers of scFv such as dimers, trimers, tetramers and the like (also referred to as diabody, triabody, tetrabody), and full antibody, and any other multimer that can be constructed thereof, and that incorporates one or more of the hypervariable domains of the antibody. The peptide or polypeptide of the present invention is also a fragment of any construct or modified construct having some or all of the binding characteristics of the original construct.

The peptide or polypeptide of the present invention is also a construct of a fragment having some or all of the selective and/or specific binding characteristics of the original construct. Fvs herein described selectively and/or specifically bind to target cells and can be associated with, or conjugated to, anti-cancer agents or anti-disease agents.

Peptides, polypeptides, fragments thereof, constructs thereof and fragments of constructs thereof of Fv molecules of the invention can be prepared in either prokaryotic or eukaryotic expression systems. In one embodiment of the invention, the eukaryotic expression system is a mammalian system, and the peptide or polypeptide produced in the mammalian expression system, after purification, is substantially free of mammalian contaminants. A eukaryotic cell system, as defined in the present invention refers to an expression system for producing peptides or polypeptides by genetic engineering methods, wherein the host cell is a eukaryote. In another embodiment of the invention, a prokaryotic system for production of the peptide or polypeptide of the invention uses *E. coli* as the host for the expression vector. The peptide or polypeptide produced in the *E. coli* system, after purification, is substantially free of *E. coli* contaminating proteins. Use of a prokaryotic expression system may result in the addition of a methionine residue to the N-terminus of some or all of the sequences provided for in the present invention. Removal of the N-terminal methionine residue after peptide or polypeptide production to allow for full expression of the peptide or polypeptide can be performed by methods commonly known in the art, such as, but not limited to, the use of Aeromonas aminopeptidase under suitable conditions (U.S. Pat. No. 5,763,215).

The subject invention provides for production of a scFv based on the Fv peptide of the invention. Promoters incorporated into the vectors used for the cloning and amplification of the scFv in prokaryotic cells can be chosen from a wide selection. A promoter is a DNA sequence that is situated upstream of structural genes and is capable of controlling the expression of genes. Promoters are found in the natural state in the chromosome(s) of the organism and can also be engineered into prokaryotic or eukaryotic expression vectors. Promoters engineered into specific loci on the desired DNA fragment provide for finely tuned and precisely controlled expression of the gene of interest. In the present invention, several promoters were used in constructs that include the gene coding for the Fv of choice. Promoters include, but are not limited to the following: deo, P1–P2, osmB, λP$_L$, β-lac-U5, SRα 5, and CMV early promoter. Deo is a double stranded DNA plasmid which, upon introduction into a. suitable *E. coli* host, renders the host capable of effecting expression of DNA encoding a desired naturally-occurring polypeptide or polypeptide analog thereof under the control of the constitutive *E. coli*-derived deoxyribonucleotide promoter, deo P1–P2. A fuller description is provided in U.S. Pat. No. 5,795,776 (Fischer, Aug. 18, 1998) and U.S. Pat. No. 5,945,304 (Fischer, Aug. 31, 1999).

Expression of the *E. coli* osmB promoter is regulated by osmotic pressure. Vectors carrying this promoter can be used to produce high levels of a wide variety of recombinant eukaryotic and prokaryotic polypeptides under control of the osmB promoter in an *E. coli* host. A fuller description is provided in U.S. Pat. No. 5,795,776 (Fischer, Aug. 18, 1998) and U.S. Pat. No. 5,945,304 (Fischer, Aug. 31, 1999).

$\lambda P_L$ is a thermoinducible λ bacteriophage promoter regulated by the thermolabile repressor $cI^{857}$. For A fuller discussion, see Hendrix et al. *Lambda II*, Cold Spring Harbor Laboratory (1983).

β-lac-U5 is a lacZ promoter (Gilbert and Muller-Hill, *PNAS (US)*, 58, 2415 (1967).

$SR_\alpha 5$ is a mammalian cDNA expression system composed of the simian virus 40 (SV40) early promoter and the R-U5 segment of the human T-cell leukemia virus type 1 long terminal repeat. This expression system is 1 or 2 orders of magnitude more active than the SV40 early promoter in a wide variety of cell types (Takebe et al, *Molecular and Cellular Biology*, 8, 466–472 (1988).

The human cytomegalovirus promoter, known as the CMV intermediate/early enhancer/promoter is most preferably used in the present invention to promote constitutive expression of clone DNA inserts in mammalian cells. The CMV promoter is described in Schmidt, E. V. et al., (1990) *Mol. Cell. Biol.*, 10, 4406, and is U.S. Pat. Nos. 5,168,062 and 5,385,839.

In a preferred embodiment of the invention, the promoter for induction of the phagemid system in prokaryotes is selected from a group comprising deo, osmB, $\lambda P_L$, β-lac-U5, and CMV promoters. In a more preferred embodiment of the invention, the β-lac-U5 promoter was used for induction of the phagemid system in *E. coli*. In a most preferred embodiment, the CMV promoter is used.

In an embodiment of the invention, a peptide or polypeptide of the subject invention comprises: (a) a leader sequence that is present only in the encoded sequence but is lacking in the mature protein; (b) a variable regions of a heavy chain of the order of 135–145 amino acids, including a first hypervariable region of 4–12 amino acids that is subject to modifications; (c) a spacer region of ≦20 amino acids that be shortened or eliminated; (d) variable region of a light chain that is also subject to specific modifications described herein followed by; (e) a tag sequence for follow up, that is optionally not present in the final injectable product. The spacer, being generally about 15 amino acid residues long in the scFv, allows the two variable chains (heavy and light) to fold into functional Fv domain. The functional Fv domain retains selective and/or specific enhanced binding activity.

In another embodiment, (d) above is followed by a tag sequence or label that can be used for conjugation, diagnostic and/or identification purposes. In this embodiment, the tag is designed to connect between the peptide or polypeptide of the invention and an agent for treatment or diagnosis of the target cell.

The spacer region of the scFv may be linear or branched, and is generally comprised of glycine and seine residues, in multiples of the formula $(Gly_4Ser)_n$, (SEQ ID NO: 233) and is generally between a total of 0–20 amino acids in length, preferably 0–15 amino acids long and linear. By changing the spacer length as appropriate, a variety of multimers can be obtained. In an embodiment of the invention, the spacer is 0–5 amino acids in length. In another embodiment, the spacer is <3 amino acids long (as detailed below).

An example of an amino acid sequence of a scFv molecule of the subject invention follows (SEQ ID NOS: 207 & 25, respectively):

```
      ATGAAATACCTATTGCCTACGGCAGCCGCTGGATTGTTATTACTCGCGGCCCAGCCGGCC
   1  M   K   Y   L   L   P   T   A   A   A   G   L   L   L   L   A   A   Q   P   A
      ------------------------------------------------------------
  61  ATGGCCGAGGTGCAGCTGGTGGAGTCTGGGGGAGGTGTGGTACGGCCTGGGGGGTCCCTG
  21  M   A   E   V   Q   L   V   E   S   G   G   G   V   V   R   P   G   G   S   L
      ------
 121  AGACTCTCCTGTGCAGCCTCTGGATTCACCTTTGATGATTATGGCATGAGCTGGGTCCGC
  41  R   L   S   C   A   A   S   G   F   T   F   D   D   Y   G   M   S   W   V   R
 181  CAAGCTCCAGGGAAGGGGCTGGAGTGGGTCTCTGGTATTAATTGGAATGGTGGTAGCACA
  61  Q   A   P   G   K   G   L   E   W   V   S   G   I   N   W   N   G   G   S   T
 241  GGTTATGCAGACTCTGTGAGGGGCCGATTCACCATCTCCAGAGACAACGCCAAGAACTCC
  81  G   Y   A   D   S   V   K   G   R   F   T   I   S   R   D   N   A   K   N   S
 301  CTGTATCTGCAAATGAACAGTCTGAGAGCCGAGGACCGGCCGGTGTATTACGTGGCAAGA
 101  L   Y   L   Q   M   N   S   L   R   A   E   D   T   A   V   Y   Y   C   A   R
 361  ATGAGGGCTCCTGTGATTTGGGCCCAAGTAACCCTGGTCACCGTGTCGAGAGTGGGAGGC
 121  M   R   A   P   V   I   W   G   Q   G   T   L   V   T   V   S   R   G   G   G
 421  GGTTCAGGCGGAGGTGGCTCTGGCGGTGGCGGATCGTCTGAGCTGACACAGGACCCTGCT
 141  G   S   G   G   G   S   G   G   G   G   S   S   E   L   T   Q   D   P   A
 481  GTGTCTGTGGCCTTGGGACAGACAGTCAGGATCACATGCCAAGGAGACAGCCTCAGAAGC
 161  V   S   V   A   L   G   Q   T   V   R   I   T   C   Q   G   D   S   L   R   S
 541  TATTATGCAAGCTGGTACCAGCAGAAGCAGGACCAGGCCCCTTGTCTTGTCATCATGGGT
 181  Y   Y   A   S   W   Y   Q   Q   K   P   G   Q   A   P   V   L   V   I   Y   G
 601  AAAAACAACCGGCCCTCAGGGATCCCAGACCGATTCTCTGGCTCCAGCTCAGGAAACACA
 201  K   N   N   R   P   S   G   I   P   D   R   F   S   G   S   S   S   G   N   T
 661  GCTTCCTTGACCATCACTGGGGCTCAGGCGGAAGATGAGGCTGACTATTACTGTAACTCC
 221  A   S   L   T   I   T   G   A   Q   A   E   D   E   A   D   Y   Y   C   N   S
 721  CGGGACAGCAGTGGTAACCATGTGGTATTCGGCGGAGGGACCAAGCTGACCGTCCTAGGT
 241  R   D   S   S   G   N   H   V   V   F   G   G   G   T   K   L   T   V   L   G
 781  GCGGCCGCAGAACAAAAACTCATCTCAGAAGAGGATCTGAATGGGGCCGCATAG
 261  A   A   A   E   Q   K   L   I   S   E   E   D   L   N   G   A   A
```

The leader sequence is underlined with a dashed line (amino acids 1–22). The $V_H$ region is encoded by the bolded amino acid sequence (amino acids 23–120 (SEQ ID NO: 61. This specific clone is derived from the germline $V_H$3-DP32; however, the germline of each clone is dependent on its particular origin (see below). The amino acid sequence enclosed in a box (amino acids 121–126) encodes the $V_H$-CDR3 sequence, the hypervariable region among all clones derived from this library. The spacer region joining the $V_H$ and the $V_L$ regions is a flexible polypeptide, encoded by amino acids shown by italics. Finally the $V_L$ region is presented (amino acids 154–260, SEQ ID NO: 234). The fused $V_L$ fragment in all the clones is derived from a single unmutated V gene of germline IGLV3SI, and is here followed by the c-myc tag, underlined with a wavy line (amind acids 264–277, SEQ ID NO: 236). The full amino acid sequence is identical to SEQ ID NO:25. The Y1-scFv lacking an N-terminal leader, the C-terminal linker and the C-terminal myc tag is at amino acids 21–260 and is SEQ ID NO: 235.

Repertoires of $V_H$ fragments (from 49 germlines) were first generated by PCR from rearranged V-genes of peripheral blood lymphocytes of non-immunized human (referred to as a "naive repertoire") by the supplier of the library. The origin (germline) of the $V_H$-sequence can be identified by a homology test (Blast search), using one of the following web sites:

The binding characteristics of an antibody can be optimized in one of several ways. One way of optimizing an antibody to obtain a higher binding affinity relative to the original lead-compound is based on replacing the amino acid residues in the lead-compound, to introduce higher variability, or to extend the sequence. For example, the entire original $V_L$ region can be replaced with a $V_L$ region from a different antibody subtype.

An additional way to optimize binding affinity is to construct a phagemid display mutagenesis library. In a phagemid display mutagenesis library, oligonucleotides are synthesized so that each amino acid of the core sequence within the $V_H$ and the $V_L$ CDR3 is independently substituted by any other amino acid, preferably in a conservative manner known in the art. The subject invention provides for a set of specific antibody scFv displayed on phage, wherein the displayed antibody fragments and the soluble antibody fragments that can be extracted from the phage virions have the same biological activity.

The phage display library used herein was constructed from peripheral blood lymphocytes of non-immunized human, and the Fv peptide was selected against previously uncharacterized and unpurified antigens on the surface of a target cell. As used herein, previously uncharacterized and unpurified antigens refer to ligands presented on the surface of cells that have not been identified, characterized, isolated or purified by biochemical or molecular means previous to the current work, and that are observed or predicted in the present work by virtue of the selective and/or specific binding to isolated antibody fragments observed.

The scFv of the present invention displays enhanced binding to a target cell. The enhanced binding is directed to specific surface markers. Specific surface markers are molecules that are sequestered in the cellular membrane and are accessible to circulating recognition molecules. The presence of surface markers allowed for the development of the phage display technology via the biopanning technology described herein. In the present invention specific surface markers are employed to characterize and differentiate among various cell types, as well as to serve as the binding site for Fvs in their various forms. A variety of hematopoietic cell types can be differentiated according to their characteristic surface markers and, similarly, diseased or cancerous cells display surface markers that are unique to their type and stage.

Selection of the scFv clone can be accomplished by two different biopanning strategies:
1. selection directly, by using the diseased or cancer cell as the target cell, and
2. step-wise selection, by using a first e.g., normal cell in a second, e.g., activated, excited, modified, changed, or disturbed state, whereby a binding site of the first cell in the second state comprises an unknown ligand that is substantially exposed or displayed. By virtue of immuno-cross-reactivity, the resulting clone may bind, after subsequent biopanning or selection steps, selectively and/or specifically to a novel and unknown ligand on a second cell. Following further optional amplification and subsequent purification, targeting molecules may be constructed from the recognition sites of the purified recognition molecules selective and/or specific for an unknown ligand on a second cell.

In one embodiment of the invention, the first cell may be a normal cell, the first state a non-activated state and the second state an activated, excited, modified, changed or disturbed state. The second cell in the step-wise selection may be a human cell. In another embodiment of the invention, the second cell in the step-wise selection is a diseased cell. In a more preferred embodiment, the second cell in the step-wise selection is a cancer cell such as, but not limited to, carcinoma, sarcoma, leukemia, adenoma, lymphoma, myeloma, blastoma, seminoma, and melanoma. In a more preferred embodiment, the second cell is a leukemia cell. In a most preferred embodiment, the second cell is an AML cell.

A more preferred embodiment of the invention provides for a peptide or polypeptide wherein the selective and/or specific binding of the peptide or polypeptide to the ligand of the second cell is determined primarily by a first hypervariable region. In a yet more preferred embodiment, the first hypervariable region is a CDR3 region having an amino acid sequence selected from the group consisting of SEQ ID Nos: 8–24.

In another embodiment of the present invention herein provides for the ligand of the second cell bound by the peptide or polypeptide of the invention. A further embodiment provides for any molecule that recognizes and binds the ligand bound by the peptide or polypeptide of the invention.

The enhanced binding to a cancer cell is most likely due to overexpression of the ligand and/or exposure of binding site in the cancer cell relative to expression in the normal cell. As used herein, the term overexpression of the ligand is defined as the expression of a gene or its product normally silent in the particular cell type and/or in a particular stage of the cell cycle, or of increased expression of a gene that is expressed at basal levels under normal, non-malignant conditions for that particular cell type.

In a more preferred embodiment of the invention, the target cell of the biopanning procedure is contained in a cell suspension. Hematopoietic cells are obtained in suspension, and biopanning may be carried out by mixing a phage library with a blood cell suspension, followed by washing with several buffers. Phage are extracted from the human cells, amplified, and the displayed antibody fragment sequence is determined.

In a yet more preferred embodiment of the invention, the blood cell suspension comprises leukemic cells. In a most preferred embodiment, the blood cell suspension comprises AML cells. In another embodiment of the subject invention, the target cell is derived from an isolated organ or part thereof.

In another embodiment of the subject invention, the target cell or the second cell is derived from a cell line. Cell lines can be cultured and manipulated such that they can aid in determination of the binding characteristics of the Fv clones. In addition, cell lines can be useful in the development of diagnostic kits.

In a preferred embodiment, the cell line is a hematopoietic cell line, such as but not limited to the following lines: Jurkat, Molt-4, HS-602, U937, TF-I, THP-1, KG-1, ML-2, and HUT-78 cell lines.

In a preferred embodiment of the invention the CDR3 region is built, inserted, coupled or fused into or onto any one of 84 cassettes (SEQ ID NOs:30–113). In a more preferred embodiment, the CDR3 region is built, inserted, coupled or fused into or onto any one of 49 cassettes (SEQ ID NOs:30–32, 35, 37–39, 41, 43, 45, 46, 48, 51, 54, 57, 59–68, 70, 71, 76–85, 87, 89–92, 94, 97, 99, 103, 106, 112, and 113). In a most preferred embodiment, the CDR3 region is built, inserted, coupled or fused to the C-terminus of cassette of SEQ ID NO:61, or any of the above sequences having at least 90% sequence similarity therewith.

In one embodiment, the amino acid sequence of the cassette is ostensibly fixed, whereas the replaced, inserted or attached sequence can be highly variable. The cassette can be comprised of several domains, each of which encompasses a function crucial to the final construct. The cassette of a particular embodiment of the present invention comprises, from the N-termmius, framework region 1 (FRI), CDRI, framework region 2 (FR2), CDR2, and framework region 3 (FR3).

In an embodiment of the invention, it is possible to replace distinct regions within the cassette. For example, the CDR2 and CDR1 hypervariable regions of the cassette may be replaced or modified by non-conservative or, preferably, conservative amino acid substitutions. More specifically, the CDR2 and CDR1 regions of a cassette of consecutive amino acids selected from the group comprising of SEQ ID NOs: 30–113 or a fragment thereof can be replaced by SEQ ID NOs:115 and 114, respectively. Even more specifically, the CDR2 and CDR1 regions of a cassette of consecutive amino acids selected from the group comprising of SEQ ID NOs: 30–32, 35, 37–39, 41, 43, 45, 46, 48, 51, 54, 57, 59–68, 70, 71, 76–85, 87, 89–92, 94, 97, 99, 103, 106, 112, and 113 or fragment thereof can be replaced by SEQ ID NOs:115 and 114, respectively.

In a preferred embodiment of the invention, the peptide or polypeptide comprises a heavy and a light chain, and each chain comprises a first, second and third hypervariable region which are the CDR3, CDR2 and CDR1 regions, respectively. The binding selectivity and specificity are determined particularly by the CDR3 region of a chain, possibly by the CDR3 region of the light chain and, preferably, by the CDR3 region of the heavy chain, and secondarily by the CDR2 and CDR1 regions of the light chain and, preferably, of the heavy chain. The binding selectivity and specificity may also be secondarily influenced by the upstream or downstream regions flanking the first, second, and/or third hypervariable regions.

In a preferred embodiment, the CDR3 region of the peptide or polypeptide has an amino acid sequence selected from the group comprising SEQ ID NOs:8–24.

In a more preferred embodiment, the CDR3 region of the heavy chain has an amino acid sequence selected from the group comprising SEQ ID NOs:8–24, the CDR2 has an amino acid sequence identical to SEQ ID NO:115, and the CDR1 region has an amino acid sequence identical to SEQ ID NO: 114.

In a most preferred embodiment of the invention, the CDR3 region has an amino acid sequence identical to SEQ ID NO:8.

In addition to the heavy and light chain, the Fv comprises a flexible spacer of 0–20 amino acid residues. The spacer can be a branched chain or a straight chain. Two possible sequences of the spacer are identical to SEQ ID NOs: 123 and 124.

A preferred embodiment of the invention is a scFv with a CDR3 sequence identical to SEQ ID NO: 8 and a full scFv sequence identical to SEQ ID NO: 25.

Another preferred embodiment of the invention is a scFv with a CDR3 sequence identical to SEQ ID NO: 20 and a full scFv sequence identical to SEQ ID NO 203.

In a most preferred embodiment of the invention the CDR3, CDR2 and CDR1 regions have the amino acid SEQ ID NOs:8, 115 and 114, respectively.

In an embodiment of the invention, the Fv peptide comprises a CDR1 and CDR2 region of the variable heavy chain, which itself comprises a cassette with an amino acid sequence selected from the group comprising SEQ ID NOs:30–113; a CDR3 region, preferably of the variable heavy chain, which has an amino acid sequence selected from the group comprising SEQ ID NO: 8–24; an upstream region flanking the CDR3 region which has the amino acid sequence of SEQ ID NO: 117; a downstream region flanking the CDR3 region which has the amino acid sequence of SEQ ID NO:116; a spacer of 0–20 amino acid residues of SEQ ID NO:123 or 124; a variable light chain region the sequence of which is SEQ ID NO:7.

Similarly, in another embodiment the upstream region flanking the CDR2 region has the amino acid sequence of SEQ ID NO:119, the downstream region flanking the CDR2 region has the amino acid sequence of SEQ ID NO:118, the upstream region flanking the CDR1 region has the amino acid sequence of SEQ ID NO:121 and the downstream region flanking the CDR1 region has the amino acid sequence of SEQ ID NO:120.

A preferred embodiment of the invention provides for a peptide or polypeptide wherein the second and third hypervariable regions are a CDR2 and a CDR1 hypervariable region, respectively and wherein the CDR3 amino acid sequence is SEQ ID NO:8, wherein the CDR2 amino acid sequence is SEQ ID NO:115, wherein the CDR1 amino acid sequence is SEQ ID NO:114, wherein the upstream region flanking the CDR3 region has the amino acid sequence of SEQ ID NO:117, wherein the downstream region flanking the CDR3 region has the amino acid sequence of SEQ ID NO:116, wherein the upstream region flanking the CDR2 region has the amino acid sequence of SEQ ID NO: 119, wherein the downstream region flanking the CDR2 region has the amino acid sequence of SEQ ID NO: 118, wherein the upstream region flanking the CDR1 region has the amino acid sequence of SEQ ID NO: 121 and wherein the downstream region flanking the CDR1 region has the amino acid sequence of SEQ ID NO:120.

Another preferred embodiment of the invention provides for an Fv molecule that comprises a first chain having a first, a second and a third hypervariable region and a second chain having a first, a second and a third hypervariable region, wherein one of the hypervariable regions of the first chain has a sequence selected from the group consisting of SEQ ID NOs:8–24, and wherein one of the hypervariable regions of the second chain has a sequence selected from the group consisting of SEQ ID NOs:1–6 and 125–202, and wherein the first, second and third hypervariable regions are a CDR3, CDR2 and CDR1 region, respectively and wherein the Fv is a scFv or a dsFv, and optionally having one or more tags.

Another embodiment of the invention provides for a peptide or polypeptide (i) wherein the first chain and the second chain each comprises a first hypervariable region selected from the group consisting of SEQ ID NOs:8–24; or (ii) wherein the first hypervariable region of the first and second chains are identical and selected from the group consisting of SEQ ID NOs:8–24; or (iii) wherein the first hypervariable region of the first chain is selected from the group consisting of SEQ ID NOs:8–24, and the first hypervariable region of the second chain is selected from the group consisting of SEQ ID NOs:1–6 and 125–202; or (iv) wherein the first hypervariable region of the first chain is selected from the group consisting of SEQ ID NOs:1–6 and 125–202, and the first hypervariable region of the second chain is selected from the group consisting of SEQ ID NOs:8–24.

A further embodiment provides for the peptide or polypeptide of the invention wherein the second and third hypervariable regions of the first chain are SEQ ID NOs:114 and 115, respectively.

For all the amino acid sequences of $\leq 25$ amino acid residues described and detailed herein (e.g., CDR regions, CDR flanking regions), it is to be understood and considered as a further embodiment of the invention that these amino acid sequences include within their scope one or two amino acid substitution(s) and that preferably the substitutions are conservative amino acid substitutions. For all the amino acid sequences of >25 amino acid residues described and detailed herein, it is to be understood and considered as an embodiment of the invention that these amino acid sequences include within their scope an amino acid sequence with $\geq 90\%$ sequence similarity to the original sequence (Altschul et al., *Nucleic Acids Res.*, 25, 3389–3402 (1997)). Similar or homologous amino acids are defined as non-identical amino acids which display similar properties, e.g., acidic, basic, aromatic, size, positively or negatively charged, polar, non-polar.

Percentage amino acid similarity or homology or sequence similarity is determined by comparing the amino acid sequences of two different peptides or polypeptides. The two sequences are aligned, usually by use of one of a variety of computer programs designed for the purpose, and amino acid residues at each position are compared. Amino acid identity or homology is then determined. An algorithm is then applied to determine the percentage amino acid similarity. It is generally preferable to compare amino acid sequences, due to the greatly increased sensitivity to detection of subtle relationships between the peptide, polypeptide or protein molecules. Protein comparison can take into account the presence of conservative amino acid substitutions, whereby a mismatch may yet yield a positive score if the non-identical amino acid has similar physical and/or chemical properties (Altschul et al., *Nucleic Acids Res.*, 25, 3389–3402 (1997).

In an embodiment of the invention the three hypervariable regions of each of the light and heavy chains can be interchanged between the two chains and among the three-hypervariable sites within and/or between chains.

One skilled in the art will realize that demonstration of specific and/or selective binding of the peptide or polypeptide of the invention necessitates the use of a suitable negative control. A suitable negative control may be a peptide or polypeptide, the amino acid sequence of which is almost identical to the peptide or polypeptide of the invention, with the only difference being in the hypervariable CDR3 region. Another suitable negative control may be a peptide or polypeptide that is the same size and/or general three-dimensional structure as the peptide or polypeptide of the invention but has a totally unrelated amino acid sequence. Another suitable negative control may be a peptide or polypeptide with completely different physical and chemical characteristics, when compared to the peptide or polypeptide of the invention. The negative controls used in the development of the present invention are designated N14, having a CDR3 sequence identical to SEQ ID NO:28, and C181, having a CDR3 sequence identical to SEQ ID NO:29. Other negative controls, however, may likewise be suitable.

Another embodiment provides for a nucleic acid molecule, preferably a DNA molecule, encoding the Fv peptide or polypeptide of the invention.

In a preferred embodiment of the invention, and in order to optimize the selective binding of the Fv, the CDR3 sequences that confers primary binding selectivity and/or specificity to the Fv may be moved to any other heavy chain germline. More particularly they may be moved to one of 84 possible heavy chain germlines. These 84 germlines (SEQ ID NOs:30–113) comprise (a) the germline in which the claimed phage clone was originally isolated, (b) 48 additional germlines available in the phage display library and (c) 35 alternative germlines claimed herein (Tomlinson et al, *J. Mol. Biol.*, 227(3):776–798 (1992)). The local linear, or 3-dimensional environment of the CDR3 region, in concert with the CDR3 region itself, may potentially play a role in guiding or encouraging the proper CDR3 binding. For example, peptides having any of the CDR3 sequences recited herein as SEQ ID NOs:8–24, 125 and derived from any of the 49 germline sequences (SEQ ID NOs:30–32, 35, 37–39, 41, 43, 45, 46, 48, 51, 54, 57, 59–68, 70, 71, 76–85, 87, 89–92, 94, 97, 99, 103, 106, 112, and 113) are also encompassed by the subject invention.

Germline DP-32 is the cassette for several clones of the present invention. The C-terminus of this germline has been replaced with a consensus sequence to aid in phage display library preparation. The seven carboxy-terminal amino acids of SEQ ED NO: 61 have been replaced by the seven amino acid sequence of SEQ ID NO: 122.

CDR3 regions of Fvs of the present invention may contain the core sequence $^{Arg}\!/_{Gly/Lys}$Phe Pro which binds specifically to AML cells. Eight examples of such CDR3 regions are presented in Table 2. Although the motif coincides with the three N-terminal amino acid residues of the CDR3 region in each case, it may also be located elsewhere in the CDR3 region. Alternatively, the motif is a binding motif that is used to build or construct an anchor or a binding region of part of a larger binding or targeting or recognition molecule or is used alone as a target vehicle.

In a further embodiment of the present invention there is provided a binding motif comprising the amino acid sequence of $R_1$-X Phe Pro-$R_2$ wherein $R_1$ and $R_2$ each comprises 0–15, preferably 1–9, amino acid residues and wherein X is either Arg, Gly or Lys. Most preferably, the CDR3 comprises the amino acid sequence of $R_1$-X Phe Pro-$R_2$, wherein $R_1$ and $R_2$ each comprises 0–15 amino acid residues, and wherein X is either Arg, Gly, or Lys.

In another preferred embodiment of the peptide or polypeptide of the subject invention, 1–1000 amino acids may be added either to the C-terminus or to the N-terminus of the peptide, while the peptide maintains its biological activity. In a preferred embodiment of the invention, 150–500 amino acids may be added either to the C-terminus or to the N-terminus of the peptide or polypeptide, while the peptide maintains its biological activity. In another preferred embodiment of the invention, 800–1000 amino acids may be added either to the C-terminus or the N-terminus of the peptide or polypeptide, while the peptide or polypeptide maintains its biological activity.

An example for extending the core amino-acid sequence is by building a full-sized immunoglobulin Ig, using a lead compound as the core of the Ig. The full-sized Ig may, for example, belong to the immunoglobulin class that can induce the endogenous cytolytic activity via complement or activation of cellular cytolytic activity (e.g., IgG1, IgG2, or IgG3). The full-sized Ig may belong to the immunoglobulin class of strongly binding antibodies (e.g., IgG4). On binding, the full-sized Ig may act in one or more of many ways, e.g., by acting as a flag for the body's defense mechanism to initiate an immune response, by tranducing intracellular cell signaling, or by causing damage to a target cell.

One preferred embodiment of the present invention provides for an Ig molecule expressed as a recombinant polypeptide and produced in a eukaryotic cell system. In a preferred embodiment of the invention, the Ig polypeptide is an IgG polypeptide and it is produced in a mammalian cell system. In a more preferred embodiment the mammalian cell system comprises the CMV promoter.

In a preferred embodiment of the invention, the IgG molecule comprises a CDR3, CDR2 and CDR1 hypervariable region, both in the light and in the heavy chains. In a more preferred embodiment of the invention, the Fv molecule comprises a CDR3, CDR2 and a CDR1 region having SEQ ID NOs:8, 115 and 114, respectively. The CDR3, CDR2 and CDR1 regions can be of the heavy chain or of the light chain.

A further preferred embodiment of the invention provides for an IgG molecule having a light chain with a sequence identical to SEQ ID NO: 27 and a heavy chain with a sequence identical to SEQ ID NO: 26, or a heavy chain and a light chain having at least 90% sequence similarity therewith. In a most preferred embodiment of the invention the two heavy chains of the IgG are identical and the two light chains of the IgG are identical.

In another embodiment, the peptide of the subject invention is constructed to fold into multivalent Fv forms.

The present invention provides for a Y1 or Y17 peptide or polypeptide comprising an scFv molecule. As used herein a scFv is defined as a molecule which is made up of a variable region of a heavy chain of a human antibody and a variable region of a light chain of a human antibody, which may be the same or different, and in which the variable region of the heavy chain is connected, linked, fused or covalently attached to, or associated with, the variable region of the light chain.

A Y1 and Y17 scFV construct may be a multimer (e.g., dimer, trimer, tetramer, and the like) of scFv molecules that incorporate one or more of the hypervariable domains of the Y1 or Y17 antibody. All scFv derived constructs and fragments retain enhanced binding characteristics so as to bind selectively and/or specifically to a target cell in favor of other cells. The binding selectivity and/or specificity is primarily determined by hypervariable regions.

The hypervariable loops within the variable domains of the light and heavy chains are termed Complementary Determining Regions (CDR). There are CDR1, CDR2 and CDR3 regions in each of the heavy and light chains. The most variable of these regions is the CDR3 region of the heavy chain. The CDR3 region is understood to be the most exposed region of the Ig molecule, and as provided herein, is the site primarily responsible for the selective and/or specific binding characteristics observed.

The Y1 and Y17 peptide of the subject invention can be constructed to fold into multivalent Fv forms. Y1 and Y17 multimeric forms were constructed to improve binding affinity and specificity and increased half-life in blood.

Mulitvalent forms of scFv have been produced by others. One approach has been to link two scFvs with linkers. Another approach involves using disulfide bonds between two scFvs for the linkage. The simplest approach to production of dimeric or trimeric Fv was reported by Holliger et al., *PNAS*, 90, 6444–6448 (1993) and A. Kortt, et al., *Protein Eng.*, 10, 423–433 (1997). One such method was designed to make dimers of scFvs by adding a sequence of the FOS and JUN protein region to form a leucine zipper between them at the c-terminus of the scFv. Kostelny S A et al., *J Immunol*. 1992 Mar 1;148(5):1547–53; De Kruif J et al., *J Biol Chem*. 1996 Mar 29;271(13):7630–4. Another method was designed to make tetramers by adding a streptavidin coding sequence at the c-terminus of the scFv. Streptavidin is composed of 4 subunits so when the scFv-streptavidin is folded, 4 subunits accommodate themselves to form a tetramer. Kipriyanov S M et al., *Hum Antibodies Hybridomas*, 1995;6(3):93–101. In yet another method, to make dimers, trimers and tetramers, a free cysteine is introduced in the protein of interest. A peptide-based cross linker with variable numbers (2 to 4) of maleimide groups was used to cross link the protein of interest to the free cysteines. Cochran J R et al., *Immunity*, 2000 Mar;12(3):241–50.

In this system, the phage library (as described herein above) was designed to display scFvs, which can fold into the monovalent form of the Fv region of an antibody. Further, and also discussed herein above, the construct is suitable for bacterial expression. The genetically engineered scFvs comprise heavy chain and light chain variable regions joined by a contiguously encoded 15 amino acid flexible peptide spacer. The preferred spacer is $(Gly_4Ser)_3$ (SEQ ID NO: 206). The length of this spacer, along with its amino acid constituents provides for a nonbulky spacer, which allows the $V_H$ and the $V_L$ regions to fold into a functional Fv domain that provides effective binding to its target.

The present invention is directed to Y1 and Y17 multimers prepared by any known method in the art. A preferred method of forming multimers, and especially dimers, employs the use of cysteine residues to form disulfide bonds between two monomers. In this embodiment, dimers are formed by adding a cysteine on the carboxyl terminus of the scFvs (referred to as Y1-cys scFv or Y1 dimer) in order to facilitate dimer formation. After the DNA construct was made (See Example 2D and 6D) and used for transfection, Y1 dimers were expressed in a production vector and refolded in vitro. The protein was analyzed by SDS-PAGE, HPLC, and FACS. Two-liter fermentation batches of the antibodies were run. After expressing Y1-cys in *E. coli* strain BL21, refolding was done in arginine. Following refolding, the protein was dialyzed and purified by Q-sepharose and gel filtration (sephadex 75). Two peaks were detected by SDS-PAGE (non-reduced) and by gel filtration. The peaks were collected separately and analyzed by FACS. Monomer and dimer binding to Jurkat cells was checked by FACS. The binding by dimers required only 1/100 the amount of the monomeric antibody for the same level of staining, indicating that the dimer has greater avidity. Conditions for dimer refolding were determined, and material comprising >90% dimers (mg quantities) was produced after subsequent dialysis, chromatographic, and gel filtration steps. The purified dimer was characterized by gel filtration and by SDS-PAGE analysis under oxidizing conditions. The dimer's binding capacity was confirmed by radioreceptor assay, ELISA, and FACS analyses.

CONY1 scF antibody fragment is derived from Y1 scFV. The DNA sequence encoding the myc tag of Y1 scFv were removed and replaced by synthetic oligonucleotide DNA sequence encoding the amino acids lysine, alanine lysine (KAK).

To compare the binding of the Y1 scFv monomer (also referred to as CONY1) with the YI dimer, binding competition experiments were done in vitro on KG-1 cells. In addition, these experiments also compared the binding of the full YI IgG to the scFv Y1 monomers. To perform this study, Y1 IgG was labeled with biotin. This study revealed that Y1 IgG competed with IgG Y1-Biotin. Non-relevant human IgG did not compete with the labeled Y1 IGg. Y1 scFvs (5 µg and 10 µg) partially competed with Y1 IgG-Biotin (50 ng). The studies also showed that 1 ng of IgGY1-FITC bound to KG-1 cells (without serum) to the same extent as 1 µg of scFv-FITC, but in the presence of serum, most of Y1 IgG binding was "blocked." These studies also showed that the binding of the Y1 dimer is at least 20-fold higher than that of the scFV monomer as analyzed by radioreceptor assay, ELISA or FACS.

Figure 12:
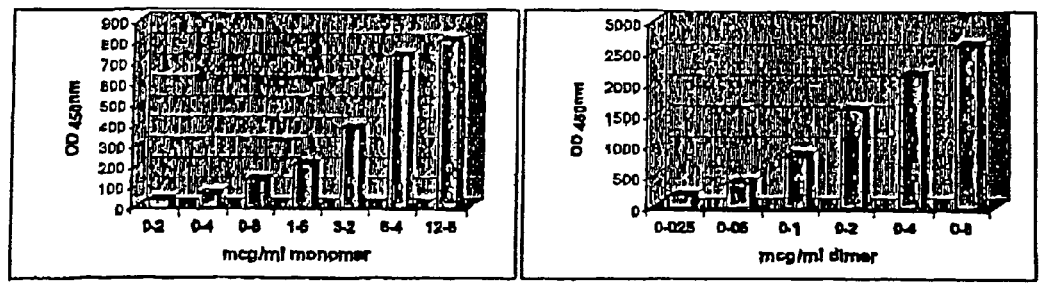
FIG. 12: This figure provides results of an ELISA assay.
Figure 13:
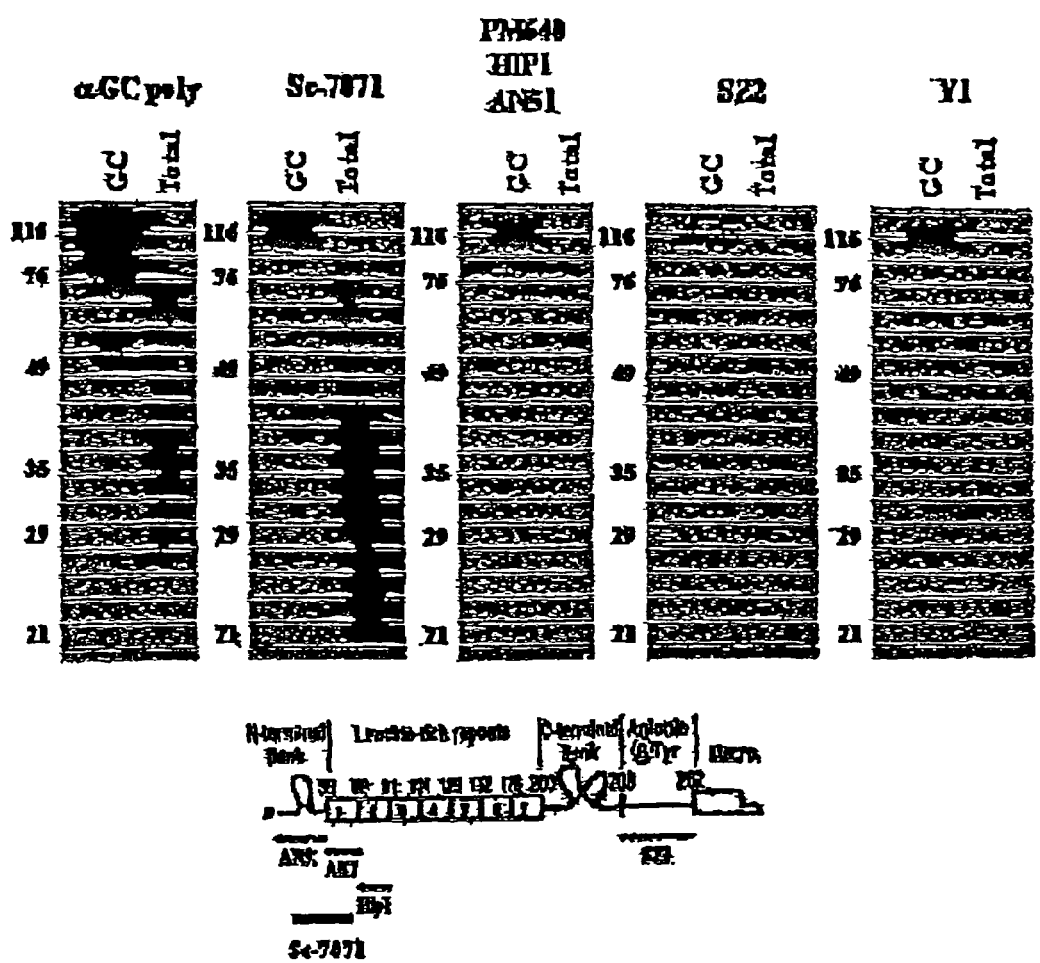
FIG. 13: This figure is a chart of the epitopes of anti-GPIbα antibodies.

In yet another embodiment, a lysine-alanine-lysine was added in addition to the cysteine at the carboxyl end (referred to as YI-cys-KAK scFv). The amino acid sequence of this scFv construct is reproduced below (SEQ ID NO: 208).

polyclonal anti-$V_L$ (derived from rabbits) and anti-rabbit HRP, were used to detect the binding to GPIb. The dimer was approximately 20–100 fold more active than the monomer. For instance, to reach 0.8 OD units 12.8 mg/ml of monomer was used compared to only 0.1 mg/ml of dimer. See FIG. 12.

The dimer was characterized by SDS-page electrophoresis, gel filtration chromatography, ELISA, radioreceptor binding, and FACS. The apparent affinity of the dimer was higher than the monomer due to the avidity effect. This effect was confirmed by ELISA to glycocalicin, FACS to KG-1 cells, and competition in a radioreceptor assay.

Figure 10:
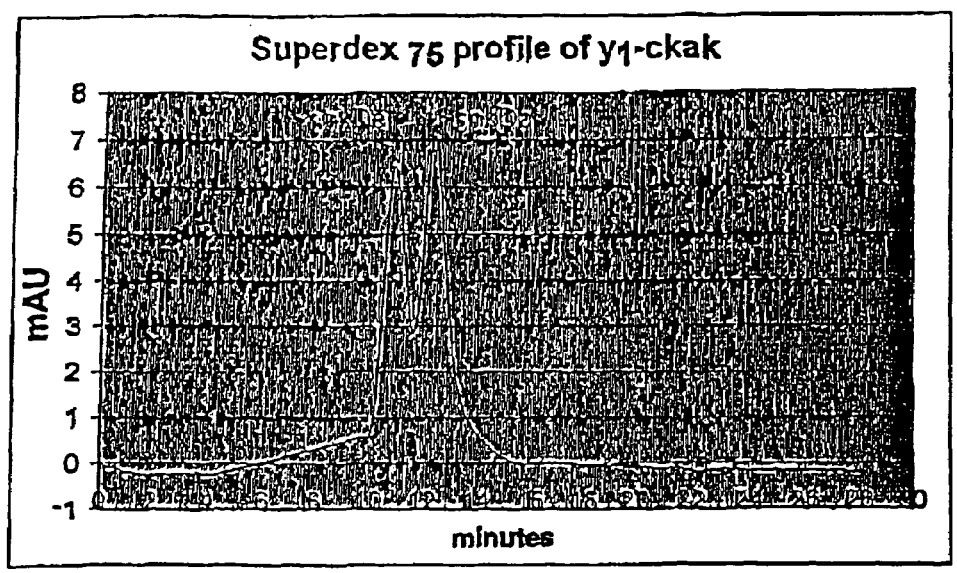
FIG. 10: This figure is a graph of the Superdex 75 profile of Y1-cys-kak.

HPLC was performed to profile the dimer after refolding and purification from a Superdex 75 gel filtration column. In FIG. 10, the Y1-cys-kak (dimer) is the first peak on the left (~10.8 minutes) and the subsequent peak is the monomer (~12 minutes). The dimer is approximately 52 kDa and the monomer 26 kDa, according to protein size markers run on the same column. The balance between the dimer and monomer can be changed by varying the conditions of the refolding (concentration of the oxidized agent and the concentration of the protein in the refolding buffer). The dimer and monomer were separated by chromatography in a superdex 75 column.

Figure 11:
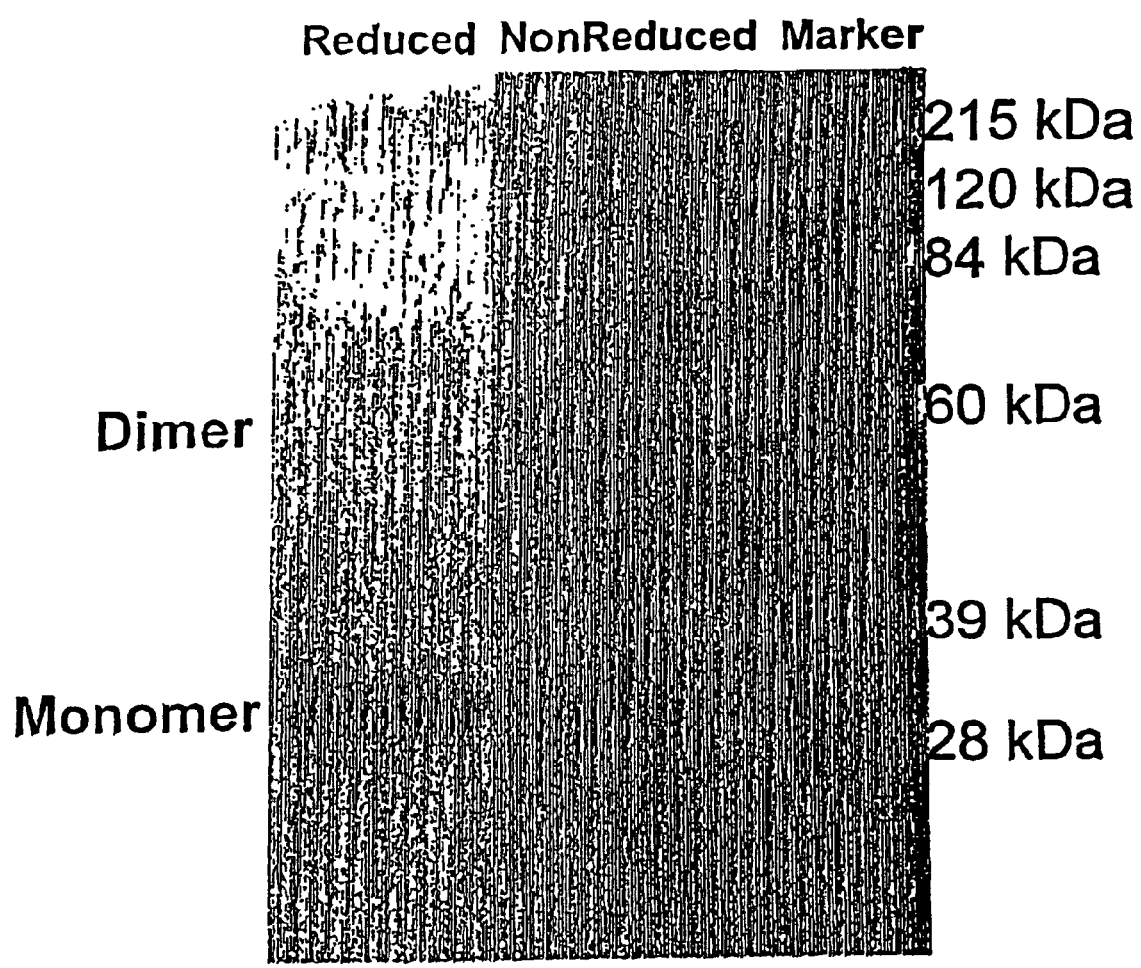
FIG. 11: This figure reveals the size of the dimers compared to the monomer in reducing and non-reducing conditions.

In FIG. 11, a gel is shown with a mixed population of dimers and monomers. In the reduced form, the monomers are seen due to the reduction between the two monomers and in the non-reduced form, two population are seen (as in the gel filtration experiment) a monomer fraction of about 30 kDa and a dimer of about 60 kDa.

In addition, FACS binding analysis to KG-1 cells showed that the dimer is more sensitive than the monomer when a

```
  1 MEVQLVESGGGVVRPGGSLRLSCAASGFTFDDYGMSWVRQAPGKGLEWVSGINWNGGSTG        60

61 YADSVKGRFTISRDNAKNSLYLQMNSLRAEDTAVYYCARMRAPVIWGQGTLVTVSRGGGG       120

121 SGGGGSGGGGSSELTQDPAVSVALGQTVRITCQGDSLRSYYASWYQQKPGQAPVLVIYGK       180

181 NNRPSGIPDRFSGSSSGNTASLTITGAQAEDEADYYCNSRDSSGNHVVFGGGTKLTVLGG       240

241 GGCKAK
```

The Y1-cys-KAK was produced in a λ-pL vector in bacteria. Expression in the λ-pL vector was induced by increasing the temperature to 42EC. Inclusion bodies were obtained from induced cultures and semi-purified by aqueous solutions, to remove unwanted soluble proteins. The inclusion bodies were solubilized in guanidine, reduced by DTT, and refolded in vitro in a solution based on arginine/oxidized-glutathione. After refolding, the protein was dialyzed and concentrated by tangential flow filtration to a buffer containing urea/phosphate buffer. The protein was repurified and concentrated by ionic-chromatography in an SP-column.

In order to obtain higher levels of expression in *E. coli* of the CONY1 scFv, as well as in the Y1-cys-KAK scFv, we introduced at position 2 of the N-terminal sequence of the scFv construct the amino acid encoding for the alanine residue. A four-fold level of expression was obtained with this newly modified construct.

An ELISA assay was performed to ascertain the differences in binding between the monomer (CONY1 scFv-also known as Y1-kak) and the dimer YI-cys kak (the cysteine dimer) for antigen GPIb (glycocalicin) derived from platelets. A polyclonal anti single chain antibody and/or a novel two or three-step binding assay was performed. Dimers directly labeled by FITC showed a slight advantage (use of 10× fold less material) than the monomer. The radio receptor assay on KG-1 cells, where the dimer was used as competitor, showed that the dimer is 30× fold more efficient than the monomer.

Varying the length of the spacers is yet another preferred method of forming dimers, trimers, and tetramers (often referred to in the art as diabodies, triabodies and tetrabodies, respectively). Dimers are formed under conditions where the spacer joining the two variable chains of a scFv is shortened. This shortened spacer prevents the two variable chains from the same molecule from folding into a functional Fv domain. Instead, the domains are forced to pair with complimentary domains of another molecule to create two binding domains. In a preferred method, a spacer of only 5 amino acids (Gly$_4$Ser) was used for diabody construction. This dimer can be formed from two identical scFvs, or from two different populations of scFvs and retain the selective and/or specific enhanced binding activity of the parent scFv(s), and/or show increased binding strength or affinity.

In a similar fashion, triabodies are formed under conditions where the spacer joining the two variable chains of a scFv is shortened to generally less than 5 amino acid residues, preventing the two variable chains from the same molecule from folding into a functional Fv domain. Instead, three separate scFv molecules associate to form a trimer. In a preferred method, triabodies were obtained by removing this flexible spacer completely. The triabody can be formed from three identical scFvs, or from two or three different populations of scFvs and retain the selective and/or specific enhanced binding activity of the parent scFv(s), and/or show increased binding strength or affinity.

Tetrabodies are similarly formed under conditions where the spacer joining the two variable chains of a scFv is shortened to generally less than 5 amino acid residues, preventing the two variable chains from the same molecule from folding into a functional Fv domain. Instead, four separate scFv molecules associate to form a tetramer. The tetrabody can be formed from four identical scFvs, or from 1–4 individual units from different populations of scFvs and should retain the selective and/or specific enhanced binding activity of the parent scFv(s), and/or show increased binding strength or affinity.

Whether triabodies or tetrabodies form under conditions where the spacer is generally less than 5 amino acid residues long depends on the amino acid sequence of the particular scFv(s) in the mixture and the reaction conditions.

In a preferred method, tetramers are formed via a biotin/streptavidin association. A novel fermentation construct that is capable of being enzymatically labeled with biotin (referred to herein as Y1-biotag or Y1-B) was created. A sequence that is a substrate for the BirA enzyme was added at the Y1 C-terminus. The BirA enzyme adds a biotin to the lysine residue within the sequence. Y1-biotag was cloned and expressed in E. coli. The inclusion body material was isolated and refolded. The purity of the folded protein was >95%, and >100 mg were obtained from a 1-L culture (small-scale, non-optimized conditions). The molecular weight of this form was found to be similar to that of the scFv according to HPLC, SDS-PAGE, and mass spectroscopy. Y1-biotag was found to be the most consistent reagent for FACS analysis. However, when Y1-biotag binding to KG-1 cells was examined in the presence of serum, high concentrations (10-fold more) are required for comparable binding in the absence of serum. Nevertheless, this construct offered the advantage of specific biotinylation in which the binding site of the molecule remains intact. Further, each molecule is labeled by only one biotin—each molecule receives one biotin on the carboxyl end.

Limiting labeling to one biotin/molecule in a desired location enabled production of tetramers with streptavidin. The tetramers were formed by incubating Y1-B with steptavidin-PE.

FACS analysis indicated that the tetramers made by Y1-biotag and streptavidin-PE were 100 to 1000 fold more sensitive that Y1 scFv monomers in the absence of serum. Y1-biotag tetramers with strepavidin-PE appear to specifically bind to one of the Y1-reactive cell lines (KG-1). The differential of this reaction, from background binding, was very high, and offered high sensitivity to detect low amounts of receptor. FACS evaluation of normal whole blood with Y1-SAV tetramers indicated that no highly reactive population is present. Monocytes and granulocytes were positive to a small extent. In cell lines where a positive result was present, such as with KG-1 cells, the tetramers were at least 100-fold more reactive.

Then, the tetramers were incubated with the cell samples. A low dose of the Y1 tetramers (5 ng) binds well to the cell line (KG-1) providing a 10 to 20-fold higher response than previously observed with other Y1 antibody forms. A minor reaction was observed when a negative cell line was examined with varying doses of the tetramers.

An embodiment of the invention provides for a method for identifying a targeting molecule which binds to unknown immuno-cross-reactive binding sites on first and second cells comprising (a) one or more biopanning steps that are performed on a first target cell that, in a second state but not in a first state, substantially exposes or displays a binding site comprising an unknown ligand so as to produce a first population of recognition molecules; (b) subsequent biopanning and/or selection steps, commencing with the resultant stock of recognition molecules of step (a), that are performed on a second cell that displays a binding site comprising an unknown ligand having immuno-cross-reactivity to the unknown ligand of the first cell so as to produce a second population of recognition molecules; (c) amplification and purification of the second population of recognition molecules of step (b); and (d) construction from the recognition sites of the purified recognition molecules of step (c) peptides or polypeptides that comprise targeting molecules that are selective and/or specific for unknown ligands on the second cell.

A preferred embodiment provides for the first cell to be a normal cell, the first state to be a non-activated state and the second state to be an activated, excited, modified, changed or disturbed state. In a more preferred embodiment the second cell is a diseased cell. In a yet more preferred embodiment the diseased cell is a cancer cell. The cancer cell may be, but is not limited to carcinoma, sarcoma, leukemia, adenoma, lymphoma, myeloma, blastoma, seminoma, and melanoma. In a yet more preferred embodiment, the cancer cell is a leukemia cell. In a most preferred embodiment the leukemia cell is an AML cell.

An embodiment of the present invention provides for use of the peptide or polypeptide optionally in association with or attached, coupled, combined, linked or fused to a pharmaceutical agent, in the manufacture of a medicament. In a preferred embodiment the medicament has activity against a diseased cell. In yet a more preferred embodiment, the activity is against a cancer cell. The cancer cell be but is not limited to carcinoma, sarcoma, leukemia, adenoma, lymphoma, myeloma, blastoma, seminoma, and melanoma. In yet a more preferred embodiment the cancer cell is a leukemia cell. In a most preferred embodiment the leukemia cell is an AML cell.

An embodiment of the invention provides for a pharmaceutical composition comprising mixtures of different monomeric scFvs, and/or mixtures of diabodies or triabodies or tetrabodies constructed from different scFvs.

A further embodiment provides for use of the peptide or polypeptide of the invention, in association with, or attached, coupled, combined, linked or fused to a pharmaceutical agent, in the manufacture of a medicament. The medicament can have activity against diseased cells, and more specifically against cancer cells. The cancer cells may be, but are not limited to, carcinoma, sarcoma, leukemia, adenoma, lymphoma, myeloma, blastoma, seminoma, and melanoma. In a more preferred embodiment, the medicament is active against leukemia cells. In a most preferred embodiment, the medicament is active against AML cells. Activity of the medicament against the said cells may cause retardation of cancerous growth, complete prevention of any growth, or killing of the cancerous cells.

In an embodiment of the invention, the activity of the medicament or of the pharmaceutical composition is by inhibiting cell growth.

The peptide or polypeptide of the invention can be used for preparing a composition, preferably a pharmaceutical composition, for use in inhibiting the growth of a cancer cell, preferably a leukemia cell, and most preferably an AML cell. In an embodiment of the invention, the peptide or polypeptide can be used for preparing a composition for use in inhibition of growth of a cancer cell, said composition comprising at least one compound having a pharmaceutical ligand selective and/or specific for the cancer cell.

A peptide or polypeptide of the subject invention may be administered alone to a patient, or as comprising a medicament or a pharmaceutical composition, in association with, conjugated, linked, or fused to a pharmaceutically effective amount of a pharmaceutical agent, a pharmaceutically effective carrier and, optionally, an adjuvant. Such pharmaceutical compositions may include proteins, diluents, preservatives and anti-oxidants (see Osol et al. (eds.), *Remington's Pharmaceutical Sciences* (16$^{th}$ ed), Mack Publishing Company, (1980)).

In another embodiment, the pharmaceutical agent is an antibody or fragment thereof that is linked to a peptide or polypeptide of the invention by a peptide bond.

In a preferred embodiment, the toxin is, for example, gelonin, Pseudomonas exotoxin (PE), PE40, PE38, diptheria toxin, ricin, or modifications or derivatives thereof.

In a preferred embodiment, the radioisotopes used include gamma-emitters, positron-emitters, and x-ray emitters that may be used for localization and/or therapy, and beta-emitters and alpha-emitters that may be used for therapy.

In a specific embodiment of the subject invention, the therapeutic radioisotope is selected from a group comprising $^{111}$indium, $^{113}$indium, $^{99m}$rhenium, $^{105}$rhenium, $^{101}$rhenium, $^{99m}$technetium, $^{121m}$tellurium, $^{122m}$tellurium, $^{125m}$telluriunm $^{165}$thulium, $^{167}$thulium $^{168}$thulium $^{123}$iodine, $^{126}$iodine, $^{131}$iodine, $^{133}$iodine, $^{81m}$krypton, $^{33}$xenon, $^{90}$yttrium, $^{213}$bismuth, $^{77}$bromine, $^{18}$fluorine, $^{95}$ruthenium, $^{97}$ruthenium, $^{103}$ruthenium, $^{105}$ruthenium, $^{107}$mercury, $^{203}$mercury, $^{67}$gallium and $^{68}$gallium and the like.

In another specific embodiment of the subject invention, the anti-cancer agent is selected from the group comprising doxorubicin, adriamycin, cis-platinum, taxol, calicheamicin, vincristine, cytarabine (Ara-C), cyclophosphamide, prednisone, daunorubicin, idarubicin, fludarabine, chlorambucil, interferon alpha, hydroxyurea, temozolomide, thalidomide and bleomycin, and derivatives thereof.

An embodiment of the invention provides for a method of inhibiting the growth of a cancer cell that comprises contacting the cancer cell with an amount of the peptide or polypeptide of the invention. In a preferred embodiment, the cancer cells may be but are not limited to carcinoma, sarcoma, leukemia, adenoma, lymphoma, myeloma, blastoma, seminoma, and melanoma. In a more preferred embodiment the cancer cell is a leukemia cell. In a most preferred embodiment the leukemia cell is an AML cell. An embodiment of the invention allows for in vivo and ex vivo treatment of the patient. A more specific embodiment of the invention allows for ex vivo purging of autologous bone marrow to remove abnormal stem cells.

In a more specific embodiment of the invention, the blood of a leukemia patient can be circulated ex vivo through a system comprising a peptide or polypeptide of the invention conjugated to an anti-cancer agent. After removal of bound cells and unbound anti-cancer agent, the blood cells can be reintroduced into the body of a patient. Alternatively, the blood of a leukemia patient can be circulated ex vivo through a system comprising a peptide or polypeptide of the invention attached to a solid phase. The cells that pass through the system and that do not bind to the peptide or polypeptide of the invention attached to a solid phase can be reintroduced into the body of a patient.

In another preferred embodiment of the invention, the peptide or polypeptide is utilized for ex vivo autologous bone marrow in suspension in order to remove abnormal stem cells prior to implantation. Purging of abnormal stem cells can be performed by running the suspension over a solid support (such as, but not limited to, magnetic beads and affinity columns) to which the peptide or polypeptide of the invention (i.e., the targeting molecule), constructs, fragments, fragments of constructs, or constructs of fragments thereof are bound. Bone marrow thus purged ex vivo can then be used for autologous bone marrow transplantation. This preferred embodiment is based on the identification in the present invention of a phagemid clone (Y1) that binds to stem cells released from bone marrow of leukemia patients, but does not bind to stem cells released from the bone marrow of healthy donors. Similarly, the Y1 phagemid clone binds to blast cells that are determined by FACS analysis to be abnormal, as well as to leukemic cells.

Blast cells are herein defined as primary cells that are precursors for all the circulating cells in the mammalian organism. Due to their progenitor characteristics, blast cells are not found circulating in significant quantities in the adult organism. The presence of circulating blast cells without exogenous stimulation can be an indication of malignancy, e.g., of the hematopoietic system, and their subsequent disappearance may indicate remission of the malignant disease.

In another embodiment of the invention, the pharmaceutical composition is used for prophylaxis.

In a preferred embodiment, two or more peptides or polypeptides of the invention are combined to form a mixture.

As used herein, a mixture is defined as two or more molecules or particles of different species that are contained in a single preparation. The different species of molecules form neither covalent nor non-covalent chemical bonds.

In one embodiment of the subject invention, the peptide or polypeptide of the subject invention is linked, fused or conjugated to a pharmaceutical agent.

In another embodiment of the subject invention, the link between the peptide and the pharmaceutical agent is a direct link. As used herein, a direct link between two or more neighboring molecules is obtained via a chemical bond between elements or groups of elements in the molecules. The chemical bond can be for example, an ionic bond, a covalent bond, a hydrophobic bond, a hydrophilic bond, an electrostatic bond or a hydrogen bond. The bonds can be selected from, but not limited to, a group comprising amine, carboxy, amide, hydroxyl, peptide and disulfide. The direct link could preferably be a protease resistant bond.

In yet another embodiment, the link between the peptide and the pharmaceutical agent is affected by a linker compound. As used herein in the specification and in the claims, a linker compound is defined as a compound that joins two or more moieties together. The linker can be straight-chained or branched. The branched linker compound can be composed of a double-branch, triple branch, or quadruple or more branched compound. The linker compound may be, but is not limited to, a dicarboxylic acid, a maleimido hydrazide, PDPH, a carboxylic acid hydrazide, and a small peptide. Examples of other linker compounds include: Dicarboxylic acids such as succinic acid, glutaric acid, and adipic acid; Maleimido hydrazides such as N-[ε-maleimidocaproic acid]hydrazide, 4-[N-maleimidomethyl]cyclohexan-1-carboxylhydrazide, and N-[κ-maleimidoundecanoic acid]hydrazide]; PDPH linker such as (3-[2-pyridyldithio]propionyl hydrazide) conjugated to sulfurhydryl reactive protein; Carboxylic acid hydrazides selected from 2–5 carbon atoms; and direct coupling using small peptide linkers between the free sugar of, for example, the anti-cancer drug doxorubicin and a scFv. Small peptides include, but are not limited to AU1, AU5, BTag, c-myc, FLAG, Glu-Glu, HA, His6 (SEQ ID NO: 204), HSV, HTTPHH (SEQ ID NO:205), IRS, KT3, Protein C, S-TAG®, T7, V5, VSV-G, and KAK Tag (SEQ ID NO:238).

Any known method of administration of a peptide or polypeptide of the subject invention may be sued such as: intravenous, intramuscular, subcutaneous, topical, intratracheal, intrathecal, intraperitoneal, intralymphatic, nasal, sublingual, oral, rectal, vaginal, respiratory, buccal, intradermal, transdermal or intrapleural.

For intravenous administration, the formulation preferably will be prepared so that the amount administered to the patient will be an effective amount from about 0.1 mg to about 1000 mg of the desired composition. More preferably, the amount administered will be in the range of about 1 mg to about 500 mg of the desired composition. The compositions of the invention are effective over a wide dosage range, and depend on factors such as the particulars of the disease to be treated, the half-life of the peptide or polypeptide-based pharmaceutical composition in the body of the patient, physical and chemical characteristics of the pharmaceutical agent and of the pharmaceutical composition, mode of administration of the pharmaceutical composition, particulars of the patient to be treated or diagnosed, as well as other parameters deemed important by the treating physician.

The pharmaceutical composition for oral administration can be in the form of tablet, liquid, emulsion, suspension, syrup, pill, caplet, or capsule. The pharmaceutical composition may also be administered in a device.

The pharmaceutical composition for topical administration can be in the form of cream, ointment, lotion, patch, solution, suspension, or gel.

In addition, the pharmaceutical composition can be prepared for solid, liquid, or sustained release formulation.

The compositions comprising the antibody fragments produced in accordance with the invention may comprise conventional pharmaceutically acceptable diluents or carriers. Tablets, pills, caplets and capsules may include conventional excipients such as lactose, starch and magnesium stearate. Suppositories may include excipients such as waxes and glycerol. Injectable solutions comprise sterile pyrogen-free media such as saline, and may include buffering agents, stabilizing agents or preservatives. Conventional enteric coatings may also be used.

The subject invention also encompasses a method of producing the antibody fragment by synthetic means known in the art.

An embodiment of the invention comprises a pharmaceutical composition comprising at least one peptide or polypeptide of the invention, attached, coupled, combined, linked or fused to an imaging agent for use in the diagnostic localization and/or imaging of a tumor.

A further embodiment of the invention provides for a diagnostic kit for in vitro analysis of treatment efficacy before, during, or after treatment, comprising an imaging agent comprising a peptide of the invention linked to an indicative marker molecule. The invention further provides for a method of using the imaging agent for diagnostic localization and/or imaging of a cancer, more specifically a tumor, comprising the following steps:

a) contacting the cells with the composition,
b) measuring the radioactivity bound to the cells, and
c) visualizing the tumor.

In a preferred embodiment of the invention, the imaging agent of the kit is a fluorescent dye and the kit provides for analysis of treatment efficacy of cancers, more specifically blood-related cancers, e.g., leukemia, lymphoma and myeloma. FACS analysis is used to determine the percentage of cells stained by the imaging agent and the intensity of staining at each stage of the disease, e.g., upon diagnosis, during treatment, during remission and during relapse.

The invention further provides a composition comprising an effective amount of an imaging agent, the peptide of the invention and a physiologically acceptable carrier.

In a preferred embodiment, the indicative marker molecule is any known marker known in the art, which includes, but is not limited to, a radioactive isotope, an element that is opaque to X-rays, a paramagnetic ion, or a fluorescent molecule, and the like.

In a specific embodiment of the subject invention, the indicative radioactive isotope may be, but is not limited to, $^{111}$indium, $^{113}$indium, $^{99m}$rhenium, $^{105}$rhenium, $^{101}$rhenium, $^{99m}$technetium, $^{121m}$tellurium, $^{122m}$tellurium, $^{125m}$telluriunm $^{165}$thulium, $^{167}$thulium $^{168}$thulium $^{123}$iodine, $^{126}$iodine, $^{131}$iodine, $^{133}$iodine, $^{81m}$krypton, $^{33}$xenon, $^{90}$yttrium, $^{213}$bismuth, $^{77}$bromine, $^{18}$fluorine, $^{95}$ruthenium, $^{97}$ruthenium, $^{103}$ruthenium, $^{105}$ruthenium, $^{107}$mercury, $^{203}$mercury, $^{67}$gallium and $^{68}$gallium.

According to another preferred embodiment the indicative marker molecule is a fluorescent marker molecule. According to a more preferred embodiment the fluorescent marker molecule is fluorescein, phycoerythrin, or rhodamine, or modifications or conjugates thereof.

The subject invention also envisages a composition comprising an effective amount of an imaging agent of the invention, a pharmaceutical agent linked thereto and a physiolgically acceptable carrier.

The invention also provides a method for imaging an organ or cells that involves contacting the organ or cells to be imaged with an imaging agent of the invention under conditions such that the imaging agent binds to the organ and cells, imaging the bound imaging agent and, thereby, imaging the organ or cells.

The subject invention further provides a method of treating an organ in vivo that involves contacting the organ to be treated with a composition of the invention under conditions such that the composition binds to the organ, thereby treating the organ.

In a preferred embodiment of the invention, the peptide or polypeptide may be utilized to target malignant cells, more particularly, leukemia cells in whole blood, by monitoring and imaging the cells, e.g., by FACS analysis. Specimens receiving higher scores (e.g., four-fold higher) for tumor cells relative to normal cells are subject for treatment.

The invention provides for treating a patient suffering from a cancer, comprising administering to the patient an amount of the peptide or polypeptide of the invention effective to treat the cancer. In a preferred embodiment the cancer is selected from the group comprising carcinoma, sarcoma, leukemia, adenoma, lymphoma, myeloma, blastoma, seminoma, and melanoma. In a more preferred embodiment the cancer is a leukemia and in a most specific embodiment the leukemia is AML.

In a most preferred embodiment the peptide or polypeptide of the invention specifically or selectively binds to AML cells. The invention provides for a ligand presented on AML cells bound the peptide or polypeptide of the invention, and further provides for a peptide or polypeptide that binds said ligand.

The novel antibody fragments of the subject invention or their corresponding peptidomimetics are used in the manufacture of compositions or medicaments to treat various diseases and conditions.

The subject invention provides a method for production of a targeting agent comprising the following steps:

a) isolating and selecting one or more targeting molecules comprising a primary recognition site by a biopanning procedure directly on a target cell or by a biopanning procedure indirectly on a first target cell in a second but not in a first state and subsequently by a biopanning procedure directly on a second target cell to produce one or more said targeting molecules;

b) amplification, purification and identification of the one or more targeting molecules; and c) construction of a targeting agent from the one or more targeting molecules or recognition sites thereof wherein the targeting agent can be a peptide, polypeptide, antibody or antibody fragment or a multimer thereof.

The targeting agent can additionally be constructed so as to be coupled, attached, combined, linked or fused to or in association with a pharmaceutical agent.

In a preferred embodiment of the invention the targeting agent is an anti-disease or anti-cancer agent.

In another preferred embodiment of the invention the pharmaceutical agent is selected from the group comprising radioisotope, toxin, oligonucleotide, recombinant protein, antibody fragment, and anti-cancer agent. The radioisotope may be selected from a group comprising $^{111}$indium, $^{113}$indium, $^{99m}$rhenium, $^{105}$rhenium, $^{101}$rhenium, $^{99m}$technetium, $^{121m}$tellurium, $^{122m}$tellurium, $^{125m}$telluriunm $^{165}$thulium, $^{167}$thulium $^{168}$thulium $^{123}$iodine, $^{126}$iodine, $^{131}$iodine, $^{133}$iodine, $^{81m}$krypton, $^{33}$xenon, $^{90}$yttrium, $^{213}$bismuth, $^{77}$bromine, $^{18}$fluorine, $^{95}$ruthenium, $^{97}$ruthenium, $^{103}$ruthenium, $^{105}$ruthenium, $^{107}$mercury, $^{203}$mercury, $^{67}$gallium and $^{68}$gallium.

In yet another embodiment the toxin may be selected from the group comprising gelonin, Pseudomonas exotoxin (PE), PE40, PE38, diptheria toxin, ricin, or modifications or derivatives thereof.

In yet another embodiment of the invention the anti-cancer agent is selected from the group comprising doxorubicin, morpholino-doxorubicin (MDOX), adriamycin, cis-platinum, taxol, calicheamicin, vincristine, cytarabine (Ara-C), cyclophosphamide, prednisone, daunorubicin, idarubicin, fludarabine, chlorambucil, interferon alpha, hydroxyurea, temozolomide, thalidomide and bleomycin, and derivatives thereof.

The subject invention provides a method for the identification of antibody fragments by: (a) biopanning that involves incubating a phage display library with cells derived from blood; (b) washing to remove unbound phage; (c) eluting the bound phage from the blood cells; (d) amplifying the resulting bound phage; and (e) determining the displayed peptide sequence of the bound phage so as to identify the peptide.

The subject invention provides for a peptide or polypeptide having, the formula or structure:

A-X-B wherein X is a hypervariable CDR3 region of 3 to 30 amino acids; and A and B can each be amino acid chains from 1 to 1000 amino acids in length, wherein A is the amino end and B is the carboxy end.

In a preferred embodiment of the invention A is 150–250 amino acid residues and B is 350–500 amino acid residues.

In another preferred embodiment the CDR3 region of the peptide is 5–13 amino acid residues.

In another preferred embodiment X in the formula above is an amino acid sequence selected from the group consisting of SEQ ID NOs:8–24.

In another embodiment of the invention the peptide or polypeptide is part of a larger or full antibody or a multimer.

In yet another embodiment a dimeric molecule comprises two peptides or polypeptides, one of which is the peptide or polypeptide of the invention. The dimeric molecule may comprise two identical peptides or polypeptides of the invention.

In a preferred embodiment of the invention X is an amino acid sequence selected from the group consisting of SEQ ID NOs:8–24 in said dimeric molecule.

Another embodiment provides for a nucleic acid molecule encoding the peptide or polypeptide or dimeric molecule of the invention.

The invention provides for the use of the peptide or polypeptide, optionally in association with or attached, coupled, combined, linked or fused to a pharmaceutical agent, in the manufacture of a medicament.

The invention further provides for use of the peptide or polypeptide in the manufacture of a medicament that has activity against a diseased cell, more specifically a cancer cell. The cancer cell may be selected from a group comprising carcinoma, sarcoma, leukemia, adenoma, lymphoma, myeloma, blastoma, seminoma, and melanoma. More specifically, the cancer cell may be a leukemia cell and most specifically, the leukemia cell may be an AML cell.

An exchangeable system, as defined in the present invention and as discussed below in the examples, is a nucleic acid construct that has been designed to allow for exchange or replacement of a redefined variable region within said construct, without need for further manipulation or rebuilding of the molecule. Such a system allows for rapid and convenient preparation of the desired nucleic acid molecule.

EXAMPLES

The following examples are set forth to aid in understanding the invention but are not intended and should not be construed, to limit its scope in any way. Although specific reagents and reaction conditions are described, modifications can be made that are meant to be encompassed by the scope of the invention. The following examples, therefore, are provided to further illustrate the invention.

Example 1

1. Preparation of cells, bacterial strains, scFv phage display library, cellular membranes and protein purification for the biopanning procedure 1.1 Preparation of leukemia cells. Blood samples were obtained from leukemia patients. Mononuclear cells (primary cells) were separated from other blood cells on a Ficoll cushion (Iso-prep, Robbins Scientific Corp., Sunnyvale, Calif., USA). Centrifugation was performed at 110×g for 25 minutes. Cells at the interface were collected and washed twice in PBS. Cells were then suspended in RPMI+10% fetal calf serum (FCS) and enumerated. For long term storage, 10% FCS and 10% DMSO were added to the lymphocytes which were then frozen at −70° C.

1.2 Preparation of fixed platelets. Platelet concentrate obtained from a blood bank was incubated for 1 hour, at 37° C. An equal volume of 2.0% paraformaldehyde was added, and platelets were fixed for 18 hr, at 40° C. The platelets were washed twice with cold saline (centrifugation for 10 min, at 2500×g), resuspended in 0.01% HEPES in saline, and counted using a microscope.

Platelet sensitivity to plasma von Willebrand factor and ristocetin was verified. Plasma von Willebrand factor (vWF; 18 µg/ml) and ristocetin (0.6 mg/Ml) were added to fixed platelets, and platelet aggregation was induced and monitored by a chronolog lumi-aggregometer.

1.3 Bacterial strains—TG-1 and HB2151: Fresh bacterial cultures were prepared for infection by growing the cells to $A_{600}$ of 0.5–0.9 (exponentially growing cells). *E. coli* TG-1 cells were used for phage propagation and *E. coli* HB2151 cells were used for scFv protein production.

1.4 scFv display phage library source. The scFv library (Nissim et al., *EMBO J.*, 13, 692–698 (1994)) was provided by Dr. A. Nissim with the agreement of the MRC. The library was originally constructed as a phagemid library displaying scFv fragments in which the $V_H$ and the $V_L$ domains were linked by a flexible polypeptide. The scFvs displayed in the phagemid library were fused to the N-terminus of the minor coat protein pIII of the phage, which was then subcloned into the pHEN1 vector (Nissim et al., *EMBO J*, 13, 692–698 (1994)). Repertoires of antibody fragments were first generated by PCR from rearranged V-genes of peripheral blood lymphocytes of unimmunized human (referred to as "naive repertoires"). To diversify the repertoire, random nucleotide sequences encoding heavy chain CDR3 lengths of 4–12 residues were introduced into a bank of 49 cloned human $V_H$ gene segments. The fused $V_L$ fragment in all the clones it derived from a single unmutated V gene of germline IGLV3S1, creating a single pot library of approximately $10^8$ clones.

1.5 Membrane preparation from AML cells. To the pellet containing $10^8$ washed cells, 1 ml cold lysis solution (0.3M sucrose, 5 mM EDTA, 1 mM PMSF) was added, then spun for 20 minutes at 11,000×g at 4° C. The supernatant fluid was discarded, and the pellet was resuspended in TE (10 mM Tris, 1 mM EDTA, 1 mM PMSF) and spun as above. The final pellet was resuspended in 6 ml PBS at an $A_{280}$ of 0.4 and was used to coat 3 Maxisorb immuno-tubes (NUNC), at 37° C., for 2 hr. Following coating, tubes were rinsed 3 times with PBS, then blocked with MPBS (2% skim milk in PBS), at RT, for 2 hours. Before biopanning, the tubes were rinsed an additional three times with PBS.

Example 2

2. Manipulation of phagemid particles re: biopanning procedure 2.1 Phagemid selection and amplification: Phagemids that expressed epitopes of specific interest were selected from the library by a four-step biopanning procedure:
a) Binding of the phagemid particles to a target, more particularly binding of the phagemid particles to washed target cells or cell membranes
b) Removal of the non-bound phagemid particles, more particularly removal by extensive washing
c) Elution of bound phagemid particles
d) Propagation and amplification of the eluted phagemid particles, more particularly propagating and amplifying in *E. coli*

2.2 Clone identification: The four-step biopanning procedure was generally repeated 3–5 times. Selected phagemid clones were individually propagated, and further characterized by:
a) DNA sequencing
b) Comparison ex-vivo of phage binding to several cell types
c) Infection of *E. coli* HB2151 to produce soluble scFv 2.3 Sequence analysis: The encoded scFv DNA of ~800 bp within the phagemid particles was amplified by PCR using an upstream primer #203743 (5'-GAAATACCTAT-TGCCTACGG) (SEQ ID NO: 209) and a downstream primer #181390 (5'-TGAATTTTCTGTATGAGG) (SEQ ID NO: 210). DNA fragments were fully sequenced from both ends by the automatic ABI PRISM DNA sequencer (310 Genetic Analyzer, Perkin Elmer) using ABI PRISM Big Dye termination cycle sequencing kit and the above primers. Two additional primers, primer #191181 (5%-CGATCCGCCAC-CGCCAGAG) (SEQ ID NO: 211) and its complementary primer #191344 (5'-CTCTGGCGGTGGCGGATCG) (SEQ ID NO: 212), which are located at the flexible polypeptide junction region between the heavy and light chains, were used for sequencing.

Example 3

3. Biopanning protocols 3.1 Basic biopanning protocols: The biopanning procedure is an integral part of the phage display technology described above. Three biopanning protocols were developed and used in the present work:
a) Protocol AM (AML cell membrane panning/bacterial elution, followed by whole AML cell panning/trypsin elution)
b) Protocol YPR (fixed human platelet panning/acid elution)
c) Protocol YPNR (fixed human platelet panning/acid elution)

These protocols are described in detail below:

3.1.1 Protocol AM 3.1.1.1 Prewashing: One ml aliquots containing $2\times10^7$ frozen AML cells from patients, stored at −70° C., were quick-thawed at 37° C. and immediately diluted into 10 ml cold 2% PBS-Milk (MPBS). Cells were spun 5' at 120×g at room temperature (RT), washed twice, resuspended in MPBS and counted with a hemocytometer. Cell membranes were prepared as described in Section 1.5.

3.1.1.2 Selection was carried out on immobilized AML cell membranes by the addition of 2 ml MPBS containing $10^{12}$ phagemids from the original Nissim library. The tube was slowly agitated for 30 minutes, then incubated for an extra 90 minutes without agitation, both steps at RT. Following three rounds of panning on AML cell membranes, one round of panning was carried out on whole AML cells.

3.1.1.3 Wash: To remove excess unbound phagemids, the tube contents were decanted and the tube was washed 10 times with PBS, 0.1% Tween, followed by 10 washes with PBS only.

3.1.1.4 Elution: Exponentially growing *E. coli* TG-1 cells (2 ml) were added directly to the tube and incubated with slow agitation at 37° C. for 30 minutes. As above, an aliquot was plated for titration and the remaining volume was plated for amplification.

3.1.1.5 Amplification: Colonies from the large plates were scraped and pooled. An aliquot (~$10^7$) of ampicillin resistant *E. coli* TG-1 cells was grown in liquid culture to $A_{600}$ of ~0.5, then infected with helper phage (VSC-M13, Stratagene) to produce a large amplified phagemid stock.

Phagemids were rescued by a PEG precipitation procedure (18a). The amplified T1 6MI stock above (~$10^{11}$ phagemids/ml) was used for subsequent rounds of panning. The selection procedure was repeated for two additional rounds, using $10^{11}$ phagemids of the previously amplified stock. The amplified stock of the third panning procedure on immobilized membranes was designated T16M3.

3.1.1.6 Re-Panning on whole cells: The amplified stock of the third membrane panning, T16M3, was used to pan intact AML cells. Selection was carried out in a final volume of 0.5 ml MPBS containing $2\times10^7$ cells and $10^{10}$ Colony Forming Units (CFU) of phagemids (Nissim library), and $10^{13}$ wild-type bacteriophage M13, with slow agitation for 2 hours at 4° C. Bound phagemids were eluted from the washed cell pellet with 50 μl of Trypsin:EDTA (0.25%:0.05%), then neutralized by the addition of 50 μl of FCS. For titration and amplification, 1 ml of an E. coli TG-I culture ($A_{600}$=0.5) was used. The amplified, and final, stock was designated T16M3.1.

3.1.2 Protocol YPR 3.1.2.1 Selection: Clone selection was accomplished by panning $10^8$ fixed human platelets with $10^{11}$ phagemids (Nissim library) in 1 ml PBS/HEPES/1% BSA buffer. Binding was allowed to proceed for one hour at RT while mixing the sample by rotation.

3.1.2.2 Cell wash: Platelets were washed five times by low speed centrifugation (3500×g) and resuspended as above.

3.1.2.3 Elution: First round bound phagemids were eluted from fixed platelets by the acid elution technique:

The platelets were incubated for 10 minutes at RT with 200 μl 0.1 M glycine (pH 2.2). After neutralization with 0.5 M Tris-HCl, pH 8.0 and centrifugation, the remaining platelet-bound phage were eluted by addition of 200 μl trypsin-EDTA (0.25%/0.05) and neutralization by the addition of 50 μl FCS. The cells were removed by centrifugation, and the supernatant fluids containing eluted phage, from both acid and trypsin elution protocols, were collected and designated YPR(a)-1 and YPR(t)-1 stocks, respectively. These stocks were then amplified by adding 1 ml of exponentially growing TG-1 cells for 30 min., at 37° C. An aliquot was plated for titration, and the remaining infected E. coli cells were plated on 2×TV/AMP 15 cm plates. Plates were incubated overnight at 30° C. The output after each round of panning was determined by counting the colonies on a titration plate.

3.1.2.4 Amplification: The clones were amplified as described in section 3.1.1.5. The amplified stocks of ~$10^{12}$ phagemid/ml from the acid and trypsin elution protocols, designated R1(a) and R1(t) stocks, respectively, were combined and used for subsequent rounds of panning.

3.1.2.5 Second and third rounds of panning were carried out as described for the first panning round of the YPR procedure with the following modifications: (i) For the second panning $10^{12}$ of R1(a), combined with $10^{12}$ of R1(t), were used and (ii) elution was carried out with glycine (pH 2.2) only. The amplified eluate of the second round was designated R2. (iii) For the third round of biopanning, $10^{12}$ of R2 was used, and elution was carried out as in the second round. The amplified stock of round three was designated R3.

3.1.3 YPNR Protocol 3.1.3.1 Biopanning and washing were carried out essentially as described in the YPR protocol. However, in this protocol, (i) elution was carried out after each of three rounds of panning with glycine (pH 2.2), and (ii) the first panning and amplification were followed by two subsequent rounds of panning without amplification. The first, second, and third rounds were designated YPNR1, YPNR2, and YPNR3, respectively.

3.2 Selection of Negative Control scFv Clones 3.2.1 N14 CDR3 sequence: For all binding experiments, a single clone was picked from the naive library (before selection). A phage stock and a soluble scFv, designated N14, were prepared from this clone. Sequence analysis indicates that it belongs to the $V_H$4-DP65 gene family. The sequence of the 11-mer $V_H$-CDR3 encoded by this clone, designated N14 CDR3, is as follows (SEQ ID NO:28):

Phe Leu Thr Tyr Asn Ser Tyr Glu Val Pro Thr 3.2.2 C181 CDR3 sequence: An additional negative clone, C181, was used in the binding analysis experiments. Clone C181 (reactive to recombinant hepatitis B virus [HBV] particles) belongs to the $V_H$3-DP35 family, and the sequence of the 9-mer $V_H$-CDR3 encoded by this clone, designated C181 CDR3, is as follows (SEQ ID NO:29):

Thr Asn Trp Tyr Leu Arg Pro Leu Asn

Example 4

4. Production, Purification, Labeling and Characterization of scFv Clones 4.1 Production of soluble scFv: pHEN1, a vector used to construct the original phagemid library, was designed with an amber stop codon encoded at the junction of the scFv gene and the pIII gene. Therefore, when the vectors of selected clones are introduced by phagemid infection into E. coli HB215 1, which is a non-suppressor strain, this system enables production and secretion of soluble scFv into the bacterial periplasm (Harrison et al., Methods in Enzymology, 267, 83–109 (1996)). The scFv is then readily retrievable from the culture broth. Soluble scFvs are produced under the control of the lacZ promoter (Gilbert and Muller-Hill, PNAS (US), 58, 2415 (1967)), which is induced with IPTG.

A sequence encoding c-myc tag (10 amino acids—Glu Gln Lys Leu Ile Ser Glu Glu Asp Leu; SEQ ID NO: 123.) is contained in the vector upstream to the amber mutation. The C-terminus of the expressed scFv should carry the c-myc tag, which can be detected using mouse anti-myc tag antibodies (derived from the European Collection of Cell Culture (ECACC) 9E10-hybridoma).

4.2 Purification of scFv on Protein-A beads affinity column: The scFvs of selected clones and of the control clone C181 all belong to the $V_H$3 family, allowing purification on a Protein-A affinity column. Periplasmic fractions (100–250 ml) from induced cultures of each clone were prepared and incubated with Protein-A Sepharose beads. The bound scFvs were recovered from the column by acid elution (0.1 M glycine, pH 3.0), followed by eluate neutralization with Tris, pH.8.0. The concentration of the recovered protein was determined by $A_{280}$ measurement, followed by PBS buffer exchange by dialysis or on a G-25 Sepharose column.

4.3 Purification of N14-scFv on a Sephacryl S-200 column: The scFv of the negative clone N14 belongs to the $V_H$4 gene family and cannot, therefore, be purified on a Protein-A affinity column. For scFv-N14 purification, total protein in the periplasmic fraction of a 200 ml induced culture was precipitated by 60% ammonium sulfate. The pellet was resuspended in 2 ml 0.1×PBS, 5 mM EDTA, 5 mM PMSF and loaded on a Sephaeryl S-200 column (1.5×90 cm) pre-equilibrated with the running buffer (0.1×PBS, 5mM EDTA). Proteins were fractionated, and fractions containing the N14-scFv (as detected by SDS-PAGE and Western analysis) were pooled, lyophilized, and suspended in 1/10 volume H20. The N14-scFv (unlabeled and FITC-labeled) was then used as a negative control in FACS analysis experiments.

4.4. Labeling of purified scFvs with FITC: Approximately one milligram of purified scFv from each preparation was resuspended in PBS and coupled to FITC using a Fluoro-Tag FITC conjugation commercial kit (Sigma cat. #FITC-1), according to the manufacturer's instructions.

4.5 Quality Analysis of the Purified and Labeled scFv 4.5.1 Following purification and FITC labeling, the profile of each preparation (labeled and unlabeled) was analyzed by SDS-PAGE, Western blotting, HPLC using a Superdex-75 column (A280 and A495) and fluorometry. The analysis indicated 80% purity of the N 14 scFv, and 90% purity for the $V_H3$ clones, with approximately 2 molecules of FITC conjugated to each scFv molecule (F/P ratio of 2:1).

4.5.2 Binding activity following FITC labeling was assessed to verify retention of scFv specificity (see Example 5).

4.6 Biochemical characterization of phagemid clones: Several types of analysis were used to evaluate the structure and assess the purity of the various scFv preparations (see Example 8) including SDS-PAGE, mass spectroscopy (for Y1 and Y17 scFvs only), and HPLC. Western analysis and EIA were used for identifying the scFv; and FACS was used to characterize scFv binding.

Example 5

5. Binding Assays

The binding of the selected clones to cells was evaluated at two levels, the phagemid level and the soluble scFv level.

5.1 Binding at the Phagemid Level

To this end, a phagemid stock was prepared individually from each of the selected clones.

5.1.1 Colony test: In one set of experiments, a mixture of $10^9$ specific phagemids, derived from the biopanning protocol, which render infected E. Coli ampicillin resistant, and $10^{11}$ wild-type M13 phage, which do not carry ampicillin resistance and serve as a "blocker", was incubated with $10^5$ cells, chosen from a panel of cell types. Following incubation and washing, the bound phage were eluted with trypsin, and an aliquot was used to infect E. coli TG-I. The E. coli were then plated on 2×TY/AMP plates and incubated overnight at 30° C. The number of colonies obtained for each clone was calculated and compared. The results give a measure of the binding affinity and specificity of the phagemids.

5.1.2 White/Blue colony test: In this test, in which each experiment includes an internal control, the specific phagemid was mixed at the same ratio as in Section 5.1.1 above, i.e., 1/100, with another control phagemid designated pGEM7 (Promega Corp., Madison, Wis., USA). This pGEM7 phagemid carries resistance to ampicillin; however, it does not express any recombinant polypeptide at the N-terminus of its pIII gene. Following TG-1 infection and incubation on ampicillin plates containing 1 mM X-gal, colonies were enumerated. The colonies obtained containing pGEM7 are blue, whereas the colonies obtained from the specific phagemids are white. The enrichment factor, derived from the ratio of input/output of the white/blue colonies (grown on the same plate) for each test tube, was then calculated.

5.1.3 EIA of Phagemids 5.1.3.1 Phagemid binding to selected cells: Approximately $5 \times 10^5$ of the selected cells were fixed with acetone: methanol (1:1) on the surface of 24 well plates. The binding test required $10^9$ phagemids. Binding was carried out at 37° C. for 1 hr, followed by an extensive wash with PBS/Tween (0.05%). After extensive washing with PBS, the plates were incubated with rabbit anti-M13, anti-rabbit IgG-HRP and substrate. The intensity of the color produced was read by an ELISA plate reader, at $A_{405}$, and was proportional to the level of bound phagemids.

5.1.3.2 Phagemid binding to fixed platelets: Polystyrene microtiter plates were coated with $10^8$ fixed platelets and were incubated overnight, at 4° C. Approximately $10^{10}$ phagemids were used for evaluating binding. Washing and incubation of plates and determination of binding level were carried out as described in 5.1.3.1 above.

5.1.4 Binding assays to specific proteins, selected from the group consisting of human growth hormone (hGH), fibrinogen, fibronectin, BSA, SM (skim milk) and glycocalicin (proteolytic fragment of GPIb), were performed. Binding was assayed in the following manner. Polystyrene microtiter plate wells were coated with one of the proteins to be tested, at 2 µg/well. Coating was allowed to proceed during overnight incubation, at 4° C. Approximately $10^{10}$ phagemids were added to test binding. After extensive washing with PBS, the plates were incubated with rabbit anti-M13, anti-rabbit BRP, and substrate. The level of binding was measured by the intensity of color produced. The optical density was measured at $A_{405}$. Each sample was assayed in duplicate, and the average was calculated.

5.2 Binding Tests at the scFv level: Binding of the scFvs produced in the periplasm of HB2151 was compared in several cell types by two different assays, by EIA and by FACS analysis.

5.2.1 EIA of soluble scFv: Approximately $5 \times 10^5$ AML cells were incubated with 5–10 µg total protein. Binding was carried out at 4° C. for 1 hr, followed by EIA, using mouse anti-myc antibodies, anti-mouse HRP, and a substrate. Excess unbound antibodies were removed after each step by washing cells three times with PBS. The intensity of the color produced is read by an ELISA plate reader (O.D.$_{405}$). As above, the color intensity is proportional to the level of binding.

5.2.2 FACS Analysis of Cells 5.2.2.1 Analysis of cells stained by the "three-step staining" procedure: FACS analysis was performed to test and confirm the specificity of the selected clones. Initially, a "three step staining" procedure was established, using crude extracts or purified unlabeled scFv, followed by mouse anti-myc antibodies and, finally, FITC- or PE-conjugated anti-mouse antibodies.

FACS analysis requires 5–8×$10^5$ cells, which have been Ficoll-purified and resuspended in PBS+1% BSA. Binding was carried out for 1 hr at 4° C. After each step, cells were washed and resuspended in PBS+1% BSA. After the final staining step, cells were fixed by resuspending in PBS, 1% BSA, 2% formaldehyde, then read by FACS (Becton-Dickinson).

5.2.2.2 Staining of cells with FITC-labeled scFv, in a single staining step: FITC-labeled scFv was incubated with 5–8×$10^5$ Ficoll-purified cells in PBS+1% BSA. Binding was carried out for 1 hr at 4° C. Cells were then washed and fixed as in section 5.2.2.1 above, and read by FACS.

Example 6

Panning and Sequencing Results

6.1 Results of AM Protocol 6.1.1 Panning Results for AM Protocol: The estimated number of phagemids used for panning (input), and the estimated number of bound phagemids eluted in the AM protocol (output) are summarized in the following table (Table 1):

TABLE 1

| | | Panning results derived from protocol AM | | |
|---|---|---|---|---|
| Input stock | Cell source | Elution | Output | Amplfied stock |
| Nissim library- $2 \times 10^{11}$ | Membranes of AML | Bacterial TG-1 | $3 \times 10^4$ | T16M1 |
| T16MI - $10^{11}$ | Membranes of AML | Bacterial TG-I | $6.4 \times 10^3$ | T16M2 |
| T16M2 - $10^{11}$ | Membranes of AML | Bacterial TG-1 | $10^6$ | T16M3 |
| T16M3 - $10^{10}$ | AML cells | Trypsin | $2 \times 10^6$ | T16M3.1 |

Note the enrichment in the yield (output) obtained with each successive panning. In addition, there is no drop in the output when T16M3 was used to pan AML whole cells, suggesting that the bound phagemids are possibly specific for components on the external cell surface or that this specific system may contain a relatively high number of non-specific bound phagemids.

6.1.2 Clone Sequence Results for AM Protocol: Although clones were picked and sequenced from T16M1, T16M2 and T16M3 output stocks, the results presented below are mainly of those clones that were derived from the T16M3.1 output stock (AML intact cell panning). Clones AM10, AM11 and AM12 were identified in the T16M3 stock, but not in the subsequent output.

The amino acid sequences displayed in the $V_H$-CDR3 and their frequency in the tested clone output are summarized in Table 2 (SEQ ID NOS: 9–18, respectively, in order of appearance).

TABLE 2

Selected clones following AM biopanning protocol, from the T16M3 and T16M3.1 outputs.

| Clone # | $V_H$-CDR3 size | $V_H$-CDR3 sequence | | | | | | Germline | Frequency in T16M3 output | Frequency in T16M3.1 output |
|---|---|---|---|---|---|---|---|---|---|---|
| AM1 | 8 | Pro 1 | Trp 2 | Asp 3 | Asp 4 | Val 5 | Thr 6 | $V_H$3-DP47 | 5/31 | 8/51 |
| | | Pro 7 | Pro 8 | | | | | | | |
| AM2 | 12 | Gly 1 | Phe 2 | Pro 3 | Arg 4 | Ile 5 | Thr 6 | $V_H$3-DP46 | 11/31 | 20/51 |
| | | Pro 7 | Pro 8 | Ser 9 | Ala 10 | Glu 11 | Ile 12 | | | |
| AM3 | 5 | Gly 1 | Phe 2 | Pro 3 | Met 4 | Pro 5 | | $V_H$3-DP46 | 1/31 | 2/51 |
| AM6 | 10 | Gly 1 | Phe 2 | Pro 3 | His 4 | Ser 5 | Ser 6 | $V_H$3-DP46 | 4/31 | 6/51 |
| | | Ser 7 | Val 8 | Ser 9 | Arg 10 | | | | | |
| AM7 | 11 | Arg 1 | Phe 2 | Pro 3 | Met 4 | Arg 5 | His 6 | $V_H$3-DP46 | 3/31 | 4/51 |
| | | Glu 7 | Lys 8 | Thr 9 | Asn 10 | Tyr 11 | | | | |
| AM8 | 8 | Arg 1 | Phe 2 | Pro 3 | Pro 4 | Thr 5 | Ala 6 | $V_H$3-DP46 | 6/31 | 8/51 |
| | | Thr 7 | Ile 8 | | | | | | | |
| AM9 | 7 | Thr 1 | Gln 2 | Arg 3 | Arg 4 | Asp 5 | Leu 6 | $V_H$3-DP87 | 0/31 | 2/51 |
| | | Gly 7 | | | | | | | | |
| AM10 | 11 | Lys 1 | Phe 2 | Pro 3 | Gly 4 | Gly 5 | Thr 6 | $V_H$3-DP46 | 0/31 | 1/31 |
| | | Val 7 | Arg 8 | Gly 9 | Leu 10 | Lys 11 | | | | |

TABLE 2-continued

Selected clones following AM biopanning protocol, from the T16M3 and T16M3.1 outputs.

| Clone # | V$_H$-CDR3 size | V$_H$-CDR3 sequence | | | | | | Germline | Frequency in T16M3 output | Frequency in T16M3.1 output |
|---|---|---|---|---|---|---|---|---|---|---|
| AM11 | 12 | Gly | Phe | Pro | Val | Ile | Val | V$_H$3-DP49 | 0/31 | 1/31 |
| | | Glu | Gln | Arg | Gln | Ser | Thr | | | |
| | | 1 | 2 | 3 | 4 | 5 | 6 | | | |
| | | 7 | 8 | 9 | 10 | 11 | 12 | | | |
| AM12 | 10 | Arg | Phe | Pro | Gln | Arg | Val | V$_H$3-DP46 | 0/31 | 1/31 |
| | | Asp | Asn | Arg | Val | | | | | |
| | | 1 | 2 | 3 | 4 | 5 | 6 | | | |
| | | 7 | 8 | 9 | 10 | | | | | |

The amino acid sequence of $^{Arg}/_{Gly}$PhePro is present in seven of the ten isolated clones presented in Table 2, and represents a motif therein. In addition, note that the identified motif represents the N-terminal three amino acids of the CDR3 region in each case. Accordingly, this motif may be an effective anchor or binding site on its own or in combination with other amino acid residues extending beyond either one or both ends of the CDR3 region or as part of a larger peptide or polypeptide or Fv molecule.

Other CDR3 regions with high affinity for binding to AML cells may be constructed based on the core sequence $^{Arg}/_{Gly}$PhePro. They may be constructed by varying any of the above 5–12-mers by additions, deletions or mutations, while maintaining the $^{Arg}/_{Gly}$PhePro core sequence.

CDR3 regions of the invention have the amino acid sequence R1-$^{Arg}/_{Gly}$PhePro-R2, where R1 comprises 0–15 amino acids, preferably 0–9, most preferably 0–1 amino acid and R2 comprises an amino acid sequence from 1–15 amino acids, most preferably 1–9 amino acids. R1 and R2 are amino acid equences that do not adversely affect the specific binding of the $^{Arg}/_{Gly}$PhePro sequence to AML cells.

The CDR3 region of the light chain of the above clones is identical and is recited in SEQ ID NO: 125.

6.2 Results of YPR and YPNR Protocols 6.2.1 Panning Results for YPR and YPNR Protocols: The estimated number of phagmids used for panning (input) and the estimated number of bound phagmids eluted (output) are summarized in the following tables (Tables 3, 4).

TABLE 3

Panning results derived from the YPR protocol.

| Input stock | Elution | Output | Amplified stock |
|---|---|---|---|
| Nissim library 10$^{11}$ | Acid | 10$^7$ | R1(a) |
| | Trypsin | 4 × 10$^7$ | R1(t) |

TABLE 3-continued

Panning results derived from the YPR protocol.

| Input stock | Elution | Output | Amplified stock |
|---|---|---|---|
| Pooled [R1(a) - 10$^{12}$, + R1(t) - 10$^{12}$) | Acid | 5 × 10$^3$ | R2 |
| R2 - 10$^{12}$ | Acid | 3 × 10$^8$ | R3 |

Table 3 demonstrates that trypsin elution yields a 4-fold greater output as compared to acid elution in the first round.

Re-panning according to the YPNR protocol without the amplification step minimized the possibility of preferentially amplifying phagemid infection or bacterial infection. The resulting output is depicted in Table 4.

TABLE 4

Panning results derived from the YPNR protocol.

| Input stock | Elution | Output | Elution stock |
|---|---|---|---|
| Nissim librarY10$^{11}$ | Acid | 3 × 10$^7$ | YPNR1 |
| YPNT1-3 × 10$^7$ | Acid | 4 × 10$^5$ | YPNR2 |
| YPNR2-4 × 10$^5$ | Acid | 10$^3$ | YPNR3 |

As expected, the results presented in Table 4 show a decrease in phage yield after each round of panning. This protocol was used in order to prevent bias due to amplification of nonspecific phage.

6.2.2 Clone Sequence Results for YPR and YPNR Protocols:

Several clones from the third panning from both protocols were selected for sequencing. The amino acid sequences presented in Table 5 are those of the CDR3 regions of the heavy chain (V$_H$-CDR3). The germline and the frequency with which the sequences appeared in the R3 output are also indicated in this table (SEQ ID NOS: 8 and 19–24, respectively, in order of appearance).

TABLE 5

Selected Y-series clones following the YPR biopanning protocol with the R3 output.

| Clone # | V$_H$-CDR3 Size | V$_H$-CDR3 sequence | | | | | | | | | Germline | Frequency |
|---|---|---|---|---|---|---|---|---|---|---|---|---|
| Y1 | 6 | | Met | Arg | Ala | Pro | Val | Ile | | | VM-DP32 | 14/30 |
| | | | 1 | 2 | 3 | 4 | 5 | 6 | | | | |
| Y16 | 6 | | Thr | Gly | Gln | Ser | Ile | Lys | Arg | Ser | V$_H$3-DP26 | 1/30 |
| | | | 1 | 2 | 3 | 4 | 5 | 6 | 7 | 8 | | |
| Y17 | 6 | | Leu | Thr | His | Pro | Tyr | Phe | | | V$_H$3-DP32 | 7/30 |
| | | | 1 | 2 | 3 | 4 | 5 | 6 | | | | |
| Y-27 | 6 | | Leu | Arg | Pro | Pro | Glu | Ser | | | V$_H$3-DPS2 | 3/30 |
| | | | 1 | 2 | 3 | 4 | 5 | 6 | | | | |
| Y-44 | 11 | Thr | Ser | Lys | Asn | Thr | Ser | Ser | Ser | Lys | V$_H$3-DP32 | 2/30 |
| | | | Arg | His | | | | | | | | |
| | | | 1 | 2 | 3 | 4 | 5 | 6 | 7 | 8 | | |
| | | | 9 | 10 | 11 | | | | | | | |
| Y-45 | 12 | Arg | Tyr | Tyr | Cys | Arg | Ser | Ser | Asp | Cys | V$_H$3-DP49 | 1/30 |
| | | | Thr | Val | Ser | | | | | | | |
| | | | 1 | 2 | 3 | 4 | 5 | 6 | 7 | 8 | | |
| | | | 9 | 10 | 11 | 12 | | | | | | |
| Y-52 | 10 | | Phe | Arg | Arg | Met | Gln | Thr | Val | Pro | V$_H$3-DP49 | 1/30 |
| | | | Ala | Pro | | | | | | | | |
| | | | 1 | 2 | 3 | 4 | 5 | 6 | 7 | 8 | | |
| | | | 9 | 10 | | | | | | | | |

The majority of isolated clones from the YPNR protocol were Y1 as well.

The CDR3 region of the light chain of the above clones is identical and is recited in SEQ ID NO: 125.

Example 7

7. Results of Binding Evaluation 7.1 Binding of selected phagemid clones to AML cells (AM clone series): The binding assay for assessing phagemid binding to cells, the White/Blue colony test as described in Example 5, was performed with the AM clones. With the exception of clone AM7, no preferential binding to the tested cells was detected. Significant, but non-selective, binding of clone AM7 to all target cells, either as a phagemid or purified scFv, was observed. Results demonstrate no enrichment for the AM clone series.

7.2 Binding of Y Clone Series 7.2.1 Phagemid binding—EIA using fixed platelets: After three rounds of panning using two different protocols, phage clones were tested by EIA for binding to fixed platelets. Phagemid stock was prepared from each of the selected clones, and these clones were tested in two sets of EIA. Each sample was assayed in duplicate, and the average, was calculated. The results are summarized in FIG. I and indicate that six of the nine Y-series clones show a positive EIA reaction. The highest degree of binding was associated with clones Y1, Y16, Y17, and Y-27. Phage stocks M13 (wild-type bacteriophage) and E6 (selected on CLL leukemia cells) were used as negative controls. The dominant clone, phage Y1, showed the highest binding to fixed platelets and, together with Y17, showed significantly higher binding than M13 or E6 phage clones.

Example 8

8. Detailed Characterization of scFvs and Clone Binding 8.1 Structure and identification of scFv: The native structure of Y-I was assessed by HPLC analysis with a Superdex 75 column and by mass spectroscopy. Results of the former method indicate the presence of monomers, dimers, and tetramers in the preparation. Mass spectroscopy was sufficiently sensitive to identify the expected molecular weight of 26.5 kD and, in cases in which the c-myc tag was cleaved, a molecular weight of 24 kD was obtained.

Results of SDS-PAGE, however, indicate that the intact, non-cleaved molecule has an apparent molecular weight of 30 kD, despite the expected molecular weight is 26.5 kD, according to the nucleic acid sequence and to the mass spectroscopy results above. Western analysis using c-myc-specific antibodies confirmed the SDS-PAGE 30 kD results and supported the implication that the c-myc tag is present on the end of the intact molecule. The discrepancy between the results of the two procedures is due to the level of precision of the methods as well as the running conditions of SDS-PAGE that can alter the apparent molecular weight of the tested protein.

8.2 Binding of platelet-selected clones to leukemic cells: As noted in the introduction, platelet cell surface markers may be expressed on premature hematopoietic cells. The binding of platelet-selected clones was tested by FACS analysis. FACS analysis was performed after staining whole blood, followed by RBC lysis, or on Iso-prep- (Ficoll cushion) purified mononuclear cells. ScFvs were prepared from each clone, purified on protein-A, and FITC labeled (as described in Sections 4.1–4.4). In order to enable production of intact scFv in the non-suppressor E. coli strain HB2151, the amber codon (TAG) found in the V$_H$-CDR3 of the Y-27 clone was mutated by DNA site-directed mutagenesis to code for glutamic acid (GAG). The target cells for such studies were cells isolated from fresh blood samples of various patients with leukemia. The samples were obtained from three Medical Centers in Israel.

Clones Y1 and Y17 showed preferential binding to the leukemia cells tested whereas all the other Y-series clones gave binding at background levels only. Table 6 presents the binding of FITC-labeled Y-I and Y-17 to a variety of leukemic cells.

TABLE 6

Y-I binding specificity for leukemia cells.
B cell lineage

| ScFv | AML | CML | B-CLL | B-ALL | Multiple myeloma | T lineage leukemia | Normal lymphocytes |
|---|---|---|---|---|---|---|---|
| N14/C181 | 0/68 | 0/6 | 0/6 | 0/6 | 0/5 | 0/3 | 0/18 |
| Y1 | 54/68 | 2/6 | 1/6 | 3/6 | 4/5 | 2/3 | 0115 |
| Y17 | 3/3 | N.D.* | 1/1 | 2/2 | N.D.* | N.D.* | 11/11 |

*Not determined

The results, presented as fractions in Table 6, represent the fraction of patients, the cells of who were identified by FACS analysis as positively reacting with each tested antibody. The numerator represents the number of positive patients, with the denominator density the total number of patients tested for a given scFv/cell type combination. Y-17 bound strongly to all tested cells; this binding was thus considered to be non-cell selective. However, Y1 binding was found to be highly selective for several specimens of leukemic cells, especially those in the acute phase. Y1-scFv binding was further analyzed as described below.

Figure 3:
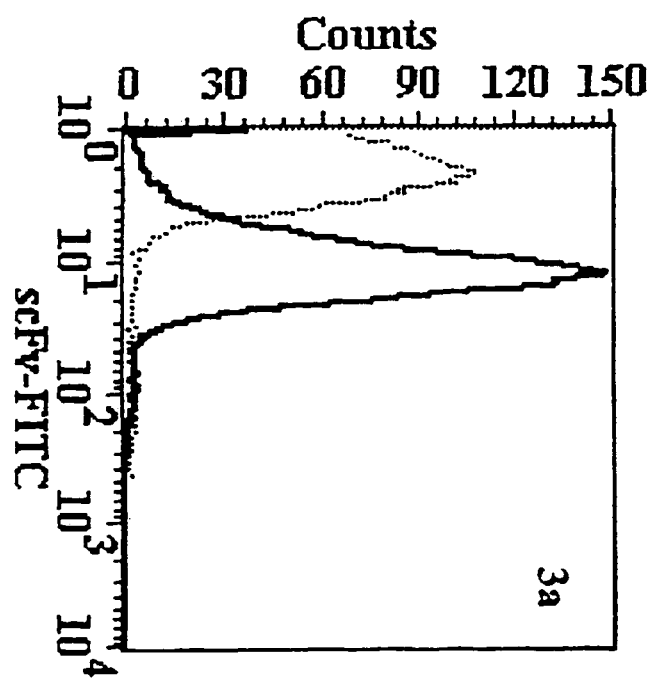
FIG. 3 presents the binding of Y-I to platelets (3a) and monocytes (3b) that have been Ficoll-purified, as determined by FACS analysis. Fluorescence intensity of cells bound by the two FITC-labeled tested samples (control scFv and scFv clone Y1) is presented.
Figure 3:
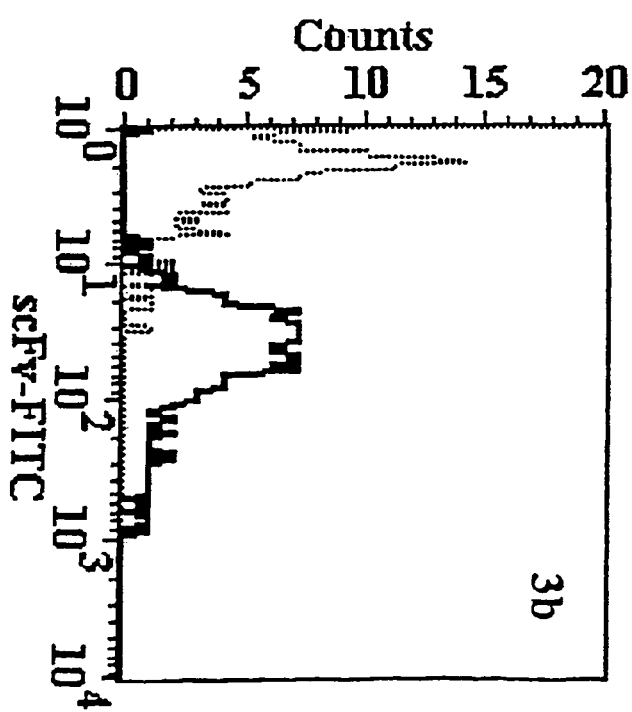

Representative results of YI binding to three AML samples are presented in FIG. 3. In each case, a large proportion of the cell population fluoresces at a significantly higher intensity than that of the background fluorescence obtained by staining with the negative control scFv. These results indicate that, for each patient, Y1 binds to a different fraction of the total cell population. The right-hand Y-I peak in each graph is believed to represent the minimum number of Y1-binding cells in the population, with the proportion of the total cells under this peak most likely representing the minimum proportion of YI-binding cells in each sample.

8.3 Binding of Y-I to normal blood cells: Y1 binding to Ficoll purified normal blood cells was analyzed according to the different blood cell types. Although no binding to normal lymphocytes was detected, Y1 bound to Ficoll purified monocytes from 9/28 subjects, platelets from 5/8 subjects, and red blood cells (RBC) from 1/4 subjects. However, CD14-specific antibodies bound to cells in all of the monocyte preparations and in many of the neutrophil preparations. A summary of this analysis is presented in Table 7.

TABLE 7

FACS analysis of scFv binding to Ficoll-purified normal blood dells.

| Antibody | Lymphocytes | Monocytes | Neutrophils | Platelets | RBCs |
|---|---|---|---|---|---|
| N14 | 0/18 | 0/4 | 0/4 | 0/3 | 0/4 |
| Y1 | 0/28 | 9/28 | 0/4 | 5/8 | 1/4 |
| CD14 | 0/15 | 14/14 | 8/14 | 0/5 | 0/4 |

These binding results represent the fraction of normal blood samples that were identified by FACS analysis as positively reacting with each tested antibody. Note that, although selected on fixed platelets, FITC-Y1 scFv shows relatively low binding affinity to platelets.

Figure 4:
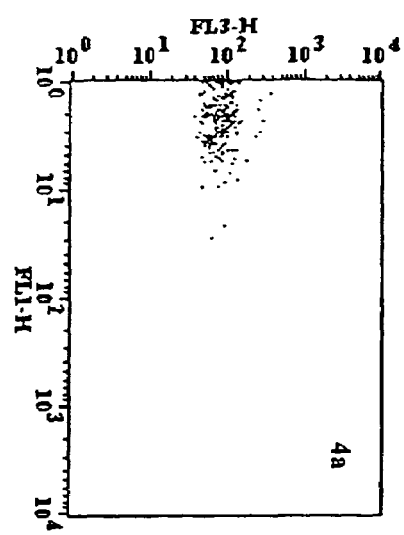
FIG. 4 presents the binding of FITC-labeled scFv clone Y1 to cord-blood CD34+ stem cells. CD34+ gated cells, in the FL3-H channel, were analyzed in the FLI-H channel for their binding to FITC-labeled negative control scFv (FIG. 4a) or FITC-labeled scFv clone Y1 (FIG. 4b).
Figure 4:
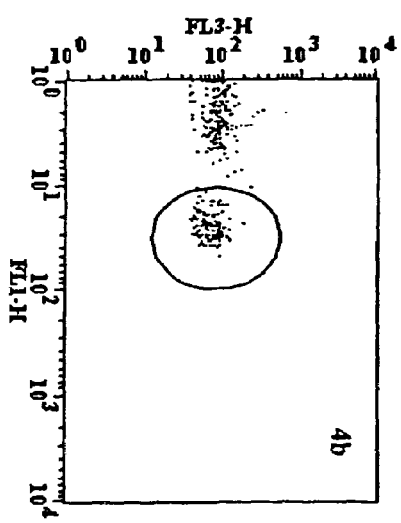
Figure 4:
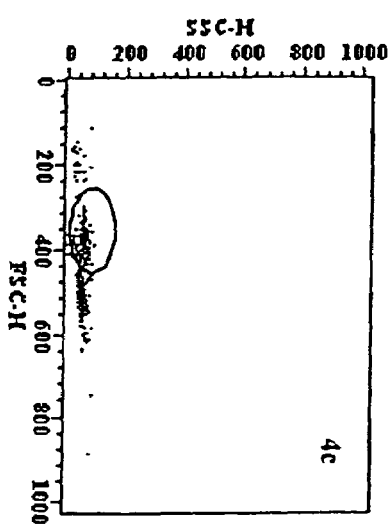
Figure 5:
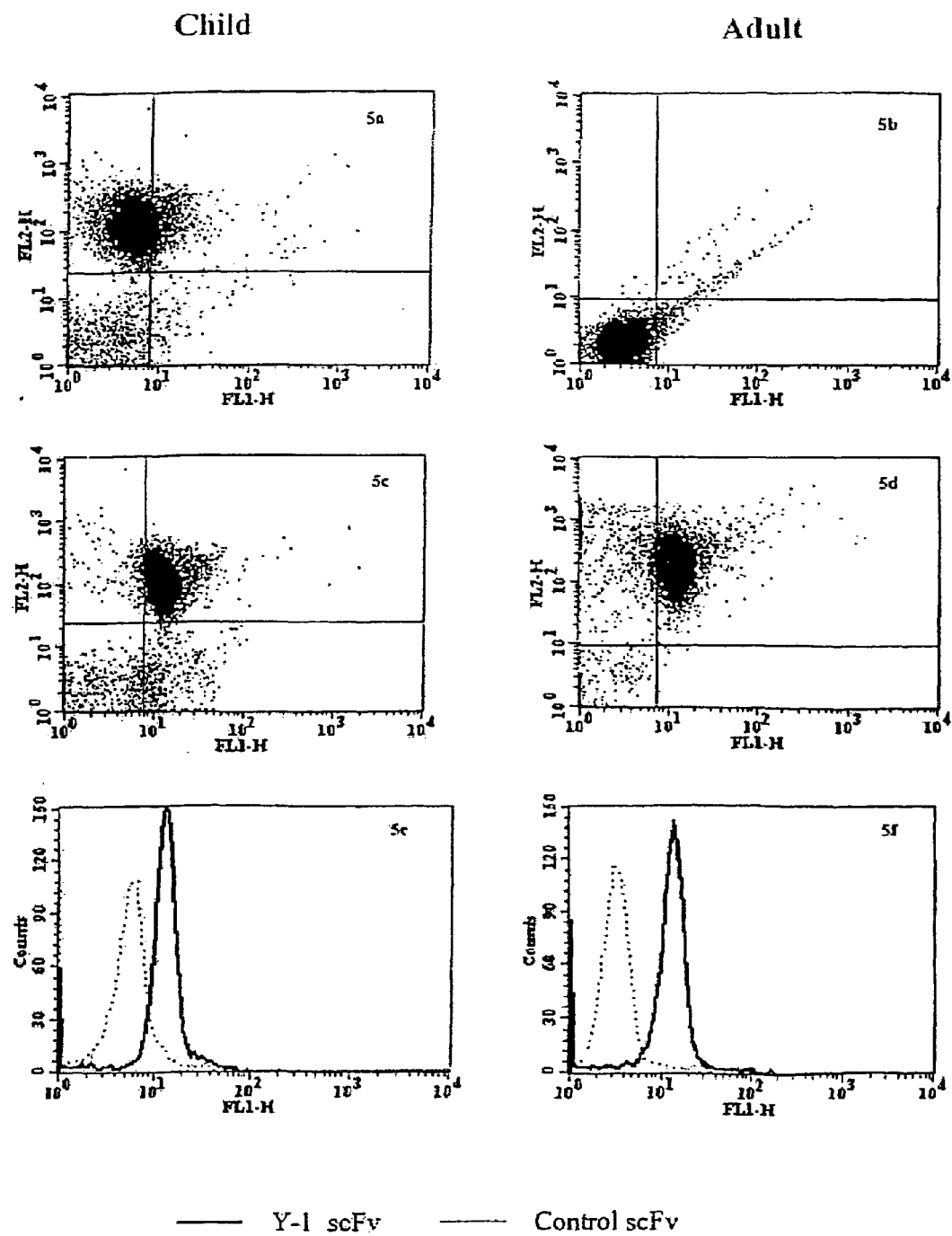
FIG. 5: FACS analyses of samples obtained from two patients with pre-B-ALL cells are presented: one from a child (5a, 5c, 5e) and the other from an adult (5b, 5d, 5f). A double staining procedure, using either a commercially available PE-labeled CD19 (a marker for normal peripheral B-cells.

FIG. 4 demonstrates the binding of Y1 to Ficoll-purified platelets (4a) and to monocyte-gated cells (4b). The shift on the monocyte cell population is greater than that observed on platelets, with a calculated mean fluorescence 30-fold and 5-fold greater, respectively, than the negative control. This observation is most probably due to the characteristic of platelets to adhere in multiples to Ficoll-purified monocytes. Subsequent experiments showed that, when assayed in whole blood samples, no Y1 binding was observed in any of the normal monocytes, granulocytes, platelets or RBC tested. Similarly, no Y1 binding to platelets was observed when derived from platelet-rich plasma (PRP). Under the same binding conditions (in whole blood, followed by RBC lysis with FACS lysing solution [Becton Dickenson]), Y1 bound to leukemia cells in a manner similar to that obtained after Ficoll purification. We may therefore conclude that, under natural conditions, the Y-I epitope on platelets or monocytes is hidden. During the Ficoll purification procedure the epitope is exposed, making it accessible for recognition by Y1, whereas for leukemic cells the epitope is exposed under both purified and non-purified conditions In addition to normal hematopoietic cell progenitors of the lymphatic and myeloid lineages, Y1 binding to hematopoietic stem cells (CD34+ cells) in cord blood was tested. FIG. 5 presents the binding results of FITC-labeled scFv clones to cord-blood CD34+ stem cells; FIG. 5a presents the results of binding of CD34+ gated cells to the FITC-labeled negative control scFv, and FIG. 5b presents the same analysis for binding of CD34+ gated cells to FITC-labeled scFv clone Y1. FIG. 5c presents a FSC and SSC dot plot analysis of the same FITC-labeled scFv clone Y-I sample as in 5b. Results of this analysis indicated the presence of two CD34+ stem cell sub-populations derived from cord blood, with differences in forward scatter (FSC) an indication of cell size. Y1 binds to the smaller sized cells of the two populations. The circled areas in FIGS. 5b and 5c delineate the sub-population of CD34+ cells that bind the clone Y1 scFv. Further analysis indicated that the smaller sized cells are dead cells that are present in the cell population, and Y1 binding may possibly indicate the presence of an intracellular ligand recognized by Y1.

The experiment was performed on peripheral blood cells of GM-CSF pre-treated healthy donors (GM-CSF treatment mobilizes stem cell release into the bloodstream) as well. Results similar to those presented in FIG. 5 were obtained.

8.4 Binding specificity of Y1 scFv compared to various cell markers on AML cells: Y1 staining of Ficoll-purified peripheral cells and bone marrow cells from AML patients was compared to staining of those cells by a panel of other antibodies. Results of such FACS analyses, for samples obtained from 14 patients, are summarized in Table 8. Note that there is significant variability in the frequency of stained cells in preparations from various individuals for all of the markers tested, including Y1. Lack of correlation between the binding of various markers and that of Y1 suggests that Y1 does not bind to any of the ligands that are bound by the other tested markers, and that the Y-I ligand does not constitute any of the tested sell surface markers.

TABLE 8

Comparison of Y1 scFv binding with binding of antibodies to various cell markers

| AML patient | Y1 | CD13 | CD14 | CD33 | CD34 | BN/PB** |
|---|---|---|---|---|---|---|
| 1 | 0 | ND | 2.5 | 47 | 4 | PB |
| 2 | 34 | 88 | 0 | 80 | 83 | PB |
| 3 | 66 | 100 | 20 | 87 | 9 | BM |
| 4 | 86 | 83 | 2 | 73 | 3 | BM |
| 5 | 100 | 100 | 0 | 100 | 0 | BM |
| 6 | 0 | 72 | 0 | 49 | 1 | BM |
| 7 | 59 | 20 | 93 | 100 | 0 | BM |
| 8 | 40 | 86 | 40 | 48 | 6.5 | BM |
| 9 | 70 | 75 | 67 | 75 | 1 | PB |
| 10 | 25 | 24 | 55 | 82 | 5 | PB |
| 11 | 26 | 76 | 17 | 83 | 52 | PB |
| 12 | 60 | 40 | 60 | 94 | ND | PB |
| 13 | 17 | ND | 13 | 75 | 15 | PB |
| 14 | 0 | 24 | 27 | 70 | 0 | BM |

**BM/PB-bone marrow/peripheral blood

The results are expressed as the percentage of cells in Ficoll-purified samples of a given patient, which was identified by FACS analysis as positively reacting with each individual antibody.

In light of the concentration of Y1 (~1 µg/5×10$^5$) required for binding detection, the results indicate that Y1 scFv has a relatively high binding affinity to the specific ligand on AML cells.

Figure 6:
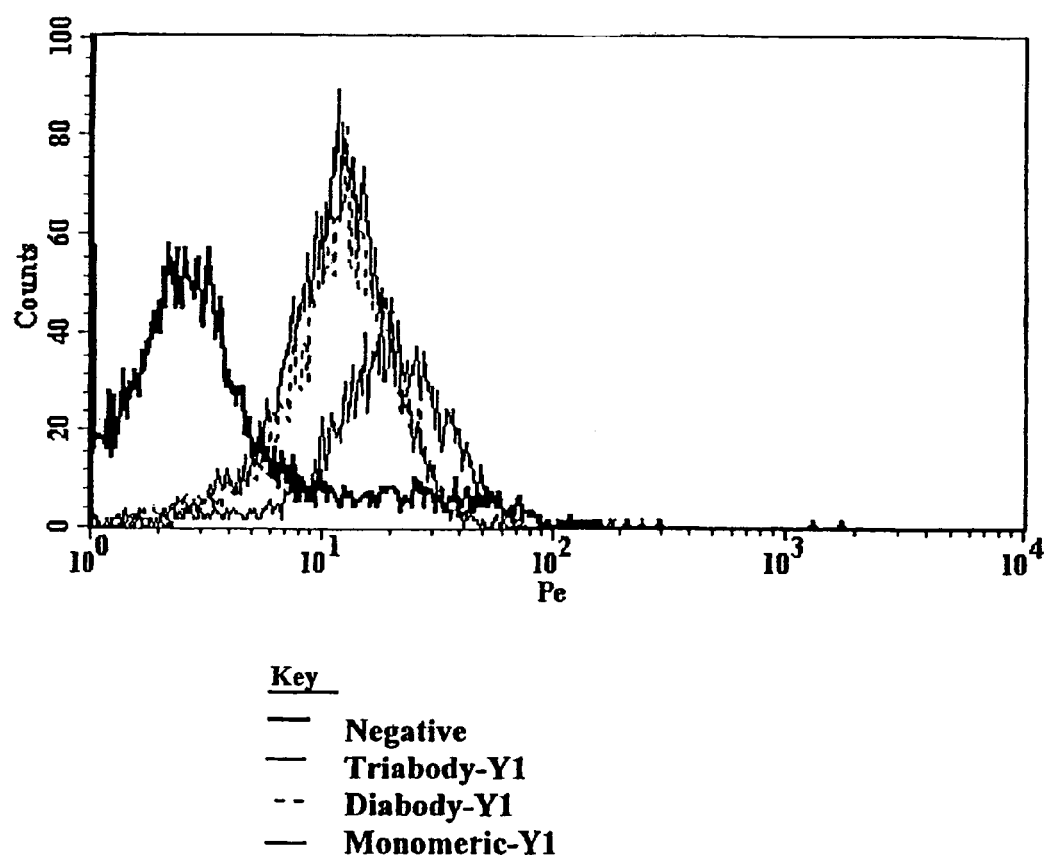
FIG. 6: This figure provides results of a binding comparison study performed using Jurkat cells. FACS analysis of binding to Jurkat cells of FITC-labeled Y-I scFv monomers, diabodies and triabodies, together with a negative control, is presented.

In addition to the results presented in Table 8, which show binding of Y1 to AML cells, we have shown above (Table 6) that Y1 can also bind to most other types of leukemia cells tested, including B-ALL cells, although the sample size for these other leukemia specimens was limited. FIG. 6 presents a FACS analysis of Y1 scFv binding to pre-B-ALL cells obtained from two patients. A double staining procedure, using either a commercially available PE-labeled CD 19 (a marker for normal peripheral B-cells; FIG. 6a, 6c) or a PE-labeled CD34 (a marker for stem cells; FIG. 6d) was employed, together with a FITC-labeled negative control scFv or FITC-labeled Y1 scFv. FIG. 6b is a double negative control. Fluorescence intensity (x-axis) of cells bound by the FITC-labeled sample (scFv clone Y1), relative to the negative control-staining pattern, is presented (6e and 6f). The results of FIG. 6 demonstrate that most of the leukemic, pre-B-ALL cells within each of the two samples tested are positive for Y1 cell staining due to Y-I binding.

8.5 Binding of Y1-scFv to cell Lines: Several cell lines-.derived from malignant hematopoietic lineages were screened for their ability to be recognized by Y1. FACS analysis indicates that Y1 binds to many of the tested cells (Table 9). Note that only one human B-cell line and one mouse myeloid cell line was tested. Importantly, this binding was restricted to exponentially growing cells. Cells in stationary phase generally did not bind to Y1, indicating that Y1 ligand expression is regulated during the life cycle of the cells. Additionally, binding strength differs among the reacting cells. This observation implies that there are differences in expression levels or in affinity of the ligand in different cells.

TABLE 9

Binding Of Y1 To Hematopoietic Cell Lines

| Type | High Reactive | Medium Reactive | Low Reactive |
|---|---|---|---|
| Human Myeloid | KG-1; THP-1; U937; Tf-1; MEG | HL-60; HEL; K-562; MC1010 | NB-4 |
| Human B-cell | | | Namalwa; Daudi; UMUC3, RAJI |
| Human T-cell | Jurkat; Hs-602 | CCRF-CEM; Molt-4; Hut-78; | |
| Mouse Myeloid | | | M1; P388D1; PU5-1.8; WEHI-274.1 |

8.6 Binding of Y1 purified in the presence of DTT: Once the Y1 clone was selected, the process for producing the scFv was further developed. Results of FTLC analysis of the Y1 batches indicated that the protein may multimerize with mainly monomers and tetramers forming, the ratio between the two forms differing from one preparation to the next. In order to obtain homogeneous material, 5 mM DTT was added during the affinity purification on Protein-A sepharose column, followed by removal by PBS buffer exchange. Indeed, after DTT treatment, most (>90%) of the material was found in the monomeric fraction. No significant difference was found between the binding of the monomeric form of Y1 (purified in the presence of DTT and analyzed on HPLC) and the binding of the mixture of Y1 forms.

8.7 Y1 is a specific clone to leukemia cells: The Y1 cassette belongs to the $V_H$-DP32 germline. Several other clones, originating from the same germline, were isolated and are detailed in Example 6. These clones include Y17, Y-27, and Y-44. The primary sequences (i.e., germline cassette) of all these clones differ in their CDR3 regions only. However, only Y1 shows selectivity to leukemic cells. The CD3 sequences of these clones are summarized in Table 10, and the binding profiles of the clones are summarized in Table 11 (SEQ ID NOS: 8 and 20–22, respectively, in order of appearance).

TABLE 10

The CDR3 sequence of $V_H$3-DP32 isolated clones

| Clone # | $V_H$-CDR3 sequence | | | | | | Germline |
|---|---|---|---|---|---|---|---|
| Y1 | Met | Arg | Ali | Pro | Val | Ile | $V_H$3-DP32 |
| | 1 | 2 | 3 | 4 | 5 | 6 | |
| Y17 | Leu | Thr | His | Pro | Tyr | Phe | $V_H$3-DP32 |
| | 1 | 2 | 3 | 4 | 5 | 6 | |
| Y-27 | Leu | Arg | Pro | Pro | Glu | Ser | $V_H$3-DP32 |
| | 1 | 2 | 3 | 4 | 5 | 6 | |

TABLE 10-continued

The CDR3 sequence of V$_H$3-DP32 isolated clones

| Clone # | V$_H$-CDR3 sequence | | | | | | | | | | | Germline |
|---|---|---|---|---|---|---|---|---|---|---|---|---|
| Y-44 | Thr | Ser | Lys | Asn | Thr | Ser | Ser | Ser | | | | V$_H$3-DP32 |
|  |  | Lys | Arg | His |  |  |  |  |  |  |  |  |
|  | 1 | 2 | 3 | 4 | 5 | 6 | 7 | 8 |  |  |  |  |
|  |  | 9 | 10 | 11 |  |  |  |  |  |  |  |  |

TABLE 11

Binding profile of V$_H$3-DP32 isolated clones

| Clone # | Binding specificity. |
|---|---|
| Y1 | Binds to many lukemia cells. |
| Y17 | Binds to all tested hematopoeitic cells, including normal lymphocytes. |
| Y-27 | Does not bind to any of the hematopoietic cells tested. |
| Y-44 | Does not bind to any of the hematopoietic cells tested. |

Tables 10 and 11 indicate that, although the primary sequences are identical among the four clones with the exception of the V$_H$-CDR3 region, the binding profiles differ significantly from one clone to another. This observation reinforces the concept that the sequence of the V$_H$-CDR3 region plays an important role in the specificity of the binding site to the antigen. Note that neither the length of the CDR3 sequence nor the specific germfirie cassette in which it is placed appears to be a primary determinant of binding specificity. Y17 and Y-27 each comprises a 6-mer CDR3, as does Y1, and heavy chains of all three clones are derived from the identical germline. In the case of Y17 and Y-27, selective binding to hematopoietic cells has not been demonstruted.

Example 9

9.1 Construction of triabodies: The vector pHEN-Y1, encoding the original Y1, was amplified using PCR for both the V$_L$ and the V$_H$ regions, individually. The sense oligonucleotide 5'-AACTCGAGTGAGCTGACACAGGACCCT (SEQ ID NO: 213), and the anti-sense oligonucleotide 5'-TTTGTCGACTCATTTCTTTTTTGCGGCCGCACC (SEQ ID NO: 214) were used for the V$_L$ PCR reaction. The cDNA product of the expected size of ~350 bp was purified, sequenced, and digested with XhoI and NotI restriction enzymes.

The same procedure was employed to amplify the V$_H$ region (using the sense oligonucleotide 5'-ATGAAATAC-CTATTGCCTACGG (SEQ ID NO: 215) and anti-sense oligonucleotide 5'-AACTCGAGACGGTGACCAGGG-TACC) (SEQ ID NO: 216). The V$_H$ PCR product was digested with NcoI and XhoI restriction enzymes. A triple ligation procedure into the pHEN vector, pre-digested with NcoI-NotI, was employed. The final vector was designated pTria-Y1.

Following E. coli transformation, several clones were picked for further analysis, which included DNA sequencing, protein expression, and extraction from the periplasmic space of the bacteria. SDS-PAGE under reducing conditions and Western blot analysis were performed to confirm the size of the Y1 triabodies.

9.2 Construction of Diabodies

The pTria-Y1 vector from above was linearized with XhoI restriction enzyme, and synthetic complimentary double stranded oligonucleotides (5'-TCGAGAGGTGGAG-GCGGT (SEQ ID NO: 217) and 5' TCGAACCGCCTC-CACCTC) (SEQ ID NO: 218) were pre-annealed and ligated into the XhoI site, between the Y1-heavy and Y1-light chains. This new vector was designated pDia-Y1. As described for the triabodies, the DNA sequence and protein expression was confirmed.

9.3 Expression and Purification of Diabodies and Triabodies

Expression in E-coli was essentially as described above for the scFv-Y1. However, the purification of Y1 diabodies and triabodies from the periplasm of the transformed E.coli cells was different. The scFv Y1 monomer form can be purified on an affinity column of Protein-A Sepharose beads. Multimeric forms of Y1 are, however, ineffectually purified by this procedure. Therefore, periplasmic proteins extracted from the bacteria were precipitated over-night with 60% ammonium sulfate, resuspended in $H_2O$, and loaded onto a Sephacryl-200 (Pharmacia) size exclusion column pre-equilibrated with 0.1×PBS. Fractions were collected and analyzed by HPLC, and separate fractions containing either the dimer or timer forms were collected for FITC labeling and FACS analysis.

9.4 Binding of Y1 Diabodies and Triabodies to Cells

FACS analysis was performed on Jurkat cells using a "three step staining procedure." First, crude extracts or purified unlabeled scFv are stained, then mouse anti-myc antibodies, and finally, FITC- or PE-conjugated anti-mouse antibodies. FACS analysis requires $5-8 \times 10^5$ cells, which have been Ficoll-purified and resuspended in PBS+1% BSA. Binding was carried out for 1 hour at 4° C. After each step, cells were washed and resuspended in PBS+1% BSA. After the final staining step, cells were fixed by re-suspending in PBS, 1% BSA, 2% formaldehyde, and then read by FACS (Becton-Dickinson).

Figure 7:
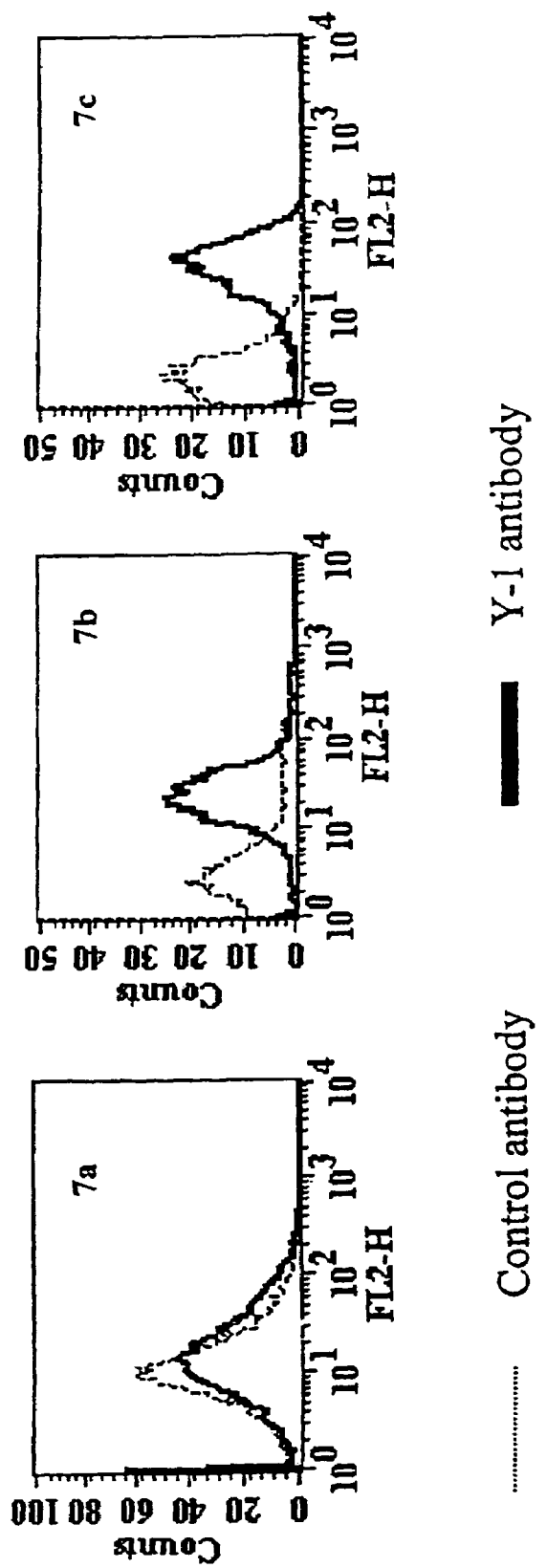
FIG. 7: This figure provides results of a study comparing the binding of IgG- Y-I and scFv-Y1. A double staining procedure was employed to compare the binding of full sized IgG-Y1 to that of the scFv-YI form. Five nanograms of IgG-YI were used for FACS analysis on RAJI cell (YI negative cells.
Figure 8:
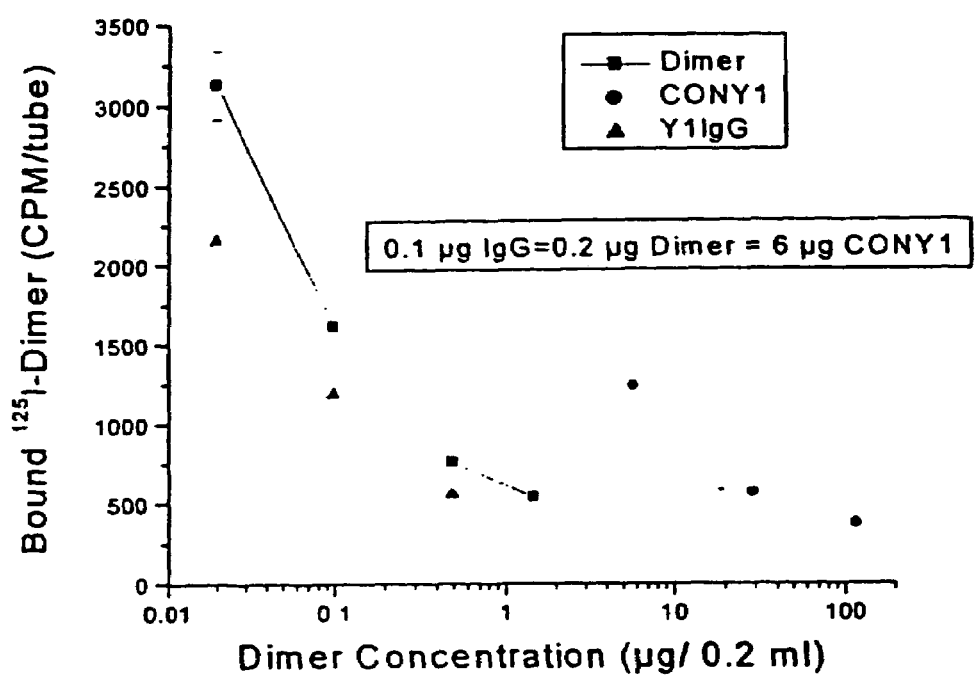
FIG. 8: This figure shows a binding comparison between a YI dimer, the Y1 scFv (CONY1), and Y1 IgG.
Figure 9:
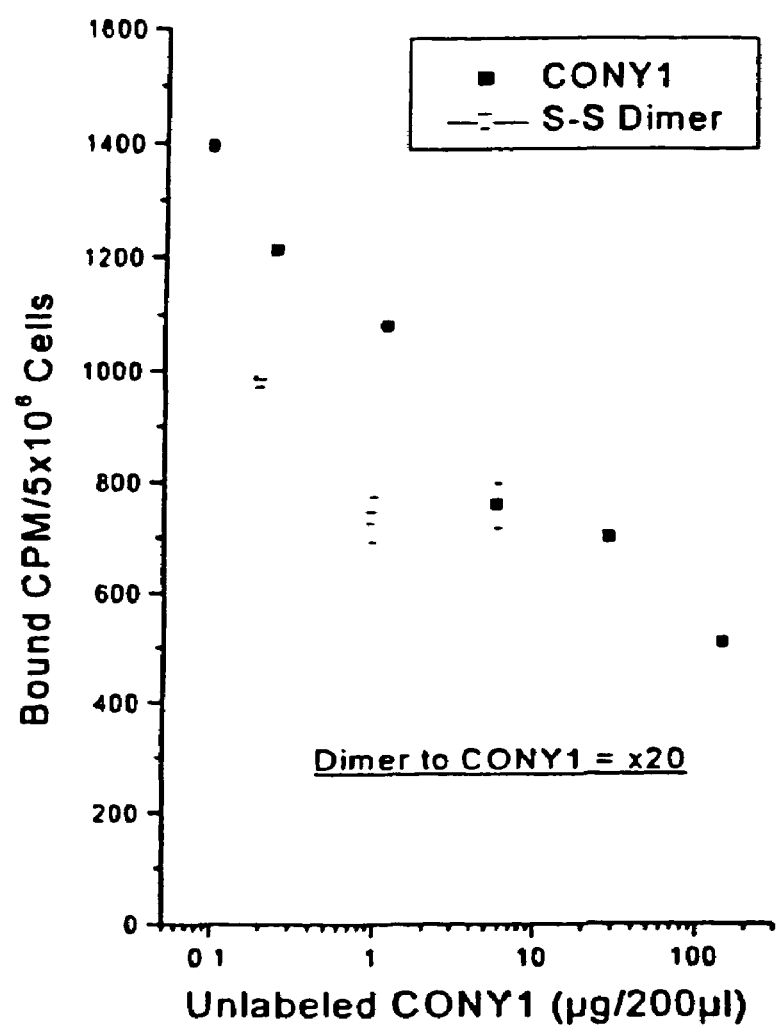
FIG. 9: This figure shows a binding comparison between a Y1 sulfide bridge dimer with the Y1 scFv (CONY1).

The binding of Y1-scFv was compared to that of diabodies and triabodies. In this analysis (FIG. 7, the binding profile of all three forms was very similar, indicating that the above modifications in the molecule did not alter, conceal or destroy the apparent binding affinity of Y1 to its ligand.

Production of Y1-cys-KAK (Cysteine Dimer)

One liter of λpL-y1-cys-KAK bacterial culture was induced at 42° C. for 2–3 hrs. This culture was centrifuged at 5000 RPM for 30 minutes. The pellet was resuspended in 180 ml of TE (50 mM Tris-HCl pH 7.4, 20 mM EDTA). 8 ml of lysozyme (from a 5 mg/ml stock) was added and incubated for 1 hr. 20 ml of 5M NaCl and 25 ml of 25% Triton was added and incubated for another hour. This mixture was centrifuged at 13000 RPM for 60 minutes at 4° C. The supernatant was discarded. The pellet was resuspended in TE with the aid of a tissuemiser (or homogenizer). This process was repeated 3–4 times until the inclusion bodies (pellet) were gray/light brown in color. The inclusion bodies were solubilized in 6M Guanidine-HCl, 0.1M Tris pH 7.4, 2 mM EDTA (1.5 grams of inclusion bodies in 10 ml solubilization buffer provided ~10 mg/ml soluble protein). This was incubated for at least 4 hrs. The protein concentration was measured and brought to a concentration of 10 mg/ml. DTT was added to a final concentration of 65 mM and incubated overnight at room temperature. Re-folding was initiated by dilution of 10 ml of protein (drop by drop) to a solution containing 0.5 M Arginine, 0.1 M Tris pH 8, 2 mM EDTA, 0.9 mM GSSG. The re-folding solution was incubated at ~10° C. for 48 hrs. The re-folding solution containing the protein was dialyzed in a buffer containing 25 mM Phosphate buffer pH 6, 100 mM Urea, and concentrated to 500 ml. The concentrated/dialyzed solution was bound to an SP-sepharose colunm, and the protein was eluted by a gradient of NaCl (up to 1M).

9.6 A Study of the Affinity of the S-S Y1-Dimer in Comparison to CONY1 and Y1-IgG, using a Radioreceptor Binding Assay (RRA) with KG-1 Cells The assay system involved the use of radioactive ligands that were prepared by iodination with $^{125}$I using chloramine T on the Y1-IgG construct or the Bolton-Hunter reagent on the CONY1 (the Y1 scFv) construct. The assay tubes contained $5\times10^6$ KG-1 cells per 0.2 ml and a labeled tracer with varying amounts of unlabeled competitor, in PBS+ 0.1% BSA, pH 7.4. After 1-hour incubation with agitation at 4° C., the cells were thoroughly washed with cold buffer and taken for radioactivity counting.

In the RRA study using labeled Y1-IgG, a 2 ng/tube of $^{125}$I-Y1-IgG was used, and competition was performed with each of the three molecules. The results are provided in FIG. 8. This results presented in this figure demonstrate that the affinity of the S-S Y1 dimer was 30 times higher than that of CONY1. A rough estimate of the affinity of the Y1-IgG in this experiment is $2\times10^{-8}$M. The corresponding affinity of the dimer is, therefore, $4\times10^{-8}$ M.

In a second RRA using labeled CONY1, a 100 ng/tube of $^{125}$I-Y1-IgG was used, and competition was performed with each of the three molecules. The results are provided in FIG. 9. This figure shows that the affinity of the S-S dimer was 20 times higher than that of CONY1. A rough estimate of the affinity of CONY1 in this experiment is $10^{-6}$M. The corresponding affinity of the dimer is, therefore, $5\times10^{-8}$ M.

9.7 ELISA to GC (Glycocalicin)

100 μl of purified glycocalicin was incubated in a 96 flat well maxisorp plates, overnight at 4° C. The plate was washed with PBST (PBS+0.05% tween) 3 times, then 200 ml of PBST-milk (PBST+2% Non fat milk), for 1 hr at room temperature. The plate was washed with PBST, and the monomer or dimer (100 μl) was added in PBST-milk at different concentrations for 1 hr at room temp. Then the plate was washed and anti-$V_L$ polyclonal (derived from immunized rabbits with $V_L$ derived from Y1) (1:100 diluted in PBST-milk) was added for an hour. The plate was washed and anti-rabbit HRP was added for an additional hour. The plate was washed 5 times and 100 μl TMB substrate was added for approximately 15 minutes then 100 μl of 0.5 $H_2SO_4$ was added to stop the reaction. The optical density of the plate was measured at 450 nm in an ELISA reader.

9.8 Y1 Reactivity with Recombinant Glycocalicin (GC) Expressed in Prokaryotic (*E. coli*) System The DNA fragment encoding the N-terminal soluble part of human platelet GP1b-glycocalicin (GC, amino acid 1 to amino acid 493) was cloned into an IPTG inducible prokaryotic vector cassette. *E. coli* (BL21 DE3) cells harboring the newly constructed plasmid were grown at 37° C. to O.D. 0.7–0.8, than at 37° C. for 3 hours for in the presence of IPTG for induction. SDS-polyacrylamide gel loaded either with natural semi-purified human platelet derived GC or with *E. coli* cell lysates (total protein content) derived from induced and non-induced cells were analyzed. Western blot analysis was performed with scFv Y1-biotinylated, polyclonal rabbit anti-human GC antibody, commercially available mouse anti human CD42 monoclonal antibody (SZ2 Immunotech, PM640 Serotec, HIP1 Pharmigen, AN51 DAKO) and polyclonal antibody against the N-terminus of gpIba (Sc-7071, Santa Cruz). The two polyclonal antibodies recognized both the recombinant bacterial derived GC as well as the natural human platelet derived GC. The scfv Y1 and the commercially available antibodies recognized only the natural human derived GC, but not the bacterial derived recombinant platelet GC.

Post-translational modification, such as glycosilation and sulfation is essential for scFv and commercially available antibodies binding to GC. The prokaryotic (*E.coli*) system lacks post-translation modification mechanisms, such as glycosilation and sulfation.

9.9 Making Tetramers of Y1

A construct was designed where the following sequence, LNDIFEAQKIEWHE (SEQ ID NO: 219), was added at the C-terminus of the Y1 by PCR and cloning into an IPTG inducible expression vector cassette. The clone was named Y1-biotag. This sequence is a substrate for the enzyme BirA, that in the presence of free biotin, the enzyme is capable of covalently connecting biotin to the lysine (K) residue (Phenotypic analysis of antigen-specific T lymphocytes. Science. 1996 October 4;274(5284):94–6, Altman J D et al). This construct was produced as inclusion bodies in BL21 bacterial cells. Refolding was performed as described previously. Inclusion bodies were solubilized in guanidine-DTT. Refolding was done by dilution in a buffer containing arginine-Tris-EDTA. Dialysis and concentration was performed followed by HiTrapQ ionic exchange purification.

The purified Y1-biotag scFv was incubated with BirA enzyme (purchased from Avidity) and biotin as recommended by the provider. The biotinylated Y1-biotag was analyzed by HABA test (that estimates the amount of biotin per molecule) and demonstrated that there was around >0.8 biotin residues/molecule.

The Y1-biotag biotinylated was incubated with Streptavidin-PE (Phycoerytrin) to form complexes and used in FACS experiments using KG-1 cells (positive for Y1). Streptavidin can bind up to 4 biotinilated Y-1-biotag molecules. The sensitivity of the binding was increased at least 100 fold due to the increase in avidity.

The sequence of Y1-biotag is as follows (SEQ ID NO: 220):

```
  1 MEVQLVESGG GVVRPGGSLR LSCAASGFTF DDYGMSWVRQ
 41 APGKGLEWVS GINWNGGSTG YADSVKGRFT ISRDNAKNSL
 81 YLQMNSLRAE DTAVYYCARM RAPVIWGQGT LVTVSRGGGG
121 SGGGGSGGGG SSELTQDPAV SVALGQTVRI TCQGDSLRSY
161 YASWYQQKPG QAPVLVIYGK NNRPSGIPDR FSGSSSGNTA
201 SLTITGAQAE DEADYYCNSR DSSGNNVVFG GGTKLTVLGG
241 GGLNDIFEAQ KIEWHE
```

Example 10

Construction of Full Sized Y1-IgGI

Whole IgG molecules have several advantages over the Fv forms, including a longer half-life in vivo and the potential for inducing an in vivo cellular response, such as those mediated by ADCC or CDC (complement dependent cytotoxicity; Tomlinson, *Current Opinions of Immunology,* 5, 83–89(1993)). By a molecular cloning approach that is described below, we have converted the Y1 Fv regions into full sized IgGI molecules. Y1-IgG1 construction was accomplished by joining fragments of cDNA to each other in the following order:

10.1 A leader sequence compatible for a mammalian expression system: An exchangeable system was designed to allow convenient insertion of elements required for a full IgG molecule. The following complimentary double stranded oligonucleotides encoding a putative leader sequence were synthesized, annealed, and ligated into the XhoI site of mammalian expression vector (under the SRα5 promoter).

```
5'-
TCGACCTCATCACCATGGCCTGGGCTCTGCTGCTCCTCACCCTCCTCACT
CAGGACACAGGGTCCTGGGCCGAT
and 5'-
GATCGATTGCACCAGCTGGATATCGGCCCAGGACCCTGTGTCCTGAGTG
AG GAGGGTGAGGAGCAGCAGCCCAGGCCATGGTGATGAGG.
```

Upstream of the initiation ATG codon, two Kozak elements were included. In addition, an internal EcoRV site was introduced between the putative cleavage site of the leader sequence and the XhoI site to allow subcloning of the variable regions. This modified vector was designated pBJ-3. At paragraph 395:

10.2 The $V_L$ encoding sequence derived from the Y1 scFv cDNA sequence was inserted between the leader and the constant light region-encoding sequence. Similarly, the $V_H$ encoding sequence derived from the Y1 scFv cDNA sequence was inserted between the leader and the constant heavy region-encoding sequence. This was accomplished by PCR amplification of the vector pHEN-Y1, encoding for the original Y1, to obtain the $V_L$ and the $V_H$ regions, individually.

10.3 The oligonucleotides 5'-TTTGATATCCAGCTG-GTGGAGTCTGGGGGA (sense) (SEQ ID NO: 223) and 5'-GCTGACCTAGGACGGTCAGCTTGGT (anti-sense) (SEQ ID NO: 224) were used for the $V_L$ PCR reaction. The cDNA product of the expected size of ~350 bp was purified, sequenced and digested with EcoRV and AvrII restriction enzymes. The same procedure was employed to amplify and purify the $V_H$ cDNA region, using the sense and the anti-sense oligonucleoitides 5'-GGGATATCCAGCTG(C/G)(A/T)GGAGTCGGGC (SEQ ID NO: 225) and 5'-GGACTC-GAGACGGTGACCAGGGTACCTTG, respectively (SEQ ID NO: 226).

10.4 Constant regions: The constant λ3 (CL-λ3) region and the constant heavy regions CH1-CH3 derived for IgG1 cDNA were individually synthesized as follows:

10.4.1 For the constant CL-λ3 region, RT-PCR was performed on mRNA extracted from a pool of normal peripheral B-cells (CD 19+cells) in combination with the sense 5'-CCGTCCTAGGTCAGCCCAAGGCTGC (SEQ ID NO: 227) and the anti-sense 5'-TTTGCGGCCGCTCAT-GAACATTCTGTAGGGGCCACTGT (SEQ ID NO: 228) oligonucleotides. The PCR product of the expected size (~400 bp) was purified, sequenced, and digested with AvrII and NotI restriction enzymes.

10.4.2 For the constant IgGI regions (γ chain), a human B cell clone (CMV - clone #40), immortalized at BTG, was selected for PCR amplification. This clone was shown to secrete IgG1 against human CMV and was also shown to induce ADCC response in in-vitro assays. For the CH1-CH3 cDNA, oligonucleotides 5'-CCGCTCGAGTGC(T/C)TC-CACCAAGGGCCCATC(G/C)GTCTTC (sense) (SEQ ID NO: 229) and 5'-TTTGCGGCCGCTCATTTACCC(A/G)GAGACAGGGAGAGGCT (anti-sense) (SEQ ID NO: 230) were synthesized and used for PCR amplification. As described for the CL cDNA encoding sequence, the PCR product of expected size (~1500 bp) was purified, sequenced, and digested with AvrII and NotI restriction enzymes.

10.5 For the final expression vectors, a triple ligation procedure was carried out using the EcoRV-NotI pre-digested vector, EcoRV-AvrII variable cDNAs and AvrII-NotI constant regions. The final vectors for heavy chain and light chain expression were designated Y-I-HC and Y1-LC, respectively.

10.6 An additional vector, pBJ-Y1-LP, was constructed based on the Y1-LC to allow double selection based on the puromycin resistant gene (PAC). In this vector the neomycin-resistant gene of the Y1-LC plasmid was replaced with a fragment of ~1600 bp encoding for the PAC gene (from the pMCC-ZP vector).

10.7 The open reading frame (ORF) of both the Y-1-IgG-HC and Y1-IgG-LC and their encoded amino acid sequences are presented below:

10.7.1 The ORF of Y1-IgG-HC ($V_H$, $C_H1$ $C_H2$ $C_H3$) (SEQ ID NO 231 and 26, respectively)

```
  1   ATGGCCTGGGCTCTGCTGCTCCTOACCCTCCTCACTCAGGACACAGGGTCCTGGGCCGAT
  1    M   A   W   A   L   L   L   L   T   L   L   T   Q   D   T   G   S   W   A   D

61   ATCCAGCTGGTGGAGTCTGGGGGAGGTGTGGTACGGCCTGGGGGGTCCCTGAGACTCTCC
 21    I   Q   L   V   E   S   G   G   G   V   V   R   P   G   G   S   L   R   L   S

121   TGTGCAGCCTCTGGATTCACCTTTGATGATTATGGCATGAGCTGGGTCCGCCAAGCTCCA
 41    C   A   A   S   G   F   T   F   D   D   Y   G   M   S   W   V   R   Q   A   P

181   GGGAAGGGGCTGGAGTGGGTCTCTGGTATTAATTGGAATGGTGGTAGCACAGGTTATGCA
 61    G   K   G   L   E   W   V   S   G   I   N   W   N   G   G   S   T   G   Y   A

241   GACTCTGTGAAGGGCCGATTCACCATCTCTAGAGACAACGCCAAGAACTCCCTGTATCTG
 81    D   S   V   K   G   R   F   T   I   S   R   D   N   A   K   N   S   L   Y   L
```

```
301 CAAATGAACAGTCTGAGAGCCGAGGACACGGCCGTGTATTACTGTGCAAGAATGAGGGCT
101  Q   M   N   S   L   R   A   E   D   T   A   V   Y   Y   C   A   R   M   R   A

361 CCTGTGATTTGGGGCCAAGGTACCCTGGTCACCGTCTCGAGTGCTTCCACCAAGGGCCCA
121  P   V   I   W   G   Q   G   T   L   V   T   V   S   S   A   S   T   K   G   P

421 TCGGTCTTCCCCCTGGCACCCTCCTCCAAGAGCACCTCTGGGGGCACAGCGGCCCTGGGC
141  S   V   F   P   L   A   P   S   S   K   S   T   S   G   G   T   A   A   L   G

481 TGCCTGGTCAAGGACTACTTCCCCGAACCGGTGACGGTGTCGTGGAACTCAGGCGCCCTG
161  C   L   V   K   D   Y   F   P   E   P   V   T   V   S   W   N   S   G   A   L

541 ACCAGCGGCGTGCACACCTTCCCGGCTGTCCTACAGTCCTCAGGACTCTACTCCCTCAGC
181  T   S   G   V   H   T   F   P   A   V   L   Q   S   S   G   L   Y   S   L   S

601 AGCGTGGTGACCGTGCCCTCCAGCAGCTTGGGCACCCAGACCTACATCTGCAACGTGAAT
201  S   V   V   T   V   P   S   S   S   L   G   T   Q   T   Y   I   C   N   V   N

661 CACAAGCCCAGCAACACCAAGGTGGACAAGAGAGTTGAGCCCAAATCTTGTGACAAAACT
221  H   K   P   S   N   T   K   V   D   K   R   V   E   P   K   S   C   D   K   T

721 CACACATGCCCACCGTGCCCAGCACCTGAACTCCTGGGGGGACTGTCAGTCTTCCTCTTC
241  H   T   C   P   P   C   P   A   P   E   L   L   G   G   P   S   V   F   L   F

781 CCCCCAAAACCCAAGGACACCCTCATGATCTCCCGGACCCCTGAGGTCACATGCGTGGTG
261  P   P   K   P   K   D   T   L   M   I   S   R   T   P   E   V   T   C   V   V

841 GTGGACGTGAGCCACGAAGACCCTGAGGTCAAGTTCAACTGGTACGTGGACGGCGTGGAG
281  V   D   V   S   H   E   D   P   E   V   K   F   N   W   Y   V   D   G   V   E

901 GTGCATAATGCCAAGACAAAGCCGCGGGAGGAGCAGTACAACAGCACGTACCGTGTGGTC
301  V   H   N   A   K   T   K   P   R   E   E   Q   Y   N   S   T   Y   R   V   V

961 AGCGTCCTCACCGTCCTGCACCAGGACTGGCTGAATGGCAAGGAGTACAAGTGCAAGGTC
321  S   V   L   T   V   L   H   Q   D   W   L   N   G   K   E   Y   K   C   K   V

1021 TCCAACAAAGCCCTCCCAGCCCCCATCGAGAAAACCATCTCCAAAGCCAAAGGGCAGCCC
341  S   N   K   A   L   P   A   P   I   E   K   T   I   S   K   A   K   G   Q   P

1081 CGAGAACCACAGGTGTACACCCTGCCCCCATCCCGGGAGGAGATGACCAAGAACCAGGTC
361  R   E   P   Q   V   Y   T   L   P   P   S   R   E   E   M   T   K   N   Q   V

1141 AGCCTGACCTGCCTGGTCAAAGGCTTCTATCCCAGCGACATCGCCGTGGAGTGGGAGAGC
381  S   L   T   C   L   V   K   G   F   Y   P   S   D   I   A   V   E   W   E   S

1201 AATGGGCAGCCGGAGAACAACTACAAGACCACGTCTCCCGTGCTGGACTCCGACGGCTCC
401  N   G   Q   P   E   N   N   Y   K   T   T   S   P   V   L   D   S   D   G   S

1261 TTCTTCCTCTATAGCAAGCTCACCGTGCACAAGAGCAGGTGGCAGCAGGGGAACGTCTTC
421  F   F   L   Y   S   K   L   T   V   D   K   S   R   W   Q   Q   G   N   V   F

1321 TCATGCTCCGTGATGCATGAGGCTCTGCACAACCACTACACGCAGAAGAGCCTCTCCCTG
441  S   C   S   V   M   H   E   A   L   H   N   H   Y   T   Q   K   S   L   S   L

1381 TCTCTGGGTAAATGA
461  S   L   G   K   *
```

10.7.2 The ORF of Y1-IgG-LC (SEQ ID NOS: 232 and 27 respectively)

```
   1 ATGGCCTGGGCTCTGCTGCTCCTCACCCTCCTCACTCAGGACACAGGGTCCTGGGCCGAT
   1  M   A   W   A   L   L   L   L   T   L   L   T   Q   D   T   G   S   W   A   D

61 GCAGAGCTGACTCAGGACCCTGCTGTGTCTGTGGCCTTGGGACAGACAGTCAGGATCACA
  21  A   E   L   T   Q   D   P   A   V   S   V   A   L   G   Q   T   V   R   I   T

1212 TGCCAAGGAGACAGCCTCAGAAGCTATTATGCAAGCTGGTACCAGCAGAAGCCAGGACAG
  41  C   Q   G   D   S   L   R   S   Y   Y   A   S   W   Y   Q   Q   K   P   G   Q

181 GCCCCTGTACTTGTCATCTATGGTAAAAACAACCGGCCCTCAGGGATCCCAGACCGATTC
 161  A   P   V   L   V   I   Y   G   K   N   N   R   P   S   G   I   P   D   R   F

241 TCTGGCTCCAGCTCAGGAAACACAGCTTCCTTGACCATCACTGGGGCTCAGGCGGAAGAT
  81  S   G   S   S   S   G   N   T   A   S   L   T   I   T   G   A   Q   A   E   D
```

```
                                    -continued
301   GAGGCTGACTATTACTGTAACTCCCGGGACAGCAGTGGTAACCATGTGGTATTCGGCGGA
101    E   A   D   Y   Y   C   N   S   R   D   S   S   G   N   H   V   V   F   G   G 361   GGGACCAAGCTGACCGTCCTAGGTCAGCCCAAGGCTGCCCCCTCGGTCACTCTGTTCCCG
121    G   T   K   L   T   V   L   G   Q   P   K   A   A   P   S   V   T   L   F   P 421   CCCTCCTCTGAGGAGCTTCAAGCCAACAAGGCCACACTGGTGTGTCTCATAAGTGACTTC
141    P   S   S   E   E   L   Q   A   N   K   A   T   L   V   C   L   I   S   D   F 481   TACCCGGGAGCCGTGACAGTGGCCTGGAAGGCAGATAGCAGCCCCGTCAAGGCGGGAGTG
161    Y   P   G   A   V   T   V   A   W   K   A   D   S   S   P   V   K   A   G   V 541   GAGACCACCACACCCTCCAAACAAAGCAACAACAAGTACGCGGCCAGCAGCTACCTGAGC
181    E   T   T   T   P   S   K   Q   S   N   N   K   Y   A   A   S   S   Y   L   S 601   CTGACGCCTGAGCAGTGGAAGTCCCACAAAAGCTACAGCTGCCAGGTCACGCATGAAGGG
201    L   T   P   E   Q   W   K   S   H   K   S   Y   S   C   Q   V   T   H   E   G 661   AGCACCGTGGAGAAGACAGTGGCCCCTACAGAATGTTCATGA
221    S   T   V   E   K   T   V   A   P   T   E   C   S   *
```

The leader sequence is underlined. The $V_H$ and $V_L$ regions are each encoded by amino acid sequences that are bolded, followed by either the IgG1 (for the heavy chain) or the λ3 (for the light chain) constant region sequences.

10.8 Expression of Y1 Heavy and Light Chain in CHO Cells. Vectors Y1-HC and Y1-LC were used individually for the transfection and selection of stable cells expressing the heavy or light chains. Following selection on G418 and cell growth, the secreted protein in the supernatant was analyzed for IgGI expression by the capture EIA assay and by Western blot analysis, as described below.

10.8.1 Capture EIA assay: The Wells of 96 well plates were pre-coated with mouse anti-human IgGI Fc (Sigma). The supernatant from above was added to the wells, and the presence of heavy chain IgGI was detected with biotinylated goat anti-γ chain specific antibody (Sigma), streptavidin-HRP and substrate. An ELISA plate reader monitored development of the color at $A_{405}$.

10.8.2 Western blot analysis: The supernatant for the above cells was run on 12.5% SDS-PAGE. Expression of each chain was detected with (a) goat anti-human IgG-HRP (H+L; Sigma Cat #A8667) for heavy chain detection and (b) biotinylated goat anti-human λ3 chain (Southern Biotechnology Association, Cat #2070-08) for light chain detection. Expression of both chains was confirmed by the above assays, and co-transfection was carried out to obtain full size Y1-IgG1.

10.9 Expression and Purification of Y1-IgG 10.9.1 Cell Culture and Transfection: CHO cells were cultivated in F-12 medium with 10% fetal calf serum and 40 μg/mi gentaMicin at 37° C. in 5% $CO_2$ atmosphere. One day before transfection $0.8 \times 10^6$ cells were seeded on 90 mm dishes. The cultures were co-transfected with 10 μg of light and heavy chains DNA by the FuGene (Roche) transfection reagent technique. After 2 days of growth in nonselective medium, the cells were cultured for 10–12 days in F-12 medium containing 550 μg/ml neomycin and 3 μg/ml puromycin. The cells were trypsinized and cloned by limiting dilution of 0.5 cell/well in Costar 96-well plates. Individual colonies were picked, grown in six-well dishes and transferred to flasks.

10.9.2 Determination of heavy and light chain secretion: A sandwich ELISA assay was used to determine the concentration of the antibody secreted into the supernatant of transfected CHO cells. In order to determine the concentration of the antibody, the following reagents were used: monoclonal anti human IgG1 (Fc) (Sigma) as the coated antibody, goat anti-human IgG (γ-chain specific) biotin conjugate as the detector (Sigma), and pure human IgG1, lambda (Sigma) as standard. Based on this ELISA assay the production rate varied between 3–4 μg/ml.

10.9.3 Production and Purification of MAb from the cells: Cells were grown in roller bottles to a final concentration of $1-2 \times 10^8$ cells per bottle in F-12 medium with 10% fetal calf serum, supplemented with neomycin and puromycin. For the production, cells were cultured in the same medium, but with 2% of fetal calf serum for an additional two days. The secreted antibody was purified on a protein G-Sepharose column (Pharmacia). Binding was in 20 mM sodium phosphate buffer, pH 7.0; elution was performed in 0.1M glycine buffer, pH 2.5–3.0. The quantity of the purified antibody was determined by UV absorbance; purity was analyzed by SDS-PAGE. Under non-denaturing conditions the full IgG antibody has its expected molecular weight of 160 kD. In denaturing gels both heavy and light chains have the expected molecular size of 55 and 28 kD, respectively.

10.9.4 Binding of full size Y1-IgG molecule: Binding experiments were performed to determine the level of binding of the Y1-IgG molecule compared to the binding level of the scFv-Y1 molecule. A two-step staining procedure was employed, wherein 5 ng of Y1-IgG were reacted with both RAJI cells (negative control, FIG. 7a) and Jurkat cells (Y1 positive cells, FIG. 7b). For detection, PE-labeled goat anti-human IgG was used. Similarly, 1 μg of scFv-Y1 was reacted with Jurkat cells (FIG. 7c), and PE-labeled rabbit anti-scFv was used for detection. Results indicate that both Y1-IgG and scFv-Y1 bind to the Jurkat cells, with approximately $10^3$-fold more scFv-Y1 molecules needed to obtain a level of detection similar to that of the Y1-IgG.

BRIEF DESCRIPTION OF THE TABLES

Table 1: Panning results derived from protocol AM. The estimated number of phagemids used for panning (input), and the estimated number of bound phagemids eluted (output) are summarized for the four consecutive steps of the AM biopanning protocol. The cell source and elution medium for each output result is listed, as well as the term used to distinguish each separate stock.

Table 2: Selected clones following the AM biopanning protocol. The number of amino acid residues in the CDR3 region ($V_H$-CDR3 size) and the CDR3 amino acid sequences for the different clone types isolated are summarized. In addition, the frequency of each of the clone types in the two AM biopanning outputs, the T16M3 and T16M3.1 outputs, are presented.

Table 3: Panning results derived from the YPR protocol. The estimated number of phagemids used for panning (input), and the estimated number of bound phagemids eluted (output) are summarized. The elution medium for each output result is listed, as well as the term used to distinguish each separate stock.

Table 4: Panning results derived from the YPNR protocol. The estimated number of phagemids used for panning (input), and the estimated number of bound phagemids eluted (output) are summarized for the three consecutive steps of the YPNR biopanning protocol. The elution medium for each output result is listed, as well as the term used to distinguish each separate stock.

Table 5: Selected Y-series clones following the YPR biopanning protocol with the R3 output. Several different clones were identified in the R3 output stock. The number of amino acid residues comprising, and the amino acid sequences of, the $V_H$-CDR3 regions of the identified clones, as well as germline designations, are detailed.

Table 6: Y1 Binding specificity for leukemia cells. The results of binding experiments of three different scFv clones, each reacted with mixtures of cells containing primarily each of seven different leukemic cell types, as determined by FACS analysis, are presented. The results represent the fraction of patients, the cells of whom were identified by FACS analysis as positively reacting with each tested antibody. The numerator represents the number of positive patients, with the denominator denoting the total number of patients tested for a given scFv/leukemic cell type combination Table 7: FACS analysis of scFv binding to Ficoll-purified normal blood cells. Three scFv clones are each analyzed for binding to five different Ficoll-purified normal blood cell types. These binding results represent the fraction of normal blood samples that were identified by FACS analysis as positively reacting with each tested antibody.

Table 8: Comparison of Y1 scFv binding with binding of antibodies to various cell markers. Results of FACS analysis of staining by Y1 and by a panel of other antibodies are presented. Ficoll-purified peripheral and bone marrow cells from ANE patients were prepared and the binding specificity of Y1 scFv compared to various cell markers on AML cells was studied. The results are expressed as the percentage of cells in the Ficoll-purified samples of a given patient, which was identified by FACS analysis as positively reacting with each Fv. Four other antibodies were run for comparison: (1) CD13—a marker for granulocytes and monocytes; (2) CD14—a marker for monocytes and neutrophils; (3) CD33—a marker for normal myeloid cells and leukemic myeloid cells; and (4) CD34—a marker for stem cells.

Table 9: Binding of Y1 to hematopoietic cell lines. FACS analysis was performed to determine the binding of Y1 scFv to three different categories of human leukemia cell lines, and to one murine cell line. Cell lines to which Y1 was positively bound (reactive) or not (non-reactive) are listed.

Table 10: The CDR3 sequence of $V_H$3-DP32 isolated clones. Following different biopanning and selection procedures several clones based on the DP32 germline were isolated. Clones Y1, Y17, Y-27 and Y-44 were identified during the biopanning selection on platelets (YPR and YPNR protocols). The sequence of the $V_H$-CDR3 region of each of these clones is presented.

Table 11: Binding profile of $V_H$3-DP32 isolated clones. The binding specificity of DP32-derived clones to several hematopoietic cells was tested by FACS analysis.

The invention has been described with reference to specific examples, materials and data. As one skilled in the art will appreciate, alternate means for using or preparing the various aspects of the invention may be available. Such alternate means are to be construed as included within the intent and spirit of the present invention as defined by the following claims.

SEQUENCE LISTING

```
<160> NUMBER OF SEQ ID NOS: 203

<210> SEQ ID NO 1
<211> LENGTH: 10
<212> TYPE: PRT
<213> ORGANISM: Homo sapiens

<400> SEQUENCE: 1

Ser Ser Tyr Thr Ser Ser Ser Thr Leu Val
1               5                   10

<210> SEQ ID NO 2
<211> LENGTH: 10
<212> TYPE: PRT
<213> ORGANISM: Homo sapiens

<400> SEQUENCE: 2

Ser Ser Tyr Thr Ser Ser Ser Thr Leu Gly
1               5                   10

<210> SEQ ID NO 3
<211> LENGTH: 9
```

```
<212> TYPE: PRT
<213> ORGANISM: Homo sapiens

<400> SEQUENCE: 3

Gln Ser Tyr Asp Ser Asn Leu Arg Val
1               5

<210> SEQ ID NO 4
<211> LENGTH: 8
<212> TYPE: PRT
<213> ORGANISM: Homo sapiens

<400> SEQUENCE: 4

Gln Gln Leu Asn Ser Tyr Pro Thr
1               5

<210> SEQ ID NO 5
<211> LENGTH: 11
<212> TYPE: PRT
<213> ORGANISM: Homo sapiens

<400> SEQUENCE: 5

Asn Ser Arg Asp Ser Ser Gly Phe Gln Leu Val
1               5                   10

<210> SEQ ID NO 6
<211> LENGTH: 9
<212> TYPE: PRT
<213> ORGANISM: Homo sapiens

<400> SEQUENCE: 6

Gln Gln Ala Asn Ser Phe Pro Ile Thr
1               5

<210> SEQ ID NO 7
<211> LENGTH: 111
<212> TYPE: PRT
<213> ORGANISM: Homo sapiens

<400> SEQUENCE: 7

Ser Glu Leu Thr Gln Asp Pro Ala Val Ser Val Ala Leu Gly Gln Thr
1               5                   10                  15

Val Arg Ile Thr Cys Gln Gly Asp Ser Leu Arg Ser Tyr Tyr Ala Ser
            20                  25                  30

Trp Tyr Gln Gln Lys Pro Gly Gln Ala Pro Val Leu Val Ile Tyr Gly
        35                  40                  45

Lys Asn Asn Arg Pro Ser Gly Ile Pro Asp Arg Phe Ser Gly Ser Ser
    50                  55                  60

Ser Gly Asn Thr Ala Ser Leu Thr Ile Thr Gly Ala Gln Ala Glu Asp
65                  70                  75                  80

Glu Ala Asp Tyr Tyr Cys Asn Ser Arg Asp Ser Ser Gly Asn His Val
                85                  90                  95

Val Phe Gly Gly Gly Thr Lys Leu Thr Val Leu Gly Ala Ala Ala
            100                 105                 110

<210> SEQ ID NO 8
<211> LENGTH: 6
<212> TYPE: PRT
<213> ORGANISM: Homo sapiens

<400> SEQUENCE: 8

Met Arg Ala Pro Val Ile
```

```
1               5

<210> SEQ ID NO 9
<211> LENGTH: 8
<212> TYPE: PRT
<213> ORGANISM: Homo sapiens

<400> SEQUENCE: 9

Pro Trp Asp Asp Val Thr Pro Pro
1               5

<210> SEQ ID NO 10
<211> LENGTH: 12
<212> TYPE: PRT
<213> ORGANISM: Homo sapiens

<400> SEQUENCE: 10

Gly Phe Pro Arg Ile Thr Pro Pro Ser Ala Glu Ile
1               5                   10

<210> SEQ ID NO 11
<211> LENGTH: 5
<212> TYPE: PRT
<213> ORGANISM: Homo sapiens

<400> SEQUENCE: 11

Gly Phe Pro Met Pro
1               5

<210> SEQ ID NO 12
<211> LENGTH: 10
<212> TYPE: PRT
<213> ORGANISM: Homo sapiens

<400> SEQUENCE: 12

Gly Phe Pro His Ser Ser Ser Val Ser Arg
1               5                   10

<210> SEQ ID NO 13
<211> LENGTH: 11
<212> TYPE: PRT
<213> ORGANISM: Homo sapiens

<400> SEQUENCE: 13

Arg Phe Pro Met Arg His Glu Lys Thr Asn Tyr
1               5                   10

<210> SEQ ID NO 14
<211> LENGTH: 8
<212> TYPE: PRT
<213> ORGANISM: Homo sapiens

<400> SEQUENCE: 14

Arg Phe Pro Pro Thr Ala Thr Ile
1               5

<210> SEQ ID NO 15
<211> LENGTH: 7
<212> TYPE: PRT
<213> ORGANISM: Homo sapiens

<400> SEQUENCE: 15

Thr Gln Arg Arg Asp Leu Gly
1               5
```

```
<210> SEQ ID NO 16
<211> LENGTH: 11
<212> TYPE: PRT
<213> ORGANISM: Homo sapiens

<400> SEQUENCE: 16

Lys Phe Pro Gly Gly Thr Val Arg Gly Leu Lys
1               5                   10

<210> SEQ ID NO 17
<211> LENGTH: 12
<212> TYPE: PRT
<213> ORGANISM: Homo sapiens

<400> SEQUENCE: 17

Gly Phe Pro Val Ile Val Glu Glu Arg Gln Ser Thr
1               5                   10

<210> SEQ ID NO 18
<211> LENGTH: 10
<212> TYPE: PRT
<213> ORGANISM: Homo sapiens

<400> SEQUENCE: 18

Arg Phe Pro Gln Arg Val Asp Asn Arg Val
1               5                   10

<210> SEQ ID NO 19
<211> LENGTH: 8
<212> TYPE: PRT
<213> ORGANISM: Homo sapiens

<400> SEQUENCE: 19

Thr Gly Gln Ser Ile Lys Arg Ser
1               5

<210> SEQ ID NO 20
<211> LENGTH: 6
<212> TYPE: PRT
<213> ORGANISM: Homo sapiens

<400> SEQUENCE: 20

Leu Thr His Pro Tyr Phe
1               5

<210> SEQ ID NO 21
<211> LENGTH: 6
<212> TYPE: PRT
<213> ORGANISM: Homo sapiens

<400> SEQUENCE: 21

Leu Arg Pro Pro Gln Ser
1               5

<210> SEQ ID NO 22
<211> LENGTH: 11
<212> TYPE: PRT
<213> ORGANISM: Homo sapiens

<400> SEQUENCE: 22

Thr Ser Lys Asn Thr Ser Ser Lys Arg His
1               5                   10

<210> SEQ ID NO 23
```

```
<211> LENGTH: 12
<212> TYPE: PRT
<213> ORGANISM: Homo sapiens

<400> SEQUENCE: 23

Arg Tyr Tyr Cys Arg Ser Ser Asp Cys Thr Val Ser
1               5                   10

<210> SEQ ID NO 24
<211> LENGTH: 10
<212> TYPE: PRT
<213> ORGANISM: Homo sapiens

<400> SEQUENCE: 24

Phe Arg Arg Met Glu Thr Val Pro Ala Pro
1               5                   10

<210> SEQ ID NO 25
<211> LENGTH: 277
<212> TYPE: PRT
<213> ORGANISM: Homo sapiens

<400> SEQUENCE: 25

Met Lys Tyr Leu Leu Pro Thr Ala Ala Ala Gly Leu Leu Leu Leu Ala
1               5                   10                  15

Ala Gln Pro Ala Met Ala Glu Val Gln Leu Val Glu Ser Gly Gly Gly
            20                  25                  30

Val Val Arg Pro Gly Gly Ser Leu Arg Leu Ser Cys Ala Ala Ser Gly
        35                  40                  45

Phe Thr Phe Asp Asp Tyr Gly Met Ser Trp Val Arg Gln Ala Pro Gly
    50                  55                  60

Lys Gly Leu Glu Trp Val Ser Gly Ile Asn Trp Asn Gly Gly Ser Thr
65                  70                  75                  80

Gly Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Met Arg Ala Pro Val Ile Trp Gly
        115                 120                 125

Gln Gly Thr Leu Val Thr Val Ser Arg Gly Gly Gly Ser Gly Gly
    130                 135                 140

Gly Gly Ser Gly Gly Gly Ser Ser Glu Leu Thr Gln Asp Pro Ala
145                 150                 155                 160

Val Ser Val Ala Leu Gly Gln Thr Val Arg Ile Thr Cys Gln Gly Asp
                165                 170                 175

Ser Leu Arg Ser Tyr Tyr Ala Ser Trp Tyr Gln Gln Lys Pro Gly Gln
            180                 185                 190

Ala Pro Val Leu Val Ile Tyr Gly Lys Asn Asn Arg Pro Ser Gly Ile
        195                 200                 205

Pro Asp Arg Phe Ser Gly Ser Ser Ser Gly Asn Thr Ala Ser Leu Thr
    210                 215                 220

Ile Thr Gly Ala Gln Ala Glu Asp Glu Ala Asp Tyr Tyr Cys Asn Ser
225                 230                 235                 240

Arg Asp Ser Ser Gly Asn His Val Val Phe Gly Gly Gly Thr Lys Leu
                245                 250                 255

Thr Val Leu Gly Ala Ala Ala Glu Gln Lys Leu Ile Ser Glu Glu Asp
            260                 265                 270
```

-continued

Leu Asn Gly Ala Ala
        275

<210> SEQ ID NO 26
<211> LENGTH: 464
<212> TYPE: PRT
<213> ORGANISM: Homo sapiens

<400> SEQUENCE: 26

Met Ala Trp Ala Leu Leu Leu Thr Leu Thr Gln Asp Thr Gly
1               5                   10                  15

Ser Trp Ala Asp Ile Gln Leu Val Glu Ser Gly Gly Val Val Arg
        20                  25                  30

Pro Gly Gly Ser Leu Arg Leu Ser Cys Ala Ala Ser Gly Phe Thr Phe
            35                  40                  45

Asp Asp Tyr Gly Met Ser Trp Val Arg Gln Ala Pro Gly Lys Gly Leu
    50                  55                  60

Glu Trp Val Ser Gly Ile Asn Trp Asn Gly Ser Thr Gly Tyr Ala
65                  70                  75                  80

Asp Ser Val Lys Gly Arg Phe Thr Ile Ser Arg Asp Asn Ala Lys Asn
                85                  90                  95

Ser Leu Tyr Leu Gln Met Asn Ser Leu Arg Ala Glu Asp Thr Ala Val
            100                 105                 110

Tyr Tyr Cys Ala Arg Met Arg Ala Pro Val Ile Trp Gly Gln Gly Thr
        115                 120                 125

Leu Val Thr Val Ser Ser Ala Ser Thr Lys Gly Pro Ser Val Phe Pro
    130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
                165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
        195                 200                 205

Ser Leu Gly Thr Gln Thr Tyr Ile Cys Asn Val Asn His Lys Pro Ser
    210                 215                 220

Asn Thr Lys Val Asp Lys Arg Val Glu Pro Lys Ser Cys Asp Lys Thr
225                 230                 235                 240

His Thr Cys Pro Pro Cys Pro Ala Pro Glu Leu Leu Gly Gly Pro Ser
                245                 250                 255

Val Phe Leu Phe Pro Pro Lys Pro Lys Asp Thr Leu Met Ile Ser Arg
            260                 265                 270

Thr Pro Glu Val Thr Cys Val Val Val Asp Val Ser His Glu Asp Pro
    275                 280                 285

Glu Val Lys Phe Asn Trp Tyr Val Asp Gly Val Glu Val His Asn Ala
290                 295                 300

Lys Thr Lys Pro Arg Glu Glu Gln Tyr Asn Ser Thr Tyr Arg Val Val
305                 310                 315                 320

Ser Val Leu Thr Val Leu His Gln Asp Trp Leu Asn Gly Lys Glu Tyr
                325                 330                 335

Lys Cys Lys Val Ser Asn Lys Ala Leu Pro Ala Pro Ile Glu Lys Thr
            340                 345                 350

Ile Ser Lys Ala Lys Gly Gln Pro Arg Glu Pro Gln Val Tyr Thr Leu
        355                 360                 365

-continued

```
Pro Pro Ser Arg Glu Glu Met Thr Lys Asn Gln Val Ser Leu Thr Cys
        370                 375                 380

Leu Val Lys Gly Phe Tyr Pro Ser Asp Ile Ala Val Glu Trp Glu Ser
385                 390                 395                 400

Asn Gly Gln Pro Glu Asn Asn Tyr Lys Thr Thr Pro Val Leu Asp
                405                 410                 415

Ser Asp Gly Ser Phe Phe Leu Tyr Ser Lys Leu Thr Val Asp Lys Ser
                420                 425                 430

Arg Trp Gln Gln Gly Asn Val Phe Ser Cys Ser Val Met His Glu Ala
                435                 440                 445

Leu His Asn His Tyr Thr Gln Lys Ser Leu Ser Leu Ser Leu Gly Lys
        450                 455                 460

<210> SEQ ID NO 27
<211> LENGTH: 233
<212> TYPE: PRT
<213> ORGANISM: Homo sapiens

<400> SEQUENCE: 27

Met Ala Trp Ala Leu Leu Leu Thr Leu Leu Thr Gln Asp Thr Gly
1               5                   10                  15

Ser Trp Ala Asp Ala Glu Leu Thr Gln Asp Pro Ala Val Ser Val Ala
                20                  25                  30

Leu Gly Gln Thr Val Arg Ile Thr Cys Gln Gly Asp Ser Leu Arg Ser
            35                  40                  45

Tyr Tyr Ala Ser Trp Tyr Gln Gln Lys Pro Gly Gln Ala Pro Val Leu
    50                  55                  60

Val Ile Tyr Gly Lys Asn Asn Arg Pro Ser Gly Ile Pro Asp Arg Phe
65                  70                  75                  80

Ser Gly Ser Ser Ser Gly Asn Thr Ala Ser Leu Thr Ile Thr Gly Ala
                85                  90                  95

Gln Ala Glu Asp Glu Ala Asp Tyr Tyr Cys Asn Ser Arg Asp Ser Ser
                100                 105                 110

Gly Asn His Val Val Phe Gly Gly Gly Thr Lys Leu Thr Val Leu Gly
            115                 120                 125

Gln Pro Lys Ala Ala Pro Ser Val Thr Leu Phe Pro Pro Ser Ser Glu
130                 135                 140

Glu Leu Gln Ala Asn Lys Ala Thr Leu Val Cys Leu Ile Ser Asp Phe
145                 150                 155                 160

Tyr Pro Gly Ala Val Thr Val Ala Trp Lys Ala Asp Ser Ser Pro Val
                165                 170                 175

Lys Ala Gly Val Glu Thr Thr Thr Pro Ser Lys Gln Ser Asn Asn Lys
            180                 185                 190

Tyr Ala Ala Ser Ser Tyr Leu Ser Leu Thr Pro Glu Gln Trp Lys Ser
        195                 200                 205

His Lys Ser Tyr Ser Cys Gln Val Thr His Glu Gly Ser Thr Val Glu
210                 215                 220

Lys Thr Val Ala Pro Thr Glu Cys Ser
225                 230

<210> SEQ ID NO 28
<211> LENGTH: 11
<212> TYPE: PRT
<213> ORGANISM: Homo sapiens

<400> SEQUENCE: 28
```

```
Phe Leu Thr Tyr Asn Ser Tyr Glu Val Pro Thr
1               5                   10
```

<210> SEQ ID NO 29
<211> LENGTH: 9
<212> TYPE: PRT
<213> ORGANISM: Homo sapiens

<400> SEQUENCE: 29

```
Thr Asn Trp Tyr Leu Arg Pro Leu Asn
1               5
```

<210> SEQ ID NO 30
<211> LENGTH: 98
<212> TYPE: PRT
<213> ORGANISM: Homo sapiens

<400> SEQUENCE: 30

```
Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asp Tyr
            20                  25                  30

Tyr Met His Trp Val Gln Gln Ala Pro Gly Lys Gly Leu Glu Trp Met
        35                  40                  45

Gly Leu Val Asp Pro Glu Asp Gly Glu Thr Ile Tyr Ala Glu Lys Phe
    50                  55                  60

Gln Gly Arg Val Thr Ile Thr Ala Asp Thr Ser Thr Asp Thr Ala Tyr
65                  70                  75                  80

Met Glu Leu Ser Ser Leu Arg Ser Glu Asp Thr Ala Val Tyr Tyr Cys
                85                  90                  95

Ala Thr
```

<210> SEQ ID NO 31
<211> LENGTH: 98
<212> TYPE: PRT
<213> ORGANISM: Homo sapiens

<400> SEQUENCE: 31

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ile Phe Thr Asp Tyr
            20                  25                  30

Tyr Met His Trp Val Arg Gln Ala Pro Gly Gln Glu Leu Gly Trp Met
        35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Thr Glu Leu Ser Ser Leu Arg Ser Glu Asp Thr Ala Thr Tyr Tyr Cys
                85                  90                  95

Ala Arg
```

<210> SEQ ID NO 32
<211> LENGTH: 98
<212> TYPE: PRT
<213> ORGANISM: Homo sapiens

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Val Ser Gly Tyr Thr Leu Thr Glu Leu
            20                  25                  30

Ser Met His Trp Val Arg Gln Ala Pro Gly Lys Gly Leu Glu Trp Met
        35                  40                  45

Gly Gly Phe Asp Pro Glu Asp Gly Glu Thr Ile Tyr Ala Gln Lys Phe
    50                  55                  60

Gln Gly Arg Val Thr Met Thr Glu Asp Thr Ser Thr Asp Thr Ala Tyr
65                  70                  75                  80

Met Glu Leu Ser Ser Leu Arg Ser Glu Asp Thr Ala Val Tyr Tyr Cys
            85                  90                  95

Ala Thr

<210> SEQ ID NO 33
<211> LENGTH: 98
<212> TYPE: PRT
<213> ORGANISM: Homo sapiens

<400> SEQUENCE: 33

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Arg Ile Asn Pro Asn Ser Gly Gly Thr Asn Tyr Ala Gln Lys Phe
    50                  55                  60

Gln Gly Arg Val Thr Ser Thr Arg Asp Thr Ser Ile Ser Thr Ala Tyr
65                  70                  75                  80

Met Glu Leu Ser Arg Leu Arg Ser Asp Asp Thr Val Val Tyr Tyr Cys
            85                  90                  95

Ala Arg

<210> SEQ ID NO 34
<211> LENGTH: 98
<212> TYPE: PRT
<213> ORGANISM: Homo sapiens

<400> SEQUENCE: 34

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
        35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
            85                  90                  95

Ala Arg

<210> SEQ ID NO 35
<211> LENGTH: 98

-continued

<212> TYPE: PRT
<213> ORGANISM: Homo sapiens

<400> SEQUENCE: 35

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
                20                  25                  30

Tyr Met His Trp Val Arg Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Trp Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 36
<211> LENGTH: 98
<212> TYPE: PRT
<213> ORGANISM: Homo sapiens
<220> FEATURE:
<221> NAME/KEY: X
<222> LOCATION: (1)..(98)
<223> OTHER INFORMATION: Xaa

<400> SEQUENCE: 36

Gln Val Gln Leu Val Gln Ser Gly Ala Glu Val Lys Lys Leu Gly Ala
1               5                   10                  15

Ser Val Lys Val Ser Cys Lys Ala Ser Gly Tyr Thr Phe Thr Gly Tyr
                20                  25                  30

Tyr Met His Trp Val Xaa Gln Ala Pro Gly Gln Gly Leu Glu Trp Met
            35                  40                  45

Gly Trp Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg

<210> SEQ ID NO 37
<211> LENGTH: 98
<212> TYPE: PRT
<213> ORGANISM: Homo sapiens

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Cys Met His Trp Val Arg Gln Val His Ala Gln Gly Leu Glu Trp Met
            35                  40                  45

Gly Leu Val Cys Pro Ser Asp Gly Ser Thr Ser Tyr Ala Gln Lys Phe
    50                  55                  60

Gln Ala Arg Val Thr Ile Thr Arg Asp Thr Ser Met Ser Thr Ala Tyr
65                  70                  75                  80

Met Glu Leu Ser Ser Leu Arg Ser Glu Asp Thr Ala Met Tyr Tyr Cys
                85                  90                  95

Val Arg

<210> SEQ ID NO 38
<211> LENGTH: 98
<212> TYPE: PRT
<213> ORGANISM: Homo sapiens

<400> SEQUENCE: 38

Gln Met Gln Leu Val Gln Ser Gly Pro Glu Val Lys Lys Pro Gly Thr
1               5                   10                  15

Ser Val Lys Val Ser Cys Lys Ala Ser Gly Phe Thr Phe Thr Ser Ser
            20                  25                  30

Ala Val Gln Trp Val Arg Gln Ala Arg Gly Gln Arg Leu Glu Trp Ile
        35                  40                  45

Gly Trp Ile Val Val Gly Ser Gly Asn Thr Asn Tyr Ala Gln Lys Phe
    50                  55                  60

Gln Glu Arg Val Thr Ile Thr Arg Asp Met Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Ala

<210> SEQ ID NO 39
<211> LENGTH: 98
<212> TYPE: PRT
<213> ORGANISM: Homo sapiens

<400> SEQUENCE: 39

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 40
<211> LENGTH: 98
<212> TYPE: PRT
<213> ORGANISM: Homo sapiens

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

```
Gly Arg Ile Ile Pro Ile Leu Gly Ile Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 41
<211> LENGTH: 98
<212> TYPE: PRT
<213> ORGANISM: Homo sapiens

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ile Asn Ala Gly Asn Gly Asn Thr Lys Tyr Ser Gln Lys Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 42
<211> LENGTH: 98
<212> TYPE: PRT
<213> ORGANISM: Homo sapiens

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Ala Met His Trp Val Arg Gln Ala Pro Gly Gln Arg Leu Glu Trp Met
            35                  40                  45

Gly Trp Ser Asn Ala Gly Asn Gly Asn Thr Lys Tyr Ser Gln Glu Phe
    50                  55                  60

Gln Gly Arg Val Thr Ile Thr Arg Asp Thr Ser Ala Ser Thr Ala Tyr
65                  70                  75                  80

Met Glu Leu Ser Ser Leu Arg Ser Glu Asp Met Ala Val Tyr Tyr Cys
                85                  90                  95
Ala Arg

<210> SEQ ID NO 43
<211> LENGTH: 98
<212> TYPE: PRT
<213> ORGANISM: Homo sapiens

<400> SEQUENCE: 43

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Ser Tyr
                20                  25                  30
```

```
Ala Met Asn Trp Val Arg Gln Ala Pro Gly Gln Gly Leu Glu Trp Met
        35                  40                  45

Gly Trp Ile Asn Thr Asn Thr Gly Asn Pro Thr Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Cys Ser Leu Lys Ala Glu Asp Thr Ala Val Tyr Tyr Cys
                 85                  90                  95

Ala Arg

<210> SEQ ID NO 44
<211> LENGTH: 98
<212> TYPE: PRT
<213> ORGANISM: Homo sapiens

<400> SEQUENCE: 44

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Ser Tyr
                 20                  25                  30

Ala Met Asn Trp Val Arg Gln Ala Pro Gly Gln Gly Leu Glu Trp Met
            35                  40                  45

Gly Trp Ile Asn Thr Asn Thr Gly Asn Pro Thr Tyr Ala Gln Gly Phe
 50                  55                  60

Thr Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg

<210> SEQ ID NO 45
<211> LENGTH: 98
<212> TYPE: PRT
<213> ORGANISM: Homo sapiens

<400> SEQUENCE: 45

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Asp Ile Asn Trp Val Arg Gln Ala Thr Gly Gln Gly Leu Glu Trp Met
            35                  40                  45

Gly Trp Met Asn Pro Asn Ser Gly Asn Thr Gly Tyr Ala Gln Lys Phe
 50                  55                  60

Gln Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg

<210> SEQ ID NO 46
<211> LENGTH: 98
<212> TYPE: PRT
<213> ORGANISM: Homo sapiens

<400> SEQUENCE: 46
```

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
50                      55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg

<210> SEQ ID NO 47
<211> LENGTH: 92
<212> TYPE: PRT
<213> ORGANISM: Homo sapiens

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala
                85                  90

<210> SEQ ID NO 48
<211> LENGTH: 98
<212> TYPE: PRT
<213> ORGANISM: Homo sapiens

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 49
<211> LENGTH: 98
<212> TYPE: PRT
<213> ORGANISM: Homo sapiens
```

<400> SEQUENCE: 49

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Asn Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg

<210> SEQ ID NO 50
<211> LENGTH: 98
<212> TYPE: PRT
<213> ORGANISM: Homo sapiens

<400> SEQUENCE: 50

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
            20                  25                  30

Tyr Leu His Trp Val Arg Gln Ala Pro Gly Gln Ala Leu Glu Trp Met
        35                  40                  45

Gly Trp Ile Thr Pro Phe Asn Gly Asn Thr Asn Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg

<210> SEQ ID NO 51
<211> LENGTH: 98
<212> TYPE: PRT
<213> ORGANISM: Homo sapiens

<400> SEQUENCE: 51

Gln Met Gln Leu Val Gln Ser Gly Ala Glu Val Lys Lys Thr Gly Ser
1               5                   10                  15

Ser Val Lys Val Ser Cys Lys Ala Ser Gly Tyr Thr Phe Thr Tyr Arg
            20                  25                  30

Tyr Leu His Trp Val Arg Gln Ala Pro Gly Gln Ala Leu Glu Trp Met
        35                  40                  45

Gly Trp Ile Thr Pro Phe Asn Gly Asn Thr Asn Tyr Ala Gln Lys Phe
    50                  55                  60

Gln Asp Arg Val Thr Ile Thr Arg Asp Arg Ser Met Ser Thr Ala Tyr
65                  70                  75                  80

Met Glu Leu Ser Ser Leu Arg Ser Glu Asp Thr Ala Met Tyr Tyr Cys
                85                  90                  95

Ala Arg

```
<210> SEQ ID NO 52
<211> LENGTH: 96
<212> TYPE: PRT
<213> ORGANISM: Homo sapiens

<400> SEQUENCE: 52

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

<210> SEQ ID NO 53
<211> LENGTH: 99
<212> TYPE: PRT
<213> ORGANISM: Homo sapiens

<400> SEQUENCE: 53

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Glu Trp Cys Gly Trp Ile Arg Gln Pro Pro Gly Lys Ala Leu Glu Trp
        35                  40                  45

Leu Ala Leu Ile Tyr Trp Asn Asp Asp Lys Arg Tyr Ser Pro Ser Leu
    50                  55                  60

Lys Ser Arg Leu Thr Ile Thr Lys Asp Thr Ser Lys Asn Gln Val Val
65                  70                  75                  80

Leu Thr Met Thr Asn Met Asp Pro Val Asp Thr Ala Thr Tyr Tyr Cys
                85                  90                  95

Ala His Arg

<210> SEQ ID NO 54
<211> LENGTH: 96
<212> TYPE: PRT
<213> ORGANISM: Homo sapiens

<400> SEQUENCE: 54

Gln Val Thr Leu Arg Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Cys Val Ser Trp Ile Arg Gln Pro Pro Gly Lys Ala Leu Glu
        35                  40                  45

Trp Leu Ala Leu Ile Asp Trp Asp Asp Lys Tyr Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95
```

<210> SEQ ID NO 55
<211> LENGTH: 96
<212> TYPE: PRT
<213> ORGANISM: Homo sapiens

<400> SEQUENCE: 55

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Met Arg Val Ser Trp Ile Arg Gln Pro Pro Gly Lys Ala Leu Glu
        35                  40                  45

Trp Leu Ala Arg Ile Asp Trp Asp Asp Lys Phe Tyr Ser Thr Ser
    50                  55                  60

Leu Lys Thr Arg Leu Thr Ile Ser Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95
```

<210> SEQ ID NO 56
<211> LENGTH: 100
<212> TYPE: PRT
<213> ORGANISM: Homo sapiens

<400> SEQUENCE: 56

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Ser
            20                  25                  30

Gly Val Gly Val Gly Trp Ile Arg Gln Pro Pro Gly Lys Ala Leu Glu
        35                  40                  45

Trp Leu Ala Leu Ile Tyr Trp Asn Asp Asp Lys Arg Tyr Ser Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Arg
            100
```

<210> SEQ ID NO 57
<211> LENGTH: 100
<212> TYPE: PRT
<213> ORGANISM: Homo sapiens

<400> SEQUENCE: 57

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Asp Trp Val Arg Gln Ala Pro Gly Lys Gly Leu Glu Trp Val
        35                  40                  45

Gly Arg Thr Arg Asn Lys Ala Asn Ser Tyr Thr Thr Glu Tyr Ala Ala
    50                  55                  60

Ser Val Lys Gly Arg Phe Thr Ile Ser Arg Asp Asp Ser Lys Asn Ser
65                  70                  75                  80
```

```
Leu Tyr Leu Gln Met Asn Ser Leu Lys Thr Glu Asp Thr Ala Val Tyr
                85                  90                  95

Tyr Cys Ala Arg
            100

<210> SEQ ID NO 58
<211> LENGTH: 100
<212> TYPE: PRT
<213> ORGANISM: Homo sapiens

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Ser Trp Val Arg Gln Ala Gln Gly Lys Gly Leu Glu Leu Val
        35                  40                  45

Gly Leu Ile Arg Asn Lys Ala Asn Ser Tyr Thr Thr Glu Tyr Ala Ala
    50                  55                  60

Ser Val Lys Gly Arg Leu Thr Ile Ser Arg Glu Asp Ser Lys Asn Thr
65                  70                  75                  80

Leu Tyr Leu Gln Met Ser Ser Leu Lys Thr Glu Asp Leu Ala Val Tyr
                85                  90                  95

Tyr Cys Ala Arg
            100

<210> SEQ ID NO 59
<211> LENGTH: 100
<212> TYPE: PRT
<213> ORGANISM: Homo sapiens

<400> SEQUENCE: 59

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp His
            20                  25                  30

Tyr Met Ser Trp Val Arg Gln Ala Gln Gly Lys Gly Leu Glu Leu Val
        35                  40                  45

Gly Leu Ile Arg Asn Lys Ala Asn Ser Tyr Thr Thr Glu Tyr Ala Ala
    50                  55                  60

Ser Val Lys Gly Arg Leu Thr Ile Ser Arg Glu Asp Ser Lys Asn Thr
65                  70                  75                  80

Leu Tyr Leu Gln Met Ser Ser Leu Lys Thr Glu Asp Leu Ala Val Tyr
                85                  90                  95

Tyr Cys Ala Arg
            100

<210> SEQ ID NO 60
<211> LENGTH: 98
<212> TYPE: PRT
<213> ORGANISM: Homo sapiens

<400> SEQUENCE: 60

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
```

```
                35                  40                  45
Ser Gly Ile Ser Trp Asn Ser Gly Ser Ile Gly Tyr Ala Asp Ser Val
        50                  55                  60
Lys Gly Arg Phe Thr Ile Ser Arg Asp Asn Ala Lys Asn Ser Leu Tyr
 65                  70                  75                  80
Leu Gln Met Asn Ser Leu Arg Ala Glu Asp Thr Ala Leu Tyr Tyr Cys
                85                  90                  95
Ala Lys

<210> SEQ ID NO 61
<211> LENGTH: 98
<212> TYPE: PRT
<213> ORGANISM: Homo sapiens

<400> SEQUENCE: 61

Glu Val Gln Leu Val Glu Ser Gly Gly Val Val Arg Pro Gly Gly
 1               5                  10                  15

Ser Leu Arg Leu Ser Cys Ala Ala Ser Gly Phe Thr Phe Asp Asp Tyr
                20                  25                  30

Gly Met Ser Trp Val Arg Gln Ala Pro Gly Lys Gly Leu Glu Trp Val
                35                  40                  45

Ser Gly Ile Asn Trp Asn Gly Gly Ser Thr Gly Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr His Cys
                85                  90                  95

Ala Arg

<210> SEQ ID NO 62
<211> LENGTH: 98
<212> TYPE: PRT
<213> ORGANISM: Homo sapiens

<400> SEQUENCE: 62

Glu Val Gln Leu Val Glu Ser Gly Gly Val Val Gln Pro Gly Gly
 1               5                  10                  15

Ser Leu Arg Leu Ser Cys Ala Ala Ser Gly Phe Thr Phe Asp Asp Tyr
                20                  25                  30

Thr Met His Trp Val Arg Gln Ala Pro Gly Lys Gly Leu Glu Trp Val
                35                  40                  45

Ser Leu Ile Ser Trp Asp Gly Gly Ser Thr Tyr Tyr Ala Asp Ser Val
        50                  55                  60

Lys Gly Arg Phe Thr Ile Ser Arg Asp Asn Ser Lys Asn Ser Leu Tyr
 65                  70                  75                  80

Leu Gln Met Asn Ser Leu Arg Thr Glu Asp Thr Ala Leu Tyr Tyr Cys
                85                  90                  95

Ala Lys

<210> SEQ ID NO 63
<211> LENGTH: 98
<212> TYPE: PRT
<213> ORGANISM: Homo sapiens

<400> SEQUENCE: 63

Gln Val Gln Leu Val Glu Ser Gly Gly Gly Leu Val Lys Pro Gly Gly
 1               5                  10                  15
```

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 64
<211> LENGTH: 100
<212> TYPE: PRT
<213> ORGANISM: Homo sapiens

<400> SEQUENCE: 64

Glu Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asn Ala
            20                  25                  30

Trp Met Ser Trp Val Arg Gln Ala Pro Gly Lys Gly Leu Glu Trp Val
        35                  40                  45

Gly Arg Ile Lys Ser Lys Thr Asp Gly Gly Thr Thr Asp Tyr Ala Ala
    50                  55                  60

Pro Val Lys Gly Arg Phe Thr Ile Ser Arg Asp Asp Ser Lys Asn Thr
65                  70                  75                  80

Leu Tyr Leu Gln Met Asn Ser Leu Lys Thr Glu Asp Thr Ala Val Tyr
                85                  90                  95

Tyr Cys Thr Thr
            100

<210> SEQ ID NO 65
<211> LENGTH: 98
<212> TYPE: PRT
<213> ORGANISM: Homo sapiens

<400> SEQUENCE: 65

Glu Val Gln Leu Val Glu Ser Gly Gly Gly Leu Val Gln Pro Gly Gly
1               5                   10                  15

Ser Leu Arg Leu Ser Cys Pro Ala Ser Gly Phe Thr Phe Ser Asn His
            20                  25                  30

Tyr Met Ser Trp Val Arg Gln Ala Pro Gly Lys Gly Leu Glu Trp Val
        35                  40                  45

Ser Tyr Ile Ser Gly Asp Ser Gly Tyr Thr Asn Tyr Ala Asp Ser Val
    50                  55                  60

Lys Gly Arg Phe Thr Ile Ser Arg Asp Asn Ala Asn Asn Ser Pro Tyr
65                  70                  75                  80

Leu Gln Met Asn Ser Leu Arg Ala Glu Asp Thr Ala Val Tyr Tyr Cys
                85                  90                  95

Val Lys

<210> SEQ ID NO 66
<211> LENGTH: 98
<212> TYPE: PRT

<213> ORGANISM: Homo sapiens

<400> SEQUENCE: 66

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn His
            20                  25                  30

Tyr Thr Ser Trp Val Arg Gln Ala Pro Gly Lys Gly Leu Glu Trp Val
        35                  40                  45

Ser Tyr Ser Ser Gly Asn Ser Gly Tyr Thr Asn Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Val Lys
```

<210> SEQ ID NO 67
<211> LENGTH: 98
<212> TYPE: PRT
<213> ORGANISM: Homo sapiens

<400> SEQUENCE: 67

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Ser
            20                  25                  30

Asp Met Asn Trp Val His Gln Ala Pro Gly Lys Gly Leu Glu Trp Val
        35                  40                  45

Ser Gly Val Ser Trp Asn Gly Ser Arg Thr His Tyr Ala Asp Ser Val
    50                  55                  60

Lys Gly Arg Phe Ile Ile Ser Arg Asp Asn Ser Arg Asn Thr Leu Tyr
65                  70                  75                  80

Leu Gln Thr Asn Ser Leu Arg Ala Glu Asp Thr Ala Val Tyr Tyr Cys
                85                  90                  95

Val Arg
```

<210> SEQ ID NO 68
<211> LENGTH: 97
<212> TYPE: PRT
<213> ORGANISM: Homo sapiens

<400> SEQUENCE: 68

```
Glu Val Gln Leu Val Thr Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg
```

<210> SEQ ID NO 69
<211> LENGTH: 97
<212> TYPE: PRT
<213> ORGANISM: Homo sapiens

<400> SEQUENCE: 69

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg

<210> SEQ ID NO 70
<211> LENGTH: 97
<212> TYPE: PRT
<213> ORGANISM: Homo sapiens

<400> SEQUENCE: 70

Glu Val Gln Leu Val His Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg

<210> SEQ ID NO 71
<211> LENGTH: 97
<212> TYPE: PRT
<213> ORGANISM: Homo sapiens

<400> SEQUENCE: 71

Glu Val Gln Leu Val Gln Ser Gly Gly Gly Leu Val Gln Pro Gly Gly
1               5                   10                  15

Ser Leu Arg Leu Ser Cys Ala Gly Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ser Ala Ile Gly Thr Gly Gly Gly Thr Tyr Tyr Ala Asp Ser Val Lys
    50                  55                  60

Gly Arg Phe Thr Ile Ser Arg Asp Asn Ala Lys Asn Ser Leu Tyr Leu
65                  70                  75                  80

Gln Met Asn Ser Leu Arg Ala Glu Asp Met Ala Val Tyr Tyr Cys Ala
                85                  90                  95

Arg

<210> SEQ ID NO 72
<211> LENGTH: 98
<212> TYPE: PRT
<213> ORGANISM: Homo sapiens

<400> SEQUENCE: 72

Glu Val Gln Leu Val Glu Ser Gly Gly Gly Leu Val Gln Pro Gly Gly
1               5                   10                  15

Ser Leu Arg Leu Ser Cys Ser Ala Ser Gly Phe Thr Phe Ser Ser Tyr
            20                  25                  30

Ala Met His Trp Val Arg Gln Ala Pro Gly Lys Gly Leu Glu Tyr Val
        35                  40                  45

Ser Ala Ile Ser Ser Asn Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Val Gln Met Ser Ser Leu Arg Ala Glu Asp Thr Ala Val Tyr Tyr Cys
                85                  90                  95

Val Arg

<210> SEQ ID NO 73
<211> LENGTH: 35
<212> TYPE: PRT
<213> ORGANISM: Homo sapiens

<400> SEQUENCE: 73

Thr Phe Ser Ser Tyr Ala Met His Trp Val Arg Gln Ala Pro Gly Lys
1               5                   10                  15

Gly Leu Glu Tyr Val Ser Ala Ile Ser Ser Asn Gly Gly Ser Thr Tyr
            20                  25                  30

Tyr Ala Asp
        35

<210> SEQ ID NO 74
<211> LENGTH: 98
<212> TYPE: PRT
<213> ORGANISM: Homo sapiens

<400> SEQUENCE: 74

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

```
<210> SEQ ID NO 75
<211> LENGTH: 98
<212> TYPE: PRT
<213> ORGANISM: Homo sapiens

<400> SEQUENCE: 75

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 76
<211> LENGTH: 98
<212> TYPE: PRT
<213> ORGANISM: Homo sapiens

<400> SEQUENCE: 76

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg

<210> SEQ ID NO 77
<211> LENGTH: 98
<212> TYPE: PRT
<213> ORGANISM: Homo sapiens

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95
Ala Lys
```

<210> SEQ ID NO 78
<211> LENGTH: 97
<212> TYPE: PRT
<213> ORGANISM: Homo sapiens

<400> SEQUENCE: 78

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Asp Met His Trp Val Arg Gln Ala Thr Gly Lys Gly Leu Glu Trp Val
        35                  40                  45
Ser Ala Ile Gly Thr Ala Gly Asp Thr Tyr Tyr Pro Gly Ser Val Lys
    50                  55                  60
Gly Arg Phe Thr Ile Ser Arg Glu Asn Ala Lys Asn Ser Leu Tyr Leu
65                  70                  75                  80
Gln Met Asn Ser Leu Arg Ala Gly Asp Thr Ala Val Tyr Tyr Cys Ala
                85                  90                  95
Arg
```

<210> SEQ ID NO 79
<211> LENGTH: 98
<212> TYPE: PRT
<213> ORGANISM: Homo sapiens

<400> SEQUENCE: 79

```
Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Glu Met Asn Trp Val Arg Gln Ala Pro Gly Lys Gly Leu Glu Trp Val
        35                  40                  45
Ser Tyr Ile Ser Ser Ser Gly Ser Thr Ile Tyr Tyr Ala Asp Ser Val
    50                  55                  60
Lys Gly Arg Phe Thr Ile Ser Arg Asp Asn Ala Lys Asn Ser Leu Tyr
65                  70                  75                  80
Leu Gln Met Asn Ser Leu Arg Ala Glu Asp Thr Ala Val Tyr Tyr Cys
                85                  90                  95
Ala Arg
```

<210> SEQ ID NO 80
<211> LENGTH: 98
<212> TYPE: PRT
<213> ORGANISM: Homo sapiens

<400> SEQUENCE: 80

```
Gln Val Gln Leu Val Glu Ser Gly Gly Gly Val Val Gln Pro Gly Arg
1               5                   10                  15
Ser Leu Arg Leu Ser Cys Ala Ala Ser Gly Phe Thr Phe Ser Ser Tyr
            20                  25                  30
Gly Met His Trp Val Arg Gln Ala Pro Gly Lys Gly Leu Glu Trp Val
        35                  40                  45
Ala Val Ile Ser Tyr Asp Gly Ser Asn Lys Tyr Tyr Ala Asp Ser Val
```

```
                50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                    85                  90                  95

Ala Lys

<210> SEQ ID NO 81
<211> LENGTH: 98
<212> TYPE: PRT
<213> ORGANISM: Homo sapiens

<400> SEQUENCE: 81

Gln Val Gln Leu Val Glu Ser Gly Gly Gly Val Val Gln Pro Gly Arg
 1               5                  10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg

<210> SEQ ID NO 82
<211> LENGTH: 98
<212> TYPE: PRT
<213> ORGANISM: Homo sapiens

<400> SEQUENCE: 82

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Tyr Ile Ser Ser Ser Ser Ser Thr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                85                  90                  95

Ala Arg

<210> SEQ ID NO 83
<211> LENGTH: 97
<212> TYPE: PRT
<213> ORGANISM: Homo sapiens

<400> SEQUENCE: 83

Glu Asp Gln Leu Val Glu Ser Gly Gly Gly Leu Val Gln Pro Gly Gly
 1               5                  10                  15

Ser Leu Arg Pro Ser Cys Ala Ala Ser Gly Phe Ala Phe Ser Ser Tyr
                20                  25                  30
```

-continued

Val Leu His Trp Val Arg Arg Ala Pro Gly Lys Gly Pro Glu Trp Val
         35                  40                  45

Ser Ala Ile Gly Thr Gly Gly Asp Thr Tyr Tyr Ala Asp Ser Val Met
     50                  55                  60

Gly Arg Phe Thr Ile Ser Arg Asp Asn Ala Lys Lys Ser Leu Tyr Leu
65                  70                  75                  80

Gln Met Asn Ser Leu Ile Ala Glu Asp Met Ala Val Tyr Tyr Cys Ala
             85                  90                  95

Arg

<210> SEQ ID NO 84
<211> LENGTH: 98
<212> TYPE: PRT
<213> ORGANISM: Homo sapiens

<400> SEQUENCE: 84

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
             20                  25                  30
Trp Met His Trp Val Arg Gln Ala Pro Gly Lys Gly Leu Val Trp Val
         35                  40                  45
Ser Arg Ile Asn Ser Asp Gly Ser Ser Thr Thr Tyr Ala Asp Ser Val
     50                  55                  60
Lys Gly Arg Phe Thr Ile Ser Arg Asp Asn Ala Lys Asn Thr Leu Tyr
65                  70                  75                  80
Leu Gln Met Asn Ser Leu Arg Ala Glu Asp Thr Ala Val Tyr Tyr Cys
             85                  90                  95
Ala Arg

<210> SEQ ID NO 85
<211> LENGTH: 98
<212> TYPE: PRT
<213> ORGANISM: Homo sapiens

<400> SEQUENCE: 85

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
             20                  25                  30

Trp Met Ser Trp Val Arg Gln Ala Pro Gly Lys Gly Leu Glu Trp Val
         35                  40                  45

Ala Asn Ile Lys Gln Asp Gly Ser Glu Lys Tyr Tyr Val Asp Ser Val
     50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
             85                  90                  95

Ala Arg

<210> SEQ ID NO 86
<211> LENGTH: 97
<212> TYPE: PRT
<213> ORGANISM: Homo sapiens

<400> SEQUENCE: 86

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
             20                  25                  30

```
Tyr Trp Ser Trp Ile Arg Gln Pro Pro Gly Lys Gly Leu Glu Trp Ile
            35                  40                  45

Gly Glu Ile Ile His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 87
<211> LENGTH: 97
<212> TYPE: PRT
<213> ORGANISM: Homo sapiens

<400> SEQUENCE: 87

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Pro Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg

<210> SEQ ID NO 88
<211> LENGTH: 97
<212> TYPE: PRT
<213> ORGANISM: Homo sapiens

<400> SEQUENCE: 88

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Val Ser Gly Tyr
                20                  25                  30

Tyr Trp Ser Trp Ile Arg Gln Pro Pro Gly Lys Gly Leu Glu Trp Ile
            35                  40                  45

Gly Tyr Ile Tyr Tyr Ser Gly Ser Thr Asn Asn Asn Pro Ser Leu Lys
        50                  55                  60

Ser Arg Ala Thr Ile Ser Val Asp Thr Ser Lys Asn Gln Phe Ser Leu
65                  70                  75                  80

Asn Leu Ser Ser Val Thr Ala Ala Asp Thr Ala Val Tyr Cys Cys Ala
                85                  90                  95

Arg

<210> SEQ ID NO 89
<211> LENGTH: 99
<212> TYPE: PRT
<213> ORGANISM: Homo sapiens

<400> SEQUENCE: 89

Gln Leu Gln Leu Gln Glu Ser Gly Ser Gly Leu Val Lys Pro Ser Gln
```

```
                1               5                  10                 15
        Thr Leu Ser Leu Thr Cys Ala Val Ser Gly Gly Ser Ile Ser Ser Gly
                        20                  25                  30

Gly Tyr Ser Trp Ser Trp Ile Arg Gln Pro Pro Gly Lys Gly Leu Glu
                        35                  40                  45

Trp Ile Gly Tyr Ile Tyr His Ser Gly Ser Thr Tyr Tyr Asn Pro Ser
                50                  55                  60

Leu Lys Ser Arg Val Thr Ile Ser Val Asp Arg Ser Lys Asn Gln Phe
         65                  70                  75                  80

Ser Leu Lys Leu Ser Ser Val Thr Ala Ala Asp Thr Ala Val Tyr Tyr
                        85                  90                  95

Cys Ala Arg

<210> SEQ ID NO 90
<211> LENGTH: 99
<212> TYPE: PRT
<213> ORGANISM: Homo sapiens

<400> SEQUENCE: 90

Gln Val Gln Leu Gln Glu Ser Gly Pro Gly Leu Val Lys Pro Ser Gln
         1               5                  10                  15

Thr Leu Ser Leu Thr Cys Thr Val Ser Gly Gly Ser Ile Ser Ser Gly
                        20                  25                  30

Gly Tyr Tyr Trp Ser Trp Ile Arg Gln His Pro Gly Lys Gly Leu Glu
                        35                  40                  45

Trp Ile Gly Tyr Ile Tyr Tyr Ser Gly Ser Thr Tyr Tyr Asn Pro Ser
                50                  55                  60

Leu Lys Ser Arg Val Thr Ile Ser Val Asp Thr Ser Lys Asn Gln Phe
         65                  70                  75                  80

Ser Leu Lys Leu Ser Ser Val Thr Ala Ala Asp Thr Ala Val Tyr Tyr
                        85                  90                  95

Cys Ala Arg

<210> SEQ ID NO 91
<211> LENGTH: 99
<212> TYPE: PRT
<213> ORGANISM: Homo sapiens

<400> SEQUENCE: 91

Gln Val Gln Leu Gln Glu Ser Gly Pro Gly Leu Val Lys Pro Ser Glu
         1               5                  10                  15
        Thr Leu Ser Leu Thr Cys Thr Val Ser Gly Gly Ser Val Ser Ser Gly
                        20                  25                  30
        Ser Tyr Tyr Trp Ser Trp Ile Arg Gln Pro Pro Gly Lys Gly Leu Glu
                        35                  40                  45
        Trp Ile Gly Tyr Ile Tyr Tyr Ser Gly Ser Thr Asn Tyr Asn Pro Ser
                50                  55                  60
        Leu Lys Ser Arg Val Thr Ile Ser Val Asp Thr Ser Lys Asn Gln Phe
         65                  70                  75                  80
        Ser Leu Lys Leu Ser Ser Val Thr Ala Ala Asp Thr Ala Val Tyr Tyr
                        85                  90                  95
        Cys Ala Arg

<210> SEQ ID NO 92
<211> LENGTH: 98
<212> TYPE: PRT
<213> ORGANISM: Homo sapiens

<400> SEQUENCE: 92

Gln Val Gln Leu Gln Glu Ser Gly Pro Gly Leu Val Lys Pro Ser Glu
         1               5                  10                  15
```

```
Thr Leu Ser Leu Thr Cys Ala Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 93
<211> LENGTH: 98
<212> TYPE: PRT
<213> ORGANISM: Homo sapiens

<400> SEQUENCE: 93

Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 94
<211> LENGTH: 98
<212> TYPE: PRT
<213> ORGANISM: Homo sapiens

<400> SEQUENCE: 94

Gln Val Gln Leu Gln Glu Ser Gly Pro Gly Leu Val Lys Pro Ser Asp
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Thr Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
                85                  90                  95

Ala Arg

<210> SEQ ID NO 95
<211> LENGTH: 98
<212> TYPE: PRT
<213> ORGANISM: Homo sapiens
```

<400> SEQUENCE: 95

Gln Val Gln Leu Gln Glu Ser Gly Pro Gly Leu Val Lys Pro Ser Gln
1               5                   10                  15

Thr Leu Ser Leu Thr Cys Ala Val Ser Gly Tyr Ser Ile Ser Ser Ser
            20                  25                  30

Asn Trp Trp Gly Trp Ile Arg Gln Pro Pro Gly Lys Gly Leu Glu Trp
        35                  40                  45

Ile Gly Tyr Ile Tyr Tyr Ser Gly Ser Ile Tyr Tyr Asn Pro Ser Leu
    50                  55                  60

Lys Ser Arg Val Thr Met Ser Val Asp Thr Ser Lys Asn Gln Phe Ser
65                  70                  75                  80

Leu Lys Leu Ser Ser Val Thr Ala Val Asp Thr Ala Val Tyr Tyr Cys
            85                  90                  95

Ala Arg

<210> SEQ ID NO 96
<211> LENGTH: 98
<212> TYPE: PRT
<213> ORGANISM: Homo sapiens

<400> SEQUENCE: 96

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Asn Pro Asn Tyr Asn Pro Ser Leu
    50                  55                  60

Lys Ser Arg Val Thr Ile Ser Ile Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg

<210> SEQ ID NO 97
<211> LENGTH: 98
<212> TYPE: PRT
<213> ORGANISM: Homo sapiens

<400> SEQUENCE: 97

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Pro Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
            85                  90                  95

Ala Arg

<210> SEQ ID NO 98
<211> LENGTH: 98
<212> TYPE: PRT
<213> ORGANISM: Homo sapiens

<400> SEQUENCE: 98

Gln Val Gln Leu Gln Glu Ser Gly Pro Gly Leu Val Lys Pro Pro Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Cys Cys
                85                  90                  95

Ala Arg

<210> SEQ ID NO 99
<211> LENGTH: 98
<212> TYPE: PRT
<213> ORGANISM: Homo sapiens

<400> SEQUENCE: 99

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Thr Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg

<210> SEQ ID NO 100
<211> LENGTH: 99
<212> TYPE: PRT
<213> ORGANISM: Homo sapiens

<400> SEQUENCE: 100

Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
    50                  55                  60

Leu Lys Ser Arg Val Thr Ile Ser Val Asp Thr Ser Lys Asn Gln Phe
65                  70                  75                  80

```
Ser Leu Lys Leu Ser Ser Val Thr Ala Ala Asp Thr Ala Val Tyr Tyr
            85                  90                  95
Cys Ala Arg
```

<210> SEQ ID NO 101
<211> LENGTH: 99
<212> TYPE: PRT
<213> ORGANISM: Homo sapiens

<400> SEQUENCE: 101

```
Gln Leu Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Ser
            20                  25                  30

Ser Tyr Tyr Trp Gly Trp Ile Arg Gln Pro Pro Gly Lys Gly Leu Glu
        35                  40                  45

Trp Ile Gly Ser Ile Tyr Tyr Ser Gly Ser Thr Tyr Tyr Asn Pro Ser
50                  55                  60

Leu Lys Ser Arg Val Thr Ile Ser Val Asp Thr Ser Lys Asn His Phe
65                  70                  75                  80

Ser Leu Lys Leu Ser Ser Val Thr Ala Ala Asp Thr Ala Val Tyr Tyr
            85                  90                  95
Cys Ala Arg
```

<210> SEQ ID NO 102
<211> LENGTH: 97
<212> TYPE: PRT
<213> ORGANISM: Homo sapiens

<400> SEQUENCE: 102

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Ala Gly Lys Gly Leu Glu Trp Ile
        35                  40                  45

Gly Arg Ile Tyr Thr Ser Gly Ser Thr Asn Tyr Asn Pro Ser Leu Lys
50                  55                  60

Ser Arg Val Thr Asn Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
            85                  90                  95
Arg
```

<210> SEQ ID NO 103
<211> LENGTH: 97
<212> TYPE: PRT
<213> ORGANISM: Homo sapiens

<400> SEQUENCE: 103

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser Ser Tyr
            20                  25                  30

Tyr Trp Ser Trp Ile Arg Gln Pro Pro Gly Lys Gly Leu Glu Trp Ile
        35                  40                  45

Gly Tyr Ile Tyr Tyr Ser Gly Ser Thr Asn Tyr Asn Pro Ser Leu Lys
```

```
                50                  55                  60
Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg

<210> SEQ ID NO 104
<211> LENGTH: 97
<212> TYPE: PRT
<213> ORGANISM: Homo sapiens

<400> SEQUENCE: 104

Gln Val Gln Leu Gln Glu Ser Gly Pro Gly Leu Val Lys Pro Ser Glu
 1               5                   10                  15

Thr Leu Ser Leu Thr Cys Thr Val Ser Gly Gly Ser Val Ser Ser Tyr
                 20                  25                  30

Tyr Trp Ser Trp Ile Arg Gln Pro Pro Gly Lys Gly Leu Glu Trp Ile
             35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Met Gln Phe Ser Leu
 65                  70                  75                  80

Lys Leu Ser Ser Val Thr Ala Ala Asp Thr Ala Val Tyr Tyr Cys Ala
                 85                  90                  95

Arg

<210> SEQ ID NO 105
<211> LENGTH: 97
<212> TYPE: PRT
<213> ORGANISM: Homo sapiens

<400> SEQUENCE: 105

Gln Val Gln Leu Gln Glu Ser Gly Pro Gly Leu Val Lys Pro Ser Asp
 1               5                   10                  15

Thr Leu Ser Leu Thr Cys Thr Val Ser Gly Gly Ser Ile Ser Ser Tyr
                 20                  25                  30

Tyr Trp Ser Trp Ile Arg Gln Pro Pro Gly Lys Gly Leu Glu Trp Ile
             35                  40                  45

Gly Tyr Ile Tyr Tyr Ser Gly Ser Thr Asn Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                 85                  90                  95

Arg

<210> SEQ ID NO 106
<211> LENGTH: 98
<212> TYPE: PRT
<213> ORGANISM: Homo sapiens

<400> SEQUENCE: 106

Glu Val Gln Leu Val Gln Ser Gly Ala Glu Val Lys Lys Pro Gly Glu
 1               5                   10                  15

Ser Leu Lys Ile Ser Cys Lys Gly Ser Gly Tyr Ser Phe Thr Ser Tyr
                 20                  25                  30
```

```
Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 107
<211> LENGTH: 98
<212> TYPE: PRT
<213> ORGANISM: Homo sapiens

<400> SEQUENCE: 107

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Pro Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 108
<211> LENGTH: 98
<212> TYPE: PRT
<213> ORGANISM: Homo sapiens

<400> SEQUENCE: 108

Glu Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Trp Ile Gly Trp Val Arg Gln Met Pro Gly Lys Gly Leu Glu Trp Met
            35                  40                  45

Gly Ile Ile Tyr Pro Gly Asp Ser Asp Thr Arg Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg

<210> SEQ ID NO 109
<211> LENGTH: 98
<212> TYPE: PRT
<213> ORGANISM: Homo sapiens

<400> SEQUENCE: 109
```

```
Glu Val Gln Leu Leu Gln Ser Ala Ala Glu Val Lys Arg Pro Gly Glu
1               5                   10                  15

Ser Leu Arg Ile Ser Cys Lys Thr Ser Gly Tyr Ser Phe Thr Ser Tyr
                20                  25                  30

Trp Ile His Trp Val Arg Gln Met Pro Gly Lys Glu Leu Glu Trp Met
            35                  40                  45

Gly Ser Ile Tyr Pro Gly Asn Ser Asp Thr Arg Tyr Ser Pro Ser Phe
50                      55                  60

Gln Gly His Val Thr Ile Ser Ala Asp Ser Ser Ser Thr Ala Tyr
65                  70                  75                  80

Leu Gln Trp Ser Ser Leu Lys Ala Ser Asp Ala Ala Met Tyr Tyr Cys
                85                  90                  95

Val Arg
```

<210> SEQ ID NO 110
<211> LENGTH: 98
<212> TYPE: PRT
<213> ORGANISM: Homo sapiens

<400> SEQUENCE: 110

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
                20                  25                  30

Trp Ile Ser Trp Val Arg Gln Met Pro Gly Lys Gly Leu Glu Trp Met
            35                  40                  45

Gly Arg Ile Asp Pro Ser Asp Ser Tyr Thr Asn Tyr Ser Pro Ser Phe
50                      55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg
```

<210> SEQ ID NO 111
<211> LENGTH: 98
<212> TYPE: PRT
<213> ORGANISM: Homo sapiens

<400> SEQUENCE: 111

```
Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Ser Phe Thr Ser Tyr
                20                  25                  30

Trp Ile Ser Trp Val Arg Gln Met Pro Gly Lys Gly Leu Glu Trp Met
            35                  40                  45

Gly Arg Ile Asp Pro Ser Asp Ser Tyr Thr Asn Tyr Ser Pro Ser Phe
50                      55                  60

Gln Gly His Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg
```

<210> SEQ ID NO 112
<211> LENGTH: 101

```
<212> TYPE: PRT
<213> ORGANISM: Homo sapiens

<400> SEQUENCE: 112

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg
            100

<210> SEQ ID NO 113
<211> LENGTH: 87
<212> TYPE: PRT
<213> ORGANISM: Homo sapiens

<400> SEQUENCE: 113

Arg Lys Leu Gly Ala Ser Val Lys Val Ser Arg Lys Ala Ser Ser Tyr
1               5                   10                  15

Thr Phe Thr Ser Tyr Asp Ile His Cys Val Arg Gln Ala Pro Gly Lys
            20                  25                  30

Gly Leu Lys Gly Trp Met Gly Ile Tyr Ser Gly Asn Gly Lys Thr
        35                  40                  45

Gly Tyr Ala Gln Lys Phe Gln Arg Val Thr Met Thr Arg Asp Met Ser
    50                  55                  60

Thr Ser Thr Ala Tyr Met Glu Leu Ser Ser Gln Arg Ser Glu Asp Ile
65                  70                  75                  80

Asp Val Tyr Tyr Cys Ala Arg
            85

<210> SEQ ID NO 114
<211> LENGTH: 5
<212> TYPE: PRT
<213> ORGANISM: Homo sapiens

<400> SEQUENCE: 114

Asp Tyr Gly Met Ser
1               5

<210> SEQ ID NO 115
<211> LENGTH: 17
<212> TYPE: PRT
<213> ORGANISM: Homo sapiens

<400> SEQUENCE: 115

Gly Ile Asn Trp Asn Gly Gly Ser Thr Gly Tyr Ala Asp Ser Val Lys
1               5                   10                  15

Gly

<210> SEQ ID NO 116
<211> LENGTH: 11
```

```
<212> TYPE: PRT
<213> ORGANISM: Homo sapiens

<400> SEQUENCE: 116

Trp Gly Gln Gly Thr Leu Val Thr Val Ser Arg
1               5                   10

<210> SEQ ID NO 117
<211> LENGTH: 11
<212> TYPE: PRT
<213> ORGANISM: Homo sapiens

<400> SEQUENCE: 117

Ala Glu Asp Thr Ala Val Tyr Tyr Cys Ala Arg
1               5                   10

<210> SEQ ID NO 118
<211> LENGTH: 11
<212> TYPE: PRT
<213> ORGANISM: Homo sapiens

<400> SEQUENCE: 118

Arg Phe Thr Ile Ser Arg Asp Asn Ala Lys Asn
1               5                   10

<210> SEQ ID NO 119
<211> LENGTH: 8
<212> TYPE: PRT
<213> ORGANISM: Homo sapiens

<400> SEQUENCE: 119

Gly Lys Gly Leu Glu Trp Val Ser
1               5

<210> SEQ ID NO 120
<211> LENGTH: 6
<212> TYPE: PRT
<213> ORGANISM: Homo sapiens

<400> SEQUENCE: 120

Trp Val Arg Gln Ala Pro
1               5

<210> SEQ ID NO 121
<211> LENGTH: 11
<212> TYPE: PRT
<213> ORGANISM: Homo sapiens

<400> SEQUENCE: 121

Leu Ser Cys Ala Ala Ser Gly Phe Thr Phe Asp
1               5                   10

<210> SEQ ID NO 122
<211> LENGTH: 7
<212> TYPE: PRT
<213> ORGANISM: Homo sapiens

<400> SEQUENCE: 122

Ala Val Tyr Tyr Cys Ala Arg
1               5

<210> SEQ ID NO 123
<211> LENGTH: 20
<212> TYPE: PRT
<213> ORGANISM: Homo sapiens
```

-continued

<400> SEQUENCE: 123

Gly Gly Gly Gly Ser Gly Gly Gly Ser Gly Gly Gly Ser Gly
1               5                   10                  15

Gly Gly Gly Ser
            20

<210> SEQ ID NO 124
<211> LENGTH: 15
<212> TYPE: PRT
<213> ORGANISM: Homo sapiens

<400> SEQUENCE: 124

Gly Gly Gly Gly Ser Gly Gly Gly Ser Gly Gly Gly Ser
1               5                   10                  15

<210> SEQ ID NO 125
<211> LENGTH: 9
<212> TYPE: PRT
<213> ORGANISM: Homo sapiens

<400> SEQUENCE: 125

Asn Ser Arg Asp Ser Ser Gly Asn His
1               5

<210> SEQ ID NO 126
<211> LENGTH: 8
<212> TYPE: PRT
<213> ORGANISM: Homo sapiens

<400> SEQUENCE: 126

Ala Ala Trp Asp Asp Ser Leu Val
1               5

<210> SEQ ID NO 127
<211> LENGTH: 8
<212> TYPE: PRT
<213> ORGANISM: Homo sapiens

<400> SEQUENCE: 127

Met Gln Ser Ile Gln Leu Pro Thr
1               5

<210> SEQ ID NO 128
<211> LENGTH: 9
<212> TYPE: PRT
<213> ORGANISM: Homo sapiens

<400> SEQUENCE: 128

Met Gln Ser Ile Gln Leu Pro Ala Thr
1               5

<210> SEQ ID NO 129
<211> LENGTH: 10
<212> TYPE: PRT
<213> ORGANISM: Homo sapiens

<400> SEQUENCE: 129

Ala Ala Trp Asp Asp Gly Leu Ser Leu Val
1               5                   10

<210> SEQ ID NO 130
<211> LENGTH: 10
<212> TYPE: PRT

<213> ORGANISM: Homo sapiens

<400> SEQUENCE: 130

Ala Ala Trp Asp Asp Ser Leu Ser Gly Val
1               5                   10

<210> SEQ ID NO 131
<211> LENGTH: 11
<212> TYPE: PRT
<213> ORGANISM: Homo sapiens

<400> SEQUENCE: 131

Asn Ser Arg Asp Ser Ser Gly Ser Val Arg Val
1               5                   10

<210> SEQ ID NO 132
<211> LENGTH: 9
<212> TYPE: PRT
<213> ORGANISM: Homo sapiens

<400> SEQUENCE: 132

Leu Leu Tyr Tyr Gly Gly Ala Tyr Val
1               5

<210> SEQ ID NO 133
<211> LENGTH: 11
<212> TYPE: PRT
<213> ORGANISM: Homo sapiens

<400> SEQUENCE: 133

Asn Ser Arg Asp Ser Ser Gly Val Ser Arg Val
1               5                   10

<210> SEQ ID NO 134
<211> LENGTH: 10
<212> TYPE: PRT
<213> ORGANISM: Homo sapiens

<400> SEQUENCE: 134

Ala Ala Trp Asp Asp Ser Leu Pro Tyr Val
1               5                   10

<210> SEQ ID NO 135
<211> LENGTH: 12
<212> TYPE: PRT
<213> ORGANISM: Homo sapiens

<400> SEQUENCE: 135

Ala Ala Trp Asp Asp Ser Leu Cys Pro Glu Phe Val
1               5                   10

<210> SEQ ID NO 136
<211> LENGTH: 11
<212> TYPE: PRT
<213> ORGANISM: Homo sapiens

<400> SEQUENCE: 136

Ala Ala Trp Asp Asp Ser Leu Ala Trp Phe Val
1               5                   10

<210> SEQ ID NO 137
<211> LENGTH: 10
<212> TYPE: PRT
<213> ORGANISM: Homo sapiens

<400> SEQUENCE: 137

Leu Ala Trp Asp Thr Ser Pro Arg Trp Val
1               5                   10

<210> SEQ ID NO 138
<211> LENGTH: 10
<212> TYPE: PRT
<213> ORGANISM: Homo sapiens

<400> SEQUENCE: 138

Thr Ala Trp Asp Asp Ser Leu Ala Val Val
1               5                   10

<210> SEQ ID NO 139
<211> LENGTH: 11
<212> TYPE: PRT
<213> ORGANISM: Homo sapiens

<400> SEQUENCE: 139

Asn Ser Arg Asp Ser Ser Gly Asn His Arg Val
1               5                   10

<210> SEQ ID NO 140
<211> LENGTH: 9
<212> TYPE: PRT
<213> ORGANISM: Homo sapiens

<400> SEQUENCE: 140

Gln Gln Tyr Gly Ser Ser Gln Arg Thr
1               5

<210> SEQ ID NO 141
<211> LENGTH: 10
<212> TYPE: PRT
<213> ORGANISM: Homo sapiens

<400> SEQUENCE: 141

Ala Ala Trp Asp Asp Ser Leu Arg Leu Val
1               5                   10

<210> SEQ ID NO 142
<211> LENGTH: 9
<212> TYPE: PRT
<213> ORGANISM: Homo sapiens

<400> SEQUENCE: 142

Met Gln Gly Thr His Trp Arg Pro Thr
1               5

<210> SEQ ID NO 143
<211> LENGTH: 9
<212> TYPE: PRT
<213> ORGANISM: Homo sapiens

<400> SEQUENCE: 143

Met Gln Gly Lys His Trp Pro Leu Thr
1               5

<210> SEQ ID NO 144
<211> LENGTH: 9
<212> TYPE: PRT
<213> ORGANISM: Homo sapiens

<400> SEQUENCE: 144

Ala Ala Trp Asp Asp Ser Leu Gly Phe
1               5

<210> SEQ ID NO 145
<211> LENGTH: 9
<212> TYPE: PRT
<213> ORGANISM: Homo sapiens

<400> SEQUENCE: 145

Met Gln Gly Thr His Arg Arg Ala Thr
1               5

<210> SEQ ID NO 146
<211> LENGTH: 9
<212> TYPE: PRT
<213> ORGANISM: Homo sapiens

<400> SEQUENCE: 146

Met Gln Ala Leu Gln Thr Pro Leu Thr
1               5

<210> SEQ ID NO 147
<211> LENGTH: 9
<212> TYPE: PRT
<213> ORGANISM: Homo sapiens

<400> SEQUENCE: 147

Met Arg Gly Thr His Arg Arg Ala Thr
1               5

<210> SEQ ID NO 148
<211> LENGTH: 9
<212> TYPE: PRT
<213> ORGANISM: Homo sapiens

<400> SEQUENCE: 148

Met Gln Gly Thr His Trp His Pro Thr
1               5

<210> SEQ ID NO 149
<211> LENGTH: 8
<212> TYPE: PRT
<213> ORGANISM: Homo sapiens

<400> SEQUENCE: 149

Met Gln Ala Leu Gln Ser Pro Thr
1               5

<210> SEQ ID NO 150
<211> LENGTH: 10
<212> TYPE: PRT
<213> ORGANISM: Homo sapiens

<400> SEQUENCE: 150

Ala Ala Trp Asp Asp Ser Leu Ala Phe Val
1               5                   10

<210> SEQ ID NO 151
<211> LENGTH: 8
<212> TYPE: PRT
<213> ORGANISM: Homo sapiens

<400> SEQUENCE: 151

Met Gln Ala Leu Gln Thr Pro Thr
1               5

<210> SEQ ID NO 152
<211> LENGTH: 8
<212> TYPE: PRT
<213> ORGANISM: Homo sapiens

<400> SEQUENCE: 152

Gln Gln Ser Tyr Ser Thr Arg Thr
1               5

<210> SEQ ID NO 153
<211> LENGTH: 9
<212> TYPE: PRT
<213> ORGANISM: Homo sapiens

<400> SEQUENCE: 153

Met Gln Gly Thr His Trp Pro Phe Thr
1               5

<210> SEQ ID NO 154
<211> LENGTH: 9
<212> TYPE: PRT
<213> ORGANISM: Homo sapiens

<400> SEQUENCE: 154

Met Gln Gly Thr His Trp Pro Ala Thr
1               5

<210> SEQ ID NO 155
<211> LENGTH: 10
<212> TYPE: PRT
<213> ORGANISM: Homo sapiens

<400> SEQUENCE: 155

Ala Ala Trp Asp Asp Ser Leu Arg Ser Val
1               5                   10

<210> SEQ ID NO 156
<211> LENGTH: 9
<212> TYPE: PRT
<213> ORGANISM: Homo sapiens

<400> SEQUENCE: 156

Ala Ala Trp Asp Asp Ser Leu Leu Val
1               5

<210> SEQ ID NO 157
<211> LENGTH: 11
<212> TYPE: PRT
<213> ORGANISM: Homo sapiens

<400> SEQUENCE: 157

Asp Ser Trp Asp Asn Ser Leu Val Ser Pro Val
1               5                   10

<210> SEQ ID NO 158
<211> LENGTH: 9
<212> TYPE: PRT
<213> ORGANISM: Homo sapiens

<400> SEQUENCE: 158

Met Gln Ala Leu Gln Ser Pro Ala Thr
1               5

```
<210> SEQ ID NO 159
<211> LENGTH: 9
<212> TYPE: PRT
<213> ORGANISM: Homo sapiens

<400> SEQUENCE: 159

Met Gln Ala Leu Gln Thr Pro Val Thr
1               5

<210> SEQ ID NO 160
<211> LENGTH: 11
<212> TYPE: PRT
<213> ORGANISM: Homo sapiens

<400> SEQUENCE: 160

Ala Ala Trp Asp Asp Ser Leu Ser Ala Tyr Val
1               5                   10

<210> SEQ ID NO 161
<211> LENGTH: 11
<212> TYPE: PRT
<213> ORGANISM: Homo sapiens

<400> SEQUENCE: 161

Asn Ser Arg Asp Ser Ser Gly Arg Val Asn Val
1               5                   10

<210> SEQ ID NO 162
<211> LENGTH: 8
<212> TYPE: PRT
<213> ORGANISM: Homo sapiens

<400> SEQUENCE: 162

Met Gln Ala Leu Arg Thr Arg Thr
1               5

<210> SEQ ID NO 163
<211> LENGTH: 11
<212> TYPE: PRT
<213> ORGANISM: Homo sapiens

<400> SEQUENCE: 163

Ala Ala Trp Asp Asp Ser Leu Phe Tyr Pro Val
1               5                   10

<210> SEQ ID NO 164
<211> LENGTH: 9
<212> TYPE: PRT
<213> ORGANISM: Homo sapiens

<400> SEQUENCE: 164

Met Gln Gly Thr His Trp Pro Val Thr
1               5

<210> SEQ ID NO 165
<211> LENGTH: 8
<212> TYPE: PRT
<213> ORGANISM: Homo sapiens

<400> SEQUENCE: 165

Met Gln Gly Thr His Trp Arg Thr
1               5

<210> SEQ ID NO 166
<211> LENGTH: 10
```

```
<212> TYPE: PRT
<213> ORGANISM: Homo sapiens

<400> SEQUENCE: 166

Ala Ala Trp Asp Asp Ser Leu Phe Tyr Val
1               5                   10

<210> SEQ ID NO 167
<211> LENGTH: 9
<212> TYPE: PRT
<213> ORGANISM: Homo sapiens

<400> SEQUENCE: 167

Met Gln Ser Ile Gln Leu Pro Leu Thr
1               5

<210> SEQ ID NO 168
<211> LENGTH: 11
<212> TYPE: PRT
<213> ORGANISM: Homo sapiens

<400> SEQUENCE: 168

Ala Ala Trp Asp Asp Ser Leu Leu Gly Ser Val
1               5                   10

<210> SEQ ID NO 169
<211> LENGTH: 9
<212> TYPE: PRT
<213> ORGANISM: Homo sapiens

<400> SEQUENCE: 169

Cys Ser Tyr Ala Gly Ser Ser Tyr Val
1               5

<210> SEQ ID NO 170
<211> LENGTH: 8
<212> TYPE: PRT
<213> ORGANISM: Homo sapiens

<400> SEQUENCE: 170

Gln Gln Asp Tyr Asn Leu Leu Thr
1               5

<210> SEQ ID NO 171
<211> LENGTH: 10
<212> TYPE: PRT
<213> ORGANISM: Homo sapiens

<400> SEQUENCE: 171

Val Leu Tyr Met Gly Ser Gly Ser Ala Val
1               5                   10

<210> SEQ ID NO 172
<211> LENGTH: 9
<212> TYPE: PRT
<213> ORGANISM: Homo sapiens

<400> SEQUENCE: 172

Met Gln Arg Ile Glu Phe Pro Asn Thr
1               5

<210> SEQ ID NO 173
<211> LENGTH: 11
<212> TYPE: PRT
<213> ORGANISM: Homo sapiens
```

<400> SEQUENCE: 173

Ala Ala Trp Asp Asp Ser Leu Ala Cys Ala Val
1               5                   10

<210> SEQ ID NO 174
<211> LENGTH: 8
<212> TYPE: PRT
<213> ORGANISM: Homo sapiens

<400> SEQUENCE: 174

Gln Gln Ala Asn Ser Phe Arg Thr
1               5

<210> SEQ ID NO 175
<211> LENGTH: 11
<212> TYPE: PRT
<213> ORGANISM: Homo sapiens

<400> SEQUENCE: 175

Ala Ala Trp Asp Asp Ser Leu Ser Arg Pro Val
1               5                   10

<210> SEQ ID NO 176
<211> LENGTH: 10
<212> TYPE: PRT
<213> ORGANISM: Homo sapiens

<400> SEQUENCE: 176

Ala Ala Trp Asp Asp Ser Leu Tyr Asn Val
1               5                   10

<210> SEQ ID NO 177
<211> LENGTH: 11
<212> TYPE: PRT
<213> ORGANISM: Homo sapiens

<400> SEQUENCE: 177

Ala Ala Trp Asp Asp Ser Leu Asn Arg Asn Val
1               5                   10

<210> SEQ ID NO 178
<211> LENGTH: 8
<212> TYPE: PRT
<213> ORGANISM: Homo sapiens

<400> SEQUENCE: 178

Met Gln Val Leu Gln Thr Arg Thr
1               5

<210> SEQ ID NO 179
<211> LENGTH: 8
<212> TYPE: PRT
<213> ORGANISM: Homo sapiens

<400> SEQUENCE: 179

Met Gln Ala Leu Gln Thr Arg Thr
1               5

<210> SEQ ID NO 180
<211> LENGTH: 8
<212> TYPE: PRT
<213> ORGANISM: Homo sapiens

<400> SEQUENCE: 180

```
Gln Gln Ser Tyr Ser Thr Arg Met
1               5

<210> SEQ ID NO 181
<211> LENGTH: 8
<212> TYPE: PRT
<213> ORGANISM: Homo sapiens

<400> SEQUENCE: 181

Met Gln Ala Leu Gln Thr Leu Thr
1               5

<210> SEQ ID NO 182
<211> LENGTH: 8
<212> TYPE: PRT
<213> ORGANISM: Homo sapiens

<400> SEQUENCE: 182

Met Arg Ala Leu Gln Thr Pro Thr
1               5

<210> SEQ ID NO 183
<211> LENGTH: 11
<212> TYPE: PRT
<213> ORGANISM: Homo sapiens

<400> SEQUENCE: 183

Ala Ala Trp Asp Asp Ser Leu Pro Gly Tyr Val
1               5                   10

<210> SEQ ID NO 184
<211> LENGTH: 10
<212> TYPE: PRT
<213> ORGANISM: Homo sapiens

<400> SEQUENCE: 184

Ala Ala Trp Asp Asp Ser Leu Gly Phe Val
1               5                   10

<210> SEQ ID NO 185
<211> LENGTH: 10
<212> TYPE: PRT
<213> ORGANISM: Homo sapiens

<400> SEQUENCE: 185

Ala Ala Trp Asp Asp Ser Leu Phe Leu Val
1               5                   10

<210> SEQ ID NO 186
<211> LENGTH: 8
<212> TYPE: PRT
<213> ORGANISM: Homo sapiens

<400> SEQUENCE: 186

Met Gln Ser Ile Gln Leu Arg Thr
1               5

<210> SEQ ID NO 187
<211> LENGTH: 10
<212> TYPE: PRT
<213> ORGANISM: Homo sapiens

<400> SEQUENCE: 187

Ala Ala Trp Asp Asp Ser Leu Ser Ile Val
```

<210> SEQ ID NO 188
<211> LENGTH: 8
<212> TYPE: PRT
<213> ORGANISM: Homo sapiens

<400> SEQUENCE: 188

Met Gln Gly Thr His Trp Pro Thr
1               5

<210> SEQ ID NO 189
<211> LENGTH: 8
<212> TYPE: PRT
<213> ORGANISM: Homo sapiens

<400> SEQUENCE: 189

Met Gln Ala Leu His Thr Arg Thr
1               5

<210> SEQ ID NO 190
<211> LENGTH: 9
<212> TYPE: PRT
<213> ORGANISM: Homo sapiens

<400> SEQUENCE: 190

Asn Ser Arg Asp Ser Ser Gly Ser Val
1               5

<210> SEQ ID NO 191
<211> LENGTH: 9
<212> TYPE: PRT
<213> ORGANISM: Homo sapiens

<400> SEQUENCE: 191

Gln Gln Tyr Gly Ser Ser Pro Tyr Thr
1               5

<210> SEQ ID NO 192
<211> LENGTH: 8
<212> TYPE: PRT
<213> ORGANISM: Homo sapiens

<400> SEQUENCE: 192

Gln Gln Ser Tyr Ser Thr Arg Thr
1               5

<210> SEQ ID NO 193
<211> LENGTH: 9
<212> TYPE: PRT
<213> ORGANISM: Homo sapiens

<400> SEQUENCE: 193

Gln Gln Ala Asn Ser Phe Ala Ala Thr
1               5

<210> SEQ ID NO 194
<211> LENGTH: 9
<212> TYPE: PRT
<213> ORGANISM: Homo sapiens

<400> SEQUENCE: 194

Gln Gln Ala Asn Ser Phe Pro Ala Thr
1               5

```
<210> SEQ ID NO 195
<211> LENGTH: 10
<212> TYPE: PRT
<213> ORGANISM: Homo sapiens

<400> SEQUENCE: 195

Val Leu Tyr Met Gly Ser Gly Val Tyr Val
1               5                   10

<210> SEQ ID NO 196
<211> LENGTH: 11
<212> TYPE: PRT
<213> ORGANISM: Homo sapiens

<400> SEQUENCE: 196

Ala Ala Trp Asp Asp Ser Leu Trp Ser Ala Val
1               5                   10

<210> SEQ ID NO 197
<211> LENGTH: 12
<212> TYPE: PRT
<213> ORGANISM: Homo sapiens

<400> SEQUENCE: 197

Ala Ala Trp Asp Asp Ser Leu Pro Arg Arg Leu Val
1               5                   10

<210> SEQ ID NO 198
<211> LENGTH: 11
<212> TYPE: PRT
<213> ORGANISM: Homo sapiens

<400> SEQUENCE: 198

Ala Ala Trp Asp Asp Ser Leu Pro Ser Gly Val
1               5                   10

<210> SEQ ID NO 199
<211> LENGTH: 8
<212> TYPE: PRT
<213> ORGANISM: Homo sapiens

<400> SEQUENCE: 199

Met Gln Ala Leu Gln Thr Leu Thr
1               5

<210> SEQ ID NO 200
<211> LENGTH: 10
<212> TYPE: PRT
<213> ORGANISM: Homo sapiens

<400> SEQUENCE: 200

Ala Ala Trp Asp Asp Gly Leu Leu Arg Val
1               5                   10

<210> SEQ ID NO 201
<211> LENGTH: 10
<212> TYPE: PRT
<213> ORGANISM: Homo sapiens

<400> SEQUENCE: 201

Ala Ala Trp Asp Asp Ser Leu Ala Leu Val
1               5                   10

<210> SEQ ID NO 202
```

```
<211> LENGTH: 11
<212> TYPE: PRT
<213> ORGANISM: Homo sapiens

<400> SEQUENCE: 202

Asn Ser Arg Asp Ser Ser Gly Phe Gln Leu Val
1               5                   10

<210> SEQ ID NO 203
<211> LENGTH: 277
<212> TYPE: PRT
<213> ORGANISM: Homo sapiens

<400> SEQUENCE: 203

Met Lys Tyr Leu Leu Pro Thr Ala Ala Ala Gly Leu Leu Leu Leu Ala
1               5                   10                  15

Ala Gln Pro Ala Met Ala Glu Val Gln Leu Val Glu Ser Gly Gly Gly
                20                  25                  30

Val Val Arg Pro Gly Gly Ser Leu Arg Leu Ser Cys Ala Ala Ser Gly
            35                  40                  45

Phe Thr Phe Asp Asp Tyr Gly Met Ser Trp Val Arg Gln Ala Pro Gly
        50                  55                  60

Lys Gly Leu Glu Trp Val Ser Gly Ile Asn Trp Asn Gly Gly Ser Thr
65                  70                  75                  80

Gly Tyr Ala Asp Ser Val Lys Gly Arg Phe Thr Ile Ser Arg Asp Asn
                85                  90                  95

Ala Lys Asn Ser Leu Tyr Leu Gln Met Asn Ser Leu Arg Ala Glu Asp
            100                 105                 110

Thr Ala Val Tyr Tyr Cys Ala Arg Leu Thr His Pro Tyr Phe Trp Gly
        115                 120                 125

Gln Gly Thr Leu Val Thr Val Ser Arg Gly Gly Gly Gly Ser Gly Gly
    130                 135                 140

Gly Gly Ser Gly Gly Gly Ser Ser Glu Leu Thr Gln Asp Pro Ala
145                 150                 155                 160

Val Ser Val Ala Leu Gly Gln Thr Val Arg Ile Thr Cys Gln Gly Asp
                165                 170                 175

Ser Leu Arg Ser Tyr Tyr Ala Ser Trp Tyr Gln Gln Lys Pro Gly Gln
            180                 185                 190

Ala Pro Val Leu Val Ile Tyr Gly Lys Asn Asn Arg Pro Ser Gly Ile
        195                 200                 205

Pro Asp Arg Phe Ser Gly Ser Ser Ser Gly Asn Thr Ala Ser Leu Thr
    210                 215                 220

Ile Thr Gly Ala Gln Ala Glu Asp Glu Ala Asp Tyr Tyr Cys Asn Ser
225                 230                 235                 240

Arg Asp Ser Ser Gly Asn His Val Val Phe Gly Gly Gly Thr Lys Leu
                245                 250                 255

Thr Val Leu Gly Ala Ala Ala Glu Gln Lys Leu Ile Ser Glu Glu Asp
            260                 265                 270

Leu Asn Gly Ala Ala
            275
```

The invention claimed is:

1. A peptide or polypeptide or a fragment thereof comprising an Fv molecule, wherein said Fv molecule comprises a heavy chain variable region and a light chain variable region, and
wherein the Fv is a scFv or a dsFv, and optionally having one or more tags, and wherein the heavy chain variable region comprises CDR3, CDR2 and CDR1 regions comprising the amino acid sequences SEQ ID NOs:8, 115 and 114, respectively; and
wherein the Fv molecule is capable of binding one or more cell types selected from the group consisting of leukemia cells and cells expressing glycocalicin.

2. The peptide or polypeptide of claim 1, wherein the heavy chain variable region comprises CDR3, CDR2 and CDR1 regions consisting of the amino acid sequences SEQ ID NOs:8, 115 and 114, respectively.

3. The peptide or polypeptide of claim 1, wherein the CDR3 region consists of SEQ ID NO:8.

4. The peptide or polypeptide of claim 1, wherein the CDR2 region consists of SEQ ID NO:115.

5. The peptide or polypeptide of claim 1, wherein the CDR1 region consists of SEQ ID NO:114.

6. The peptide or polypeptide of claim 1 wherein the leukemia cells are selected from the group consisting of B lineage leukemia cells, T lineage leukemia cells, and myeloid lineage leukemia cells.

7. The peptide or polypeptide of claim 6 wherein the B lineage leukemia cells are selected from the group consisting of B-CLL and B-ALL.

8. The peptide or polypeptide of claim 6, wherein the myeloid lineage leukemia cells are selected from the group consisting of CML and AML.

9. The peptide or polypeptide of claim 1, wherein the cells expressing glycocalicin are platelets.

10. The peptide or polypeptide of claim 2, wherein the light chain variable region consists of SEQ ID NO:7.

11. A scFv consisting of SEQ ID NO:25.

12. A scFv consisting of SEQ ID NO:208.

* * * * *